United States Patent
Curtis et al.

(10) Patent No.: US 12,256,742 B2
(45) Date of Patent: *Mar. 25, 2025

(54) COMPOSITIONS COMPRISING RECOMBINANT BACILLUS CELLS AND ANOTHER BIOLOGICAL CONTROL AGENT

(71) Applicant: BASF CORPORATION, Florham Park, NJ (US)

(72) Inventors: Damian Curtis, Davis, CA (US); Brian Thompson, Creve Coeur, MO (US)

(73) Assignee: BASF CORPORATION, Florham Park, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/487,437

(22) Filed: Oct. 16, 2023

(65) Prior Publication Data

US 2024/0188570 A1   Jun. 13, 2024

Related U.S. Application Data

(63) Continuation of application No. 17/813,065, filed on Jul. 18, 2022, now Pat. No. 11,785,949, which is a continuation of application No. 16/857,448, filed on Apr. 24, 2020, now Pat. No. 11,388,903, which is a continuation of application No. 15/511,822, filed as application No. PCT/US2015/050592 on Sep. 17, 2015, now Pat. No. 10,667,522.

(60) Provisional application No. 62/051,911, filed on Sep. 17, 2014.

(51) Int. Cl.
| | |
|---|---|
| *A61K 39/002* | (2006.01) |
| *A01N 37/46* | (2006.01) |
| *A01N 63/22* | (2020.01) |
| *A01N 63/23* | (2020.01) |
| *A01N 63/50* | (2020.01) |
| *C07K 14/32* | (2006.01) |
| *A01N 37/00* | (2006.01) |
| *C07K 14/00* | (2006.01) |

(52) U.S. Cl.
CPC ............ *A01N 63/50* (2020.01); *A01N 37/46* (2013.01); *A01N 63/22* (2020.01); *A01N 63/23* (2020.01); *C07K 14/32* (2013.01); *A01N 37/00* (2013.01); *C07K 14/00* (2013.01)

(58) Field of Classification Search
None
See application file for complete search history.

(56) References Cited

U.S. PATENT DOCUMENTS

| | | | |
|---|---|---|---|
| 6,060,051 A | 5/2000 | Heins et al. | |
| 6,184,440 B1 | 2/2001 | Shoseyov et al. | |
| 6,333,302 B1 | 12/2001 | Beer et al. | |
| 7,615,681 B2 | 11/2009 | Georges et al. | |
| 8,461,419 B2 | 6/2013 | He et al. | |
| 9,132,175 B2 | 9/2015 | Stewart et al. | |
| 9,133,251 B2 | 9/2015 | Stewart et al. | |
| 9,573,980 B2 | 2/2017 | Thompson et al. | |
| 10,667,522 B2 | 6/2020 | Curtis et al. | |
| 11,785,949 B2 | 10/2023 | Curtis et al. | |
| 2003/0228679 A1 | 12/2003 | Smith et al. | |
| 2011/0281316 A1 | 11/2011 | Stewart et al. | |
| 2013/0216653 A1 | 8/2013 | Perkins et al. | |
| 2014/0274707 A1 | 9/2014 | Thompson et al. | |
| 2014/0342905 A1 | 11/2014 | Bullis et al. | |
| 2016/0031948 A1 | 2/2016 | Thompson et al. | |
| 2016/0051656 A1 | 2/2016 | Stewart et al. | |
| 2016/0053222 A1 | 2/2016 | Stewart et al. | |
| 2016/0108096 A1 | 4/2016 | Thompson et al. | |

FOREIGN PATENT DOCUMENTS

| | | |
|---|---|---|
| JP | 2000-253870 A | 9/2000 |
| WO | WO-02/00232 A2 | 1/2002 |
| WO | WO-2003/066846 A1 | 8/2003 |
| WO | WO-2005/028654 A1 | 3/2005 |
| WO | WO-2005/118552 A2 | 12/2005 |
| WO | WO-2006/012366 A2 | 2/2006 |
| WO | WO-2007/078127 A1 | 7/2007 |
| WO | WO-2008/017483 A2 | 2/2008 |

(Continued)

OTHER PUBLICATIONS

Berlemont, R., et al., "Phylogenetic Distribution of Potential Cellulases in Bacteria," Mar. 2013, Applied and Environmental Microbiology, vol. 79, No. 5, pp. 1545-1554.

(Continued)

*Primary Examiner* — Jennifer E Graser
(74) *Attorney, Agent, or Firm* — MARSHALL, GERSTEIN & BORUN LLP

(57) ABSTRACT

The present invention relates to a composition comprising a) recombinant exosporium-producing *Bacillus* cells that express a fusion protein comprising: (i) at least one plant growth stimulating protein or peptide and (ii) a targeting sequence that localizes the fusion protein to the exosporium of the *Bacillus* cells; and b) at least one further biological control agent selected from particular microorganisms disclosed herein and/or a mutant of a specific strain of a microorganism disclosed herein having all identifying characteristics of the respective strain, and/or at least one metabolite produced by the respective strain, and/or at least one metabolite produced by the respective strain that exhibits activity against insects, mites, nematodes and/or phytopathogens in a synergistically effective amount. Furthermore, the present invention relates to the use of this composition as well as a method for enhancing plant growth, promoting plant health, and/or reducing overall damage of plants and plant parts.

20 Claims, 1 Drawing Sheet
Specification includes a Sequence Listing.

(56) References Cited

FOREIGN PATENT DOCUMENTS

| WO | WO-2010/128003 A2 | 11/2010 |
| --- | --- | --- |
| WO | WO-2013/090628 A1 | 6/2013 |
| WO | WO-2013/110591 A1 | 8/2013 |
| WO | WO-2016/044529 A1 | 3/2016 |
| WO | WO-2016/044533 A1 | 3/2016 |
| WO | WO-2016/044542 A1 | 3/2016 |
| WO | WO-2016/044548 A1 | 3/2016 |
| WO | WO-2016/044563 A1 | 3/2016 |
| WO | WO-2016/044575 A1 | 3/2016 |

OTHER PUBLICATIONS

Chapman, K. D., "Phospholipase Activity During Plant Growth and Development and In Response to Environmental Stress," Trends in Plant Sciences, 1998, vol. 3, pp. 419-426.
Choudhary, D.K., "Interactions of *Bacillus* spp. and Plants—With Special Reference to Induced Systemic Resistance (ISR)," Microbiological Research, 2009, vol. 164, pp. 493-513.
Curtis, et al., U.S. Appl. No. 14/857,176, filed Sep. 17, 2015, titled "Compositions Comprising Recombinant Bacillus Cells and Another Biological Control Agent."
Curtis, et al., U.S. Appl. No. 15/511,822, filed Mar. 16, 2017, titled "Compositions Comprising Recombinant Bacillus Cells and Another Biological Control Agent."
Curtis, et al., U.S. Appl. No. 15/511,835, filed Mar. 16, 2017, titled "Compositions Comprising Recombinant Bacillus Cells and A Fungicide."
Curtis, et al., U.S. Appl. No. 15/511,839, filed Mar. 16, 2017, titled "Compositions Comprising Recombinant Bacillus Cells and Another Biological Control Agent."
Curtis, et al., U.S. Appl. No. 15/511,854, filed Mar. 16, 2017, titled "Compositions Comprising Recombinant Bacillus Cells and A Fungicide."
Curtis, et al., U.S. Appl. No. 15/511,864, filed Mar. 16, 2017, titled "Compositions Comprising Recombinant Bacillus Cells and An Insecticide."
Dowd, P.E., et al., "The Emerging Roles of Phospholipase C in Plant Growth and Development," T. Munnik (ed.), Lipid Signaling in Plants, Plant Cell Monographs 16, 2010, pp. 23-37.
Driss, et al., "Extraccellular Phytase Activity of Bacillus amyloliquefaciens FZB45 Contributes to its Plant-growth-promoting Effect," Microbiology, 2002, vol. 148, pp. 2097-2109.
Frankel A. E. et al., "Characterization of diphtheria fusion proteins targeted to the human interleukin-3 receptor," Jrotein Engineering, 2000, vol. 13, No. 8, pp. 575-581.
Gnanaraj, M., et al., "Isolation and Gene Expression Analysis of Phospholipase C in Response to Abiotic Stresses from Vigna radiata (L.) Wilczek," Jun. 2015, Indian Journal of Experimental Biology, vol. 53, pp. 335-341.
Gujar, P.O., et al., "Effect of Phytase from Aspergillus niger on Plant Growth and Mineral Assimilation in Wheat ;Triticum aestivum Linn.) and Its Potential for Use as a Soil Amendment," 2013, J_Sci. Food Agric., vol. 93, pp. 2242-2247.
Hafeez, F.Y., et al., "PGPR: Versatile Tool to Combat Soil Borne Pathogens and Improve Plant Health," 2011, okspects of Applied Biology, vol. 106, pp. 241-245.
Han, W., et al., "The Application of Exogenous Cellulose to Improve Soil Fertility and Plant Growth Due to Acceleration of Straw Decomposition," Bioresource Technol, 2010, vol. 101, pp. 3724-3731.
Hartati, et al., "Overexpression of Poplar Cellulase Accelerates Growth and Disturbs the Closing Movements of Leaves in Sengon," Plant Physiology, 2008, vol. 147, pp. 552-561.
Hong, Y., et al., "Phospholipases in Plant Response to Nitrogen and Phosphorus Availability," Springer, Jhospholipases in Plant Signaling and Communication in Plants, 2013, vol. 20, pp. 159-180.

Hontzeas, N., et al., "Changes in Gene Expression in Canola Roots Induced by ACC-Deaminase-Containing Plant-Growth-Promoting Bacteria," 2004, MPMI, vol. 17, No. 8, pp. 865-871.
International Search Report and Written Opinion of the International Searching Authority, PCT International Patent okpplication No. PCT/US2015/050592, issued Nov. 11, 2015, 12 pages.
International Search Report and Written Opinion of the International Searching Authority, PCT International Patent okpplication No. PCT/US2015/050621, issued Nov. 3, 2015, 12 pages.
Jackson, W.T., "Effect of Pectinase and Cellulase Preparations on the Growth and Development of Root Hairs," hysiologia Plantarum, 2006 (first published in 1959), vol. 12, pp. 502-510.
Kong, Z., et al., "Effects of 1-Aminocyclopropane-1-carboxylate (ACC) Deaminase-Overproducing Sinorhizobium -neliloti on Plant Growth and Copper Tolerance of Medicago lupulina," Jun. 2015, Plant and Soil, vol. 391, issue 1, pp. 383-398.
Li et al., "An ACC Deaminase Minus Mutant of Enterobacter cloacae UW4 No Longer Promotes Root elongation," 2000, Current Microbiology, vol. 41, pp. 101-105.
Li et al. "Cloning of the Thermostable Cellulase Gene From Newly Isolated Bacillus subtilis and its Expression n *Eschenchia coli*," Molecular Biotechnology, 2008, vol. 40, No. 2, pp. 195-201.
Medie, F.M., "Genome Analyses Highlight the Different Biological Roles of Cellulases," Nature Reviews Microbiology, Mar. 2012, vol. 10, pp. 227-234.
Mikayama et al., Molecular Cloning and Functional Expression of a cDNA Encoding Glycosylation-Inhibiting Factor, Proc. Natl. Acad. Sci. USA, 90(21):10056-60 (1993).
Pakula A. A. et al., "Genetic analysis of protein stability and function," Annual Review of Genetics, 1989, vol. 23, 'ages 289-310.
Peng, Q., et al., "The Regulation of Exosporium-Related Genes in Bacillus thuringiensis," 2015, International Letters of Natural Science, vol. 6, No. 19005, pp. 1-12.
Phitsuwan, P., et al., "Present and Potential Applications of Cellulases in Agriculture, Biotechnology, and Bioenergy," 2013, Folia Microbiol, vol. 58, pp. 163-176.
Pilar-Izquierdo, et al., "Barley seed coating with free and immobilized alkaline phosphatase to improve P uptake and plant growth," Journal of Agricultural Science, 2012, vol. 150, pp. 691-701.
Ping, R., et al., Abstract, 2005, Journal of Northwest Forestry College, vol. 20, No. 1:78-79.
Priest, F., et al., "Population Structure and Evolution of the *Bacillus cereus* Group," 2004, Journal of Bacteriology, vol. 186, No. 23, pp. 7959-7970.
Raddadi N. et al., "Screening of Plant Growth Promoting Traits of Bacillus thuringiensis," 2008, Annals of Microbiology, vol. 58, No. 1, pp. 47-52.
Reetha, S., et al., "Screening of Cellulase and Pectinase by Using Pseudomonas fluorescence and Bacillus subtilis," 2014, International Letters of Natural Science, vol. 8, No. 2, pp. 75-80.
Rudinger et al., Peptide Hormones, Biol. Council, pp. 5-7 (Jun. 1976).
Sales, J., et al., "Coffee (*Coffea arabica* L) Seeds Germination After Treatment with Different Concentrations and Embebding Times in Celluslase", Cienc. Agrotec. [online]. 2003, vol. 27, No. 3, pp. 557-564 ISSN 1413-7054. http://dx. Joi.org/10.1590/51413-70542003000300009, Abstract, 1 page.
Shani, et al., "Expression of Endo-1,4-beta-glucanase (cell) in *Arabidopsis thaliana* is Associated with Plant Growth, Kylem Development and Cell Wall Thickening," Plant Cell Rep., 2006, vol. 10, pp. 1067-1074.
Shen, et al., "Effect of Plant Growth-promoting Rhizobacteria (PGPRs) on Plant Growth, Yield, and Quality of Tomato (Lycopersicon esculentum Mill.) under Simulated Seawater Irrigation," J Gen Appl Microbial. 2012, vol. 58, pp. 253-262.
Singh, B. et al. "Microbial Phytases in Phosphorus Acquisition and Plant Growth Promotion," Apr.-Jun. 2011, hysiol. Mol. Biol. Plants, vol. 17, No. 2, pp. 93-103.
Stewart, G.C., et al., U.S. Appl. No. 14/849,123, filed Sep. 9, 2015, titled "Bacillus Based Delivery System and Methods of Use".
Stewart, G.C., et al., U.S. Appl. No. 14/849,295, filed Sep. 9, 2015, titled "Bacillus Based Delivery System and Methods of Use".

(56) References Cited

OTHER PUBLICATIONS

Tan, L., et al., "Sequence Motifs and Proteolytic Cleavage of the Collagen-Like Glycoprotein BclA Required for Its 4ttachment to the Exosporium of Bacillus anthracis," Mar. 2010, Journal of Bacteriology, vol. 192, No. 5, pp. 1259-1268.
Thompson, B., et al., U.S. Appl. No. 14/213,525, filed Mar. 14, 2014, titled "Fusion Proteins and Methods for Stimulating Plant Growth, Protecting Plants from Pathogens, and Immobilizing Bacillus Spores on Plant Roots".
Thompson, B., et al., U.S. Appl. No. 14/775,892, filed Sep. 14, 2015, titled "Fusion Proteins and Methods for Stimulating Plant Growth, Protecting Plants, and Immobilizing Bacillus Spores on Plants".
Thompson, B., et al., U.S. Appl. No. 14/857,606, filed Sep. 17, 2015, titled "Fusion Proteins, Recombinant Bacteria, and Methods for Using Recombinant Bacteria".
Thompson, et al., U.S. Appl. No. 15/414,050, filed Jan. 24, 2017, titled "Fusion Proteins and Methods for Stimulating Plant Growth, Protecting Plants from Pathogens, and Immobilizing Bacillus Spores on Plant Roots."
U.S. Patent Application No. 15/461, 188.
Yin et al., Synergistic and antagonistic drug combinations depend on network topology, PLoS One, 9(4):e93960 (2014).
Wang, et al., "PLD: Phospholipase Ds in Plant Signaling," Springer, Phospholipases in Plant Signaling, Signaling and Communication in Plants, 2013, vol. 20, pp. 3-26.

| Sequence | SEQ ID NO. | 20-35 % Identity | 25-35 % Identity |
|---|---|---|---|
| MSNNNYSNGLNPDESLSASAFDPNLVGPTLPPIPPFTLPTG | 1 | 100% | 100% |
| MSEKYIILHGTALEPNLIGPTLPPIPPFTFPNG | 3 | 81.3% | 90.9% |
| MVKVEGNGGKSKIKSPLNSNFKILSDLVGPTFPPVPTGMTGIT | 5 | 50.0% | 72.7% |
| MKQNDKLVWLDKGIIGPENIGPTFPVLPPIHPTG | 7 | 43.8% | 54.5% |
| MDEFLSSAALNPGSVGPTLPPMQPFQFRTG | 9 | 62.5% | 72.7% |
| MFDKNEIQKINGILQANALNPNLIGPTLPPIPPFTLPTG | 11 | 81.3% | 90.9% |
| MFDKNEMKKTNEVLQANALDPNIIGPTLPPIPPFTLPTG | 13 | 81.3% | 81.8% |
| MSRKDKFNRSRMSRKDRFNSPKIKSEISISPDLVGPTFPPIPSFTLPTG | 15 | 62.5% | 81.8% |
| MNEEYSILHGPALEPNLIGPTLPSIPPFTFPTG | 17 | 75.0% | 81.8% |
| MKNRDNNRKQNSLSSNFRIPPELIGPTFPPVPTGFTGIG | 19 | 50.0% | 63.6% |
| MSDKHQMKKISEVLQAHALDPNLIGPLLPPITPFTFPTG | 21 | 75.0% | 72.7% |
| MDEFLSFAALNPGSIGPTLPPVPPFQFPTG | 23 | 62.5% | 72.7% |
| MDEFLSSTALNPCSIGPTLPPMQPFQFPTG | 25 | 56.2% | 63.6% |
| MKERDRQNSLNSNFRISPNLIGPTFPPVPTGFTGIG | 27 | 56.2% | 63.6% |
| VFDKNEIQKINGILQANALNPNLIGPTLPIPPFTLPTG | 29 | 81.3% | 90.9% |
| MDEFLYFAALNPGSIGPTLPPVQPFQFPTG | 31 | 56.2% | 63.6% |
| MDSKNIGPTFPPLPSINFPTG | 33 | 43.8% | 54.5% |
| MIGPENIGPTFPILPPIYIPTG | 35 | 43.8% | 54.5% |
| MSNNNIPSPFFFNNFNPELIGPTFPPIPPLTLPTG | 43 | 68.8% | 81.8% |
| MFSEKKRKDLIPDNFLSAPALDPNLIGPTFPPIPSFTLPTG | 45 | 75.0% | 72.7% |
| MTRKDKFNRSRISRRDRFNSPKIKSEILISPDLVGPTFPPIPSFTLPTG | 47 | 62.5% | 81.8% |
| MSRKDRFNSPKIKSEISISPDLVGPTFPPIPSFTLPTG | 49 | 62.5% | 81.8% |
| MKERDNKGKQHSLNSNFRIPPELIGPTFPPVPTGFTGIG | 51 | 50.0% | 63.6% |
| MRERDNKRQHSLNPNFRISPELIGPTFPPVPTGFTGIG | 53 | 50.0% | 63.6% |
| MKNRDNKGKQQSNFRIPPELIGPTFPPVPTGFTGIG | 55 | 50.0% | 63.6% |
| MKFSKKSTVDSSIVGKRVVSKVNILRFYDARSCQDKDVDGFVDVGELFTIFRKLNMEGSVQFKAHNSIGKTYYITINEVYVFVTVLLQYSTLIGGSYVFDKNEIQKINGILQANALNPNLIGPTLPPIPPFTLPTG | 57 | 81.3% | 90.9% |

COMPOSITIONS COMPRISING RECOMBINANT BACILLUS CELLS AND ANOTHER BIOLOGICAL CONTROL AGENT

CROSS REFERENCE TO RELATED APPLICATIONS

This application is a continuation of U.S. patent application Ser. No. 17/813,065, filed Jul. 18, 2022, which is a continuation of U.S. patent application Ser. No. 16/857,448, filed 24 Apr. 2020, which is a continuation of U.S. patent application Ser. No. 15/511,822, which is a 35 U.S.C. § 371 national phase entry of PCT/US2015/050592, filed on 17 Sep. 2015, which claims priority to U.S. Provisional Application No. 62/051,911, filed 17 Sep. 2014; the contents of all of the aforementioned application are hereby incorporated herein by reference in their entirety.

REFERENCE TO SEQUENCE LISTING SUBMITTED ELECTRONICALLY

The Sequence Listing, which is a part of the present disclosure, is submitted concurrently with the specification as an XML file. The name of the file containing the Sequence Listing is "181332C_SeqListing.XML", which was created on Sep. 11, 2023 and is 119,825 bytes in size. The subject matter of the Sequence Listing is incorporated herein in its entirety by reference.

BACKGROUND

Field of the Invention

The present invention relates to a composition comprising (i) recombinant exosporium-producing *Bacillus* cells that express a fusion protein comprising: (x) at least one plant growth stimulating protein or peptide; and (y) a targeting sequence that localizes the fusion protein to the exosporium of the *Bacillus* cells; and (ii) at least one further biological control agent selected from particular microorganisms disclosed herein and/or a mutant of a specific strain of a microorganism disclosed herein having all identifying characteristics of the respective strain, and/or at least one metabolite produced by the respective strain that exhibits the ability to improve plant growth and/or health and/or activity against insects, mites, nematodes and/or phytopathogens in a synergistically effective amounts. Furthermore, the present invention relates to the use of this composition as well as a method for enhancing plant growth, promoting plant health, and/or reducing overall damage of plants and plant parts.

Background of the Invention

In crop protection, there is a continuous need for applications that improve the health and/or the growth of plants. Healthier plants generally result in higher yields and/or better quality of a plant or its products.

In order to promote plant health, fertilizers are employed worldwide, based on both inorganic and organic substances. A fertilizer may be a single substance or a composition, and is used to provide nutrients to plants. A major breakthrough in the application of fertilizers was the development of nitrogen-based fertilizer by Justus von Liebig around 1840. Fertilizers, however, can lead to soil acidification and destabilization of nutrient balance in soil, including depletion of minerals and enrichment of salt and heavy metals. In addition, excessive fertilizer use can lead to alteration of soil fauna as well as contaminate surface water and ground water. Further, unhealthful substances such as nitrate may become enriched in plants and fruits.

In addition, insecticides and fungicide are employed worldwide to control pests. Synthetic insecticides or fungicides often are non-specific and therefore can act on organisms other than the target organisms, including other naturally occurring beneficial organisms. Because of their chemical nature, they may also be toxic and non-biodegradable. Consumers worldwide are increasingly conscious of the potential environmental and health problems associated with the residuals of chemicals, particularly in food products. This has resulted in growing consumer pressure to reduce the use or at least the quantity of chemical (i.e., synthetic) pesticides. Thus, there is a need to manage food chain requirements while still allowing effective pest control.

A further problem arising with the use of synthetic insecticides or fungicides is that the repeated and exclusive application of an insecticide or fungicides often leads to selection of resistant animal pests or microorganisms. Normally, such strains are also cross-resistant against other active ingredients having the same mode of action. An effective control of the pathogens with said active compounds is then not possible any longer. However, active ingredients having new mechanisms of action are difficult and expensive to develop.

The use of biological control agents (BCAs) is an alternative to fertilizers and synthetic pesticides. In some cases, the effectiveness of BCAs is not at the same level as for fertilizers or for conventional insecticides and fungicides, especially in case of severe infection pressure. Consequently, in some circumstances, biological control agents, their mutants and metabolites produced by them are, in particular in low application rates, not entirely satisfactory. Thus, there is a constant need for developing new, alternative plant health-enhancing and/or plant protection agents which in some areas at least help to fulfill the above-mentioned requirements.

SUMMARY

In view of this, it was in particular an object of the present invention to provide compositions which have an enhanced ability to improve plant growth and/or to enhance plant health or which exhibit enhanced activity against insects, mites, nematodes and/or phytopathogens.

Accordingly, it was found that these objectives are achieved with the compositions according to the invention as defined in the following. By applying a) recombinant exosporium-producing *Bacillus* cells that express a fusion protein comprising: (i) at least one plant growth stimulating protein or peptide selected from the group consisting of an enzyme involved in the production or activation of a plant growth stimulating compound; an enzyme that degrades or modifies a bacterial, fungal, or plant nutrient source; and a protein or peptide that protects a plant from a pathogen or a pest; and (ii) a targeting sequence that localizes the fusion protein to the exosporium of the *Bacillus* cells; and b) at least one particular strain disclosed herein other than said recombinant *Bacillus* cells according to the invention, the ability to enhance preferably in a superadditive manner (i) plant growth, plant yield and/or plant health and/or (ii) the activity against insects, mites, nematodes and/or phytopathogens.

References herein to targeting sequences, exosporium proteins, exosporium protein fragments, fusion proteins, and recombinant exosporium producing *Bacillus* cells that express such fusion proteins should not be considered to be stand-alone embodiments. Instead, throughout the present application, references to the targeting sequences, exosporium proteins, exosporium protein fragments, fusion proteins, and recombinant exosporium producing *Bacillus* cells that express such fusion proteins should be considered to be disclosed and claimed only in combination (and preferably in a synergistic combination) with one or more of the particular biological control agents described herein. Furthermore, references to "the particular microorganisms disclosed herein" or "to the particular biological control agents described, or disclosed, herein" are intended to encompass the biological control agents and the microorganisms, including the strains, mutants and metabolites thereof, as described below under the headings "Synthetic Nodulation Factors and Plant Growth Simulators" and "Additional Biological Control Agents".

The present invention is directed to a composition comprising a) recombinant exosporium-producing *Bacillus* cells that express a fusion protein comprising: (i) at least one plant growth stimulating protein or peptide selected from the group consisting of an enzyme involved in the production or activation of a plant growth stimulating compound and an enzyme that degrades or modifies a bacterial, fungal, or plant nutrient source or a protein or peptide that protects a plant from a pathogen; and (ii) a targeting sequence that localizes the fusion protein to the exosporium of the *Bacillus* cells; and b) at least one further and different particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in synergistically effective amounts.

In some embodiments, the targeting sequence comprises an amino acid sequence having at least about 43% identity with amino acids 20-35 of SEQ ID NO: 1, wherein the identity with amino acids 25-35 is at least about 54%; a targeting sequence comprising amino acids 1-35 of SEQ ID NO: 1; a targeting sequence comprising amino acids 20-35 of SEQ ID NO: 1; a targeting sequence comprising amino acids 22-31 of SEQ ID NO: 1; a targeting sequence comprising amino acids 22-33 of SEQ ID NO: 1; a targeting sequence comprising amino acids 20-31 of SEQ ID NO: 1; a targeting sequence comprising SEQ ID NO: 1; or an exosporium protein comprising an amino acid sequence having at least 85% identity with SEQ ID NO: 2.

In other embodiments, the recombinant *Bacillus* cells are cells of a *Bacillus cereus* family member such as *Bacillus anthracis, Bacillus cereus, Bacillus thuringiensis, Bacillus mycoides, Bacillus pseudomycoides, Bacillus samanii, Bacillus gaemokensis, Bacillus weihenstephensis, Bacillus toyoiensis* and combinations thereof. In a further embodiment, the recombinant *Bacillus* cells are cells of *Bacillus thuringiensis* BT013A.

In certain aspects, the fusion protein comprises an enzyme involved in the production or activation of a plant growth stimulating compound selected from the group consisting of an acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase, a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5' ribonucleotide phosphohydrolase, an adenosine nucleosidase, a zeatin cis-trans isomerase, a zeatin O-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosanase, a chitinase, a β-1,3-glucanase, a β-1,4-glucanase, a β-1,6-glucanase, an aminocyclopropane-1-carboxylic acid deaminase, and an enzyme involved in producing a nod factor.

In other aspects, the fusion protein comprises an enzyme that degrades or modifies a bacterial, fungal, or plant nutrient source selected from the group consisting of a cellulase, a lipase, a lignin oxidase, a protease, a glycoside hydrolase, a phosphatase, a nitrogenase, a nuclease, an amidase, a nitrate reductase, a nitrite reductase, an amylase, an ammonia oxidase, a ligninase, a glucosidase, a phospholipase, a phytase, a pectinase, a glucanase, a sulfatase, a urease, a xylanase, and a siderophore.

In some embodiments, the fusion protein is expressed under the control of a sporulation promoter native to the targeting sequence, exosporium protein, or exosporium protein fragment of the fusion protein. The fusion protein may be expressed under the control of a high-expression sporulation promoter. In certain aspects, the high-expression sporulation promoter comprises a sigma-K sporulation-specific polymerase promoter sequence. In other aspects, the sporulation promoter comprises a nucleic acid sequence having at least 80% identity, at least 85% identity, at least 90% identity, at least 95% identity, at least 96% identity, at least 97% identity, at least 98% identity, or at least 99% identity with a nucleic acid sequence of any one of SEQ ID NOS: 85-103. In some embodiments, the sporulation promoter comprises a nucleic acid sequence having 100% identity with a nucleic acid sequence of any one of SEQ ID NOS: 85-103.

In other embodiments, the at least one biological control agent is a *Bacillus subtilis* or *Bacillus amyloliquefaciens* strain that produces a fengycin or plipastatin-type compound, an iturin-type compound, and/or a surfactin-type compound. For background, see the following review article: Ongena, M., et al., "*Bacillus* Lipopeptides: Versatile Weapons for Plant Disease Biocontrol," Trends in Microbiology, Vol 16, No. 3, March 2008, pp. 115-125. *Bacillus* strains capable of producing lipopeptides include *Bacillus subtilis* QST713, *Bacillus amyloliquefaciens* strain D747 (available as BACSTAR® from Etec Crop Solutions, NZ and also available as DOUBLE NICKEL™ from Certis, US); *Bacillus subtilis* MBI600 (available as SUBTILEX® from Becker Underwood, US EPA Reg. No. 71840-8); *Bacillus subtilis* Y1336 (available as BIOBAC® WP from Bion-Tech, Taiwan, registered as a biological fungicide in Taiwan under Registration Nos. 4764, 5454, 5096 and 5277); *Bacillus amyloliquefaciens*, in particular strain FZB42 (available as RHIZOVITAL® from ABITEP, DE); and *Bacillus subtilis* var. *amyloliquefaciens* FZB24 is available from Novozymes Biologicals Inc. (Salem, Virginia) or Syngenta Crop Protection, LLC (Greensboro, North Carolina) as the fungicide TAEGRO® or TAEGRO® ECO (EPA Registration No. 70127-5).

In still other embodiments, the at least one biological control agent is selected from the group consisting of *Bacillus pumilus* strain QST2808, *Bacillus subtilis* strain QST713, *Bacillus subtilis* strain QST30002, *Bacillus subtilis* strain QST30004, *Streptomyces microflavus* strain NRRL B-50550, *Streptomyces microflavus* strain M, *Bacillus firmus* strain I-1582, mutants thereof having all the identifying characteristics of the respective strains, and at least one metabolite produced by the respective strains that exhibits activity against insects, mites, nematodes and/or phytopathogens.

In some embodiments, the composition of the present invention comprises a) recombinant exosporium-producing *Bacillus* cells that express a fusion protein comprising: (i) at least one plant growth stimulating protein or peptide selected from the group consisting of an enzyme involved in the production or activation of a plant growth stimulating compound and an enzyme that degrades or modifies a bacterial, fungal, or plant nutrient source; or a protein or peptide that protects a plant from a pathogen; and (ii) a targeting sequence that localizes the fusion protein to the exosporium of the *Bacillus* cells; and b) *Bacillus firmus* strain I-1582 in a synergistically effective amount.

In some embodiments, the composition of the present invention comprises a) recombinant exosporium-producing *Bacillus* cells that express a fusion protein comprising: (i) at least one plant growth stimulating protein or peptide selected from the group consisting of an enzyme involved in the production or activation of a plant growth stimulating compound and an enzyme that degrades or modifies a bacterial, fungal, or plant nutrient source or at least one protein or peptide that protects a plant from a pathogen; and (ii) a targeting sequence that localizes the fusion protein to the exosporium of the *Bacillus* cells; and b) *Bacillus subtilis* strain QST713 in a synergistically effective amount.

In some embodiments, the composition of the present invention comprises a) recombinant exosporium-producing *Bacillus* cells that express a fusion protein comprising: (i) at least one plant growth stimulating protein or peptide selected from the group consisting of an enzyme involved in the production or activation of a plant growth stimulating compound and an enzyme that degrades or modifies a bacterial, fungal, or plant nutrient source or at least one protein or peptide that protects a plant from a pathogen; and (ii) a targeting sequence that localizes the fusion protein to the exosporium of the *Bacillus* cells; and b) *Bacillus pumilus* strain QST2808 in a synergistically effective amount.

In yet other embodiments, the composition further comprises c) at least one fungicide and/or d) at least one insecticide. The at least one fungicide and/or the at least one insecticide may be synthetic. In one aspect of such embodiment, the biological control agent and additional insecticide of such composition comprise *Bacillus firmus* strain I-1582 and clothianidin, respectively.

In a particular aspect of the above embodiments (i) the biological control agent is *Bacillus subtilis* QST713 or mutants having all the identifying characteristics of the *Bacillus subtilis* QST713 and/or at least 95% or at least 98% sequence identity to *Bacillus subtilis* QST713; (ii) the targeting sequence comprises an amino acid sequence having at least about 43% identity with amino acids 20-35 of SEQ ID NO: 1, wherein the identity with amino acids 25-35 is at least about 54%; (iii) the plant growth stimulating protein or peptide comprises endoglucanase, phospholipase or chitosinase, preferably with at least 95% sequence identity to SEQ ID NO: 107, 108 and 109, respectively; and (iv) the recombinant *Bacillus cereus* family member cells comprise cells of *Bacillus thuringiensis* or *Bacillus mycoides*. In yet another particular embodiment, the recombinant *Bacillus cereus* family member cells are cells of *Bacillus thuringiensis* BT013A.

In a particular aspect of the above embodiments (i) the biological control agent is *Bacillus firmus* I-1582 or mutants having all the identifying characteristics of *Bacillus firmus* I-1582 and/or at least 95% or at least 98% sequence identity to *Bacillus firmus* 1-1582; (ii) the targeting sequence comprises an amino acid sequence having at least about 43% identity with amino acids 20-35 of SEQ ID NO: 1, wherein the identity with amino acids 25-35 is at least about 54%; (iii) the plant growth stimulating protein or peptide comprises endoglucanase, phospholipase or chitosinase, preferably with at least 95% or at least 98% sequence identity to SEQ ID NO: 107, 108 and 109, respectively; and (iv) the recombinant *Bacillus cereus* family member cells comprise cells of *Bacillus thuringiensis* or *Bacillus mycoides*. In yet another particular embodiment, the recombinant *Bacillus cereus* family member cells are cells of *Bacillus thuringiensis* BT013A. In yet another aspect of this embodiment the composition further comprises clothianidin.

In a particular aspect of the above embodiments (i) the biological control agent is *Bacillus pumilus* QST2808 or mutants having all the identifying characteristics of *Bacillus pumilus* QST2808 and/or at least 95% or at least 98% sequence identity to *Bacillus pumilus* QST2808; (ii) the targeting sequence comprises an amino acid sequence having at least about 43% identity with amino acids 20-35 of SEQ ID NO: 1, wherein the identity with amino acids 25-35 is at least about 54%; (iii) the plant growth stimulating protein or peptide comprises endoglucanase, phospholipase or chitosinase, preferably with at least 95% or at least 98% sequence identity to SEQ ID NO: 107, 108 and 109, respectively; and (iv) the recombinant *Bacillus cereus* family member cells comprise the cells of *Bacillus thuringiensis* or *Bacillus mycoides*. In yet another particular embodiment, the recombinant *Bacillus cereus* family member cells are cells of *Bacillus thuringiensis* BT013A.

In some aspects, the composition further comprises at least one auxiliary selected from the group consisting of extenders, solvents, spontaneity promoters, carriers, emulsifiers, dispersants, frost protectants, thickeners and adjuvants.

In other aspects, the invention is directed to a seed treated with any of the compositions disclosed herein.

Furthermore, the present invention relates to use of the disclosed compositions as a fungicide and/or insecticide. In certain aspects, the disclosed compositions are used for reducing overall damage of plants and plant parts as well as losses in harvested fruits or vegetables caused by insects, mites, nematodes and/or phytopathogens. In other aspects, the disclosed compositions are used for enhancing plant growth and/or promoting plant health.

Additionally, the present invention is directed to a method of treating a plant, a plant part, such as a seed, root, rhizome, corm, bulb, or tuber, and/or a locus on which or near which the plant or the plant parts grow, such as soil, to enhance plant growth and/or promote plant health comprising the step of simultaneously or sequentially applying to a plant, a plant part and/or a plant loci: a) recombinant exosporium-producing *Bacillus* cells that express a fusion protein comprising: (i) at least one plant growth stimulating protein or peptide selected from the group consisting of an enzyme involved in the production or activation of a plant growth stimulating compound; an enzyme that degrades or modifies a bacterial, fungal, or plant nutrient source; and a protein or peptide that protects a plant from a pathogen; and (ii) a targeting sequence that localizes the fusion protein to the exosporium of the *Bacillus* cells; and b) at least one biological control agent disclosed herein and/or a mutant of a specific strain of a microorganism disclosed herein having all identifying characteristics of the respective strain, and/or at least one metabolite produced by the respective strain, and/or at least one metabolite produced by the respective strain that exhibits activity against insects, mites, nematodes and/or phytopathogens in a synergistically effective amount.

In another embodiment, the present invention is a method for reducing overall damage of plants and plant parts as well as losses in harvested fruits or vegetables caused by insects, mites, nematodes and/or phytopathogens comprising the step of simultaneously or sequentially applying to a plant, a plant part, such as a seed, root, rhizome, corm, bulb, or tuber, and/or a locus on which or near which the plant or the plant parts grow, such as soil: a) recombinant exosporium-producing *Bacillus* cells that express a fusion protein comprising: (i) at least one plant growth stimulating protein or peptide selected from the group consisting of an enzyme involved in the production or activation of a plant growth stimulating compound; an enzyme that degrades or modifies a bacterial, fungal, or plant nutrient source; and a protein or peptide that protects a plant from a pathogen; and (ii) a targeting sequence that localizes the fusion protein to the exosporium of the *Bacillus* cells; and b) at least one biological control agent disclosed herein and/or a mutant of a specific strain of a microorganism disclosed herein having all identifying characteristics of the respective strain, and/or at least one metabolite produced by the respective strain, and/or at least one metabolite produced by the respective strain that exhibits activity against insects, mites, nematodes and/or phytopathogens in a synergistically effective amount.

In the above paragraphs, the term "comprise" or any derivative thereof (e.g., comprising, comprises) may be replaced with "consist of" or the applicable corresponding derivative thereof.

BRIEF DESCRIPTION OF THE DRAWINGS

FIG. 1 shows an alignment of the amino acid sequence of the amino-terminal portion of *Bacillus anthracis* Sterne strain BclA and with the corresponding region from various exosporium proteins from *Bacillus cereus* family members.

DETAILED DESCRIPTION

In general "pesticidal" means the ability of a substance to increase mortality or inhibit the growth rate of plant pests. The term is used herein, to describe the property of a substance to exhibit activity against insects, mites, nematodes and/or phytopathogens. In the sense of the present invention the term "pests" include insects, mites, nematodes and/or phytopathogens.

As used herein, "biological control" is defined as control of a pathogen and/or insect and/or an acarid and/or a nematode by the use of a second organism. Known mechanisms of biological control include bacteria that control root rot by out-competing fungi for space or nutrients on the surface of the root. Bacterial toxins, such as antibiotics, have been used to control pathogens. The toxin can be isolated and applied directly to the plant or the bacterial species may be administered so it produces the toxin in situ. Other means of exerting biological control include the application of certain fungi producing ingredients active against a target phytopathogen, insect, mite or nematode, or attacking the target pest/pathogen. "Biological control" as used in connection with the present invention may also encompass microorganisms having a beneficial effect on plant health, growth, vigor, stress response or yield. Application routes include spray application, soil application and seed treatment.

The term "metabolite" refers to any compound, substance or byproduct of a fermentation of a said microorganism that has pesticidal, fungicidal or nematicidal activity or ability to enhance plant health or increase plant yield. The term "mutant" refers to a variant of the parental strain as well as methods for obtaining a mutant or variant in which the pesticidal activity is greater than that expressed by the parental strain. The "parent strain" is defined herein as the original strain before mutagenesis or the deposited strain. To obtain such mutants the parental strain may be treated with a chemical such as N-methyl-N'-nitro-N-nitrosoguanidine, ethylmethanesulfone, or by irradiation using gamma, x-ray, or UV-irradiation, or by other means well known to those skilled in the art.

A "variant" is a strain having all the identifying characteristics of the NRRL or ATCC Accession Numbers as indicated in this text and can be identified as having a genome that hybridizes under conditions of high stringency to the genome of the NRRL or ATCC Accession Numbers.

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. Hybridization reactions can be performed under conditions of different "stringency". In general, a low stringency hybridization reaction is carried out at about 40° C. in 10×SSC or a solution of equivalent ionic strength/temperature. A moderate stringency hybridization is typically performed at about 50° C. in 6×SSC, and a high stringency hybridization reaction is generally performed at about 60° C. in 1×SSC.

A variant of the indicated NRRL or ATCC Accession Number may also be defined as a strain having a genomic sequence that is greater than 85%, more preferably greater than 90% or more preferably greater than 95% sequence identity to the genome of the indicated NRRL or ATCC Accession Number. A polynucleotide or polynucleotide region (or a polypeptide or polypeptide region) has a certain percentage (for example, 80%, 85%, 90%, 95%, 96%, 97%, 98% or 99%) of "sequence identity" to another sequence means that, when aligned, that percentage of bases (or amino acids) are the same in comparing the two sequences. This alignment and the percent homology or sequence identity can be determined using software programs known in the art, for example, those described in Current Protocols in Molecular Biology (F. M. Ausubel et al., eds., 1987) Supplement 30, Section 7. 7. 18, Table 7. 7. 1.

NRRL is the abbreviation for the Agricultural Research Service Culture Collection, having the address National Center for Agricultural Utilization Research, Agricultural Research Service, U.S. Department of Agriculture, 1815 North University Street, Peoria, Illinois 61604, U.S.A.

ATCC is the abbreviation for the American Type Culture Collection, having the address ATCC Patent Depository, 10801 University Boulevard, Manassas, Virginia 10110, U.S.A.

CNCM is the abbreviation for the Collection Nationale de Cultures de Microorganismes, Institute Pasteur, France, having the address of Institut Pasteur, 25 Rue du Docteur Roux, F-75724 Paris Cedex 15, France.

All strains described herein and having an accession number in which the prefix is NRRL, ATCC or CNCM have been deposited with the above-described respective depositary institution in accordance with the Budapest Treaty on the International Recognition of the Deposit of Microorganisms for the Purposes of Patent Procedure.

An "enzyme involved in the production or activation of a plant growth stimulating compound" includes any enzyme that catalyzes any step in a biological synthesis pathway for a compound that stimulates plant growth or alters plant structure, or any enzyme that catalyzes the conversion of an inactive or less active derivative of a compound that stimulates plant growth or alters plant structure to an active or more active form of the compound. Such compounds include, for example, but are not limited to, small molecule plant hormones such as auxins and cytokinins, bioactive peptides, and small plant growth stimulating molecules synthesized by bacteria or fungi in the rhizosphere (e.g., 2,3-butanediol).

A "plant immune system enhancer protein or peptide" as used herein includes any protein or peptide that has a beneficial effect on the immune system of a plant.

The term "plant growth stimulating protein or peptide" as used herein includes any protein or peptide that increases plant growth in a plant exposed to the protein or peptide.

The terms "promoting plant growth" and "stimulating plant growth" are used interchangeably herein, and refer to the ability to enhance or increase at least one of the plant's height, weight, leaf size, root size, or stem size, to increase protein yield from the plant or to increase grain yield of the plant.

A "protein or peptide that protects a plant from a pathogen" as used herein includes any protein or peptide that makes a plant exposed to the protein or peptide less susceptible to infection with a pathogen.

A "protein or peptide that enhances stress resistance in a plant" as used herein includes any protein or peptide that makes a plant exposed to the protein or peptide more resistant to stress.

The term "plant binding protein or peptide" refers to any peptide or protein capable of specifically or non-specifically binding to any part of a plant (e.g., roots or aerial portions of a plant such as leaves foliage, stems, flowers, or fruits) or to plant matter.

The term "targeting sequence" as used herein refers to a polypeptide sequence that results in the localization of a longer polypeptide or the protein to the exosporium of a *Bacillus cereus* family member.

Recombinant Exosporium-Producing *Bacillus* Cells Expressing Fusion Proteins

The fusion proteins contain a targeting sequence, an exosporium protein, or an exosporium protein fragment that targets the fusion protein to the exosporium of a *Bacillus cereus* family member and: (a) a plant growth stimulating protein or peptide; (b) a protein or peptide that protects a plant from a pathogen; (c) a protein or peptide that enhances stress resistance of a plant; (d) a plant binding protein or peptide; or (e) a plant immune system enhancer protein or peptide. When expressed in *Bacillus cereus* family member bacteria, these fusion proteins are targeted to the exosporium layer of the spore and are physically oriented such that the protein or peptide is displayed on the outside of the spore.

This *Bacillus* exosporium display (BEMD) system can be used to deliver peptides, enzymes, and other proteins to plants (e.g., to plant foliage, fruits, flowers, stems, or roots) or to a plant growth medium such as soil. Peptides, enzymes, and proteins delivered to the soil or another plant growth medium in this manner persist and exhibit activity in the soil for extended periods of time. Introduction of recombinant exosporium-producing *Bacillus* cells expressing the fusion proteins described herein into soil or the rhizosphere of a plant leads to a beneficial enhancement of plant growth in many different soil conditions. The use of the BEMD to create these enzymes allows them to continue to exert their beneficial results to the plant and the rhizosphere over the first months of a plants life.

Targeting Sequences, Exosporium Proteins, and Exosporium Protein Fragments

For ease of reference, the SEQ ID NOS. for the peptide and protein sequences referred to herein are listed in Table 1 below.

TABLE 1

Peptide and Protein Sequences

| Protein, Protein Fragment, or Targeting Sequence | Sequence Identification Number |
|---|---|
| AA 1-41 of BclA (*B. anthracis* Sterne) | SEQ ID NO: 1* |
| Full length BclA | SEQ ID NO: 2* |
| AA 1-33 of BetA/BAS3290 (*B. anthracis* Sterne) | SEQ ID NO: 3 |
| Full length BetA/BAS3290 | SEQ ID NO: 4 |
| Met + AA 2-43 of BAS4623 (*B. anthracis* Sterne) | SEQ ID NO: 5 |
| Full length BAS4623 | SEQ ID NO: 6 |
| AA 1-34 of BclB (*B. anthracis* Sterne) | SEQ ID NO: 7 |
| Full length BclB | SEQ ID NO: 8 |
| AA 1-30 of BAS1882 (*B. anthracis* Sterne) | SEQ ID NO: 9 |
| Full length BAS1882 | SEQ ID NO: 10 |
| AA 1-39 of gene 2280 (*B. weihenstephensis* KBAB4) | SEQ ID NO: 11 |
| Full length KBAB4 gene 2280 | SEQ ID NO: 12 |
| AA 1-39 of gene 3572 (*B. weihenstephensis* KBAB4) | SEQ ID NO: 13 |
| Full Length KBAB4 gene 3572 | SEQ ID NO: 14 |
| AA 1-49 of Exosporium Leader Peptide (*B. cereus* VD200) | SEQ ID NO: 15 |
| Full Length Exosporium Leader Peptide | SEQ ID NO: 16 |
| AA 1-33 of Exosporium Leader Peptide (*B. cereus* VD166) | SEQ ID NO: 17 |
| Full Length Exosporium Leader Peptide | SEQ ID NO: 18 |
| AA 1-39 of hypothetical protein IKG_04663 (*B. cereus* VD200) | SEQ ID NO: 19 |
| Full Length hypothetical protein IKG_04663, partial | SEQ ID NO: 20 |
| AA 1-39 of YVTN β- propeller protein (*B. weihenstephensis* KBAB4) | SEQ ID NO: 21 |

TABLE 1-continued Peptide and Protein Sequences

| Protein, Protein Fragment, or Targeting Sequence | Sequence Identification Number |
|---|---|
| Full length YVTN β- propeller protein KBAB4 | SEQ ID NO: 22 |
| AA 1-30 of hypothetical protein bcerkbab4_2363 (*B. weihenstephensis* KBAB4) | SEQ ID NO: 23 |
| Full length hypothetical protein bcerkbab4_2363 KBAB4 | SEQ ID NO: 24 |
| AA 1-30 of hypothetical protein bcerkbab4_2131 (*B. weihenstephensis* KBAB4) | SEQ ID NO: 25 |
| Full length hypothetical protein bcerkbab4_2131 | SEQ ID NO: 26 |
| AA 1-36 of triple helix repeat containing collagen (*B. weihenstephensis* KBAB4) | SEQ ID NO: 27 |
| Full length triple helix repeat-containing collagen KBAB4 | SEQ ID NO: 28 |
| AA 1-39 of hypothetical protein bmyco0001_21660 (*B. mycoides* 2048) | SEQ ID NO: 29 |
| Full length hypothetical protein bmyco0001_21660 | SEQ ID NO: 30 |
| AA 1-30 of hypothetical protein bmyc0001_22540 (*B. mycoides* 2048) | SEQ ID NO: 31 |
| Full length hypothetical protein bmyc0001_22540 | SEQ ID NO: 32 |
| AA 1-21 of hypothetical protein bmyc0001_21510 (*B. mycoides* 2048) | SEQ ID NO: 33 |
| Full length hypothetical protein bmyc0001_21510 | SEQ ID NO: 34 |
| AA 1-22 of collagen triple helix repeat protein (*B. thuringiensis* 35646) | SEQ ID NO: 35 |

TABLE 1-continued

Peptide and Protein Sequences

| Protein, Protein Fragment, or Targeting Sequence | Sequence Identification Number |
|---|---|
| Full length BclC (*B. anthracis* Sterne) | SEQ ID NO: 82 |
| Full length acid phosphatase (*Bacillus thuringiensis* serovar konkukian str. 97-27) | SEQ ID NO: 83 |
| Full length InhA2 (*B. thuringiensis* HD74) | SEQ ID NO: 84 |

AA = amino acids

*B. anthracis Sterne strain BclA has 100% sequence identity with B. thuringiensis BclA. Thus, SEQ ID NOS: 1, 2, and 59 also represent amino acids 1-41 of B. thuringiensis BclA, full length B. thuringiensis BclA, and amino acids 1-196 of B. thuringiensis BclA, respectively. Likewise, SEQ ID NO: 60 also represents a methionine residue plus amino acids 20-35 of B. thuringiensis BclA.
**B. mycoides hypothetical protein TIGR03720 has 100% sequence identity with B. mycoides hypothetical protein WP003189234. Thus, SEQ ID NOs: 57 and 58 also represent amino acids 1-136 of B. mycoides hypothetical protein WP003189234 and full length B. mycoides hypothetical protein WP003189234, respectively.

*Bacillus* is a genus of rod-shaped bacteria. The *Bacillus cereus* family of bacteria includes the species *Bacillus anthracis, Bacillus cereus, Bacillus thuringiensis, Bacillus mycoides, Bacillus pseudomycoides, Bacillus samanii, Bacillus gaemokensis, Bacillus toyoiensis* and *Bacillus weihenstephensis*. Under stressful environmental conditions, *Bacillus cereus* family bacteria undergo sporulation and form oval endospores that can stay dormant for extended periods of time. The outermost layer of the endospores is known as the exosporium and comprises a basal layer surrounded by an external nap of hair-like projections. Filaments on the hair-like nap are predominantly formed by the collagen-like glycoprotein BclA, while the basal layer is comprised of a number of different proteins. Another collagen-related protein, BclB, is also present in the exosporium and exposed on endospores of *Bacillus cereus* family members.

BclA, the major constituent of the surface nap, has been shown to be attached to the exosporium with its amino-terminus (N-terminus) positioned at the basal layer and its carboxy-terminus (C-terminus) extending outward from the spore.

It was previously discovered that certain sequences from the N-terminal regions of BclA and BclB could be used to target a peptide or protein to the exosporium of a *Bacillus cereus* endospore (see U.S. Patent Publication Nos. 2010/0233124 and 2011/0281316, and Thompson, et al., "Targeting of the BclA and BclB Proteins to the *Bacillus anthracis* Spore Surface," Molecular Microbiology, 70(2):421-34 (2008), the entirety of each of which is hereby incorporated by reference). It was also found that the BetA/BAS3290 protein of *Bacillus anthracis* localized to the exosporium.

In particular, amino acids 20-35 of BclA from *Bacillus anthracis* Sterne strain have been found to be sufficient for targeting to the exosporium. A sequence alignment of amino acids 1-41 of BclA (SEQ ID NO: 1) with the corresponding N-terminal regions of several other *Bacillus cereus* family exosporium proteins and *Bacillus cereus* family proteins having related sequences is shown in FIG. 1. As can be seen from FIG. 1, there is a region of high-homology among all of the proteins in the region corresponding to amino acids 20-41 of BclA. However, in these sequences, the amino acids corresponding to amino acids 36-41 of BclA contain secondary structure and are not necessary for fusion protein localization to the exosporium. The conserved targeting sequence region of BclA (amino acids 20-35 of SEQ ID NO: 1) is shown in bold in FIG. 1 and corresponds to the minimal targeting sequence needed for localization to the exosporium. A more highly conserved region spanning amino acids 25-35 of BclA within the targeting sequence is underlined in the sequences in FIG. 1, and is the recognition sequence for ExsFA/BxpB/ExsFB and homologs, which direct and assemble the described proteins on the surface of the exosporium The amino acid sequences of SEQ ID NOS: 3, 5, and 7 in FIG. 1 are amino acids 1-33 of *Bacillus anthracis* Sterne strain BetA/BAS3290, a methionine followed by amino acids 2-43 of *Bacillus anthracis* Sterne strain BAS4623, and amino acids 1-34 of *Bacillus anthracis* Sterne strain BclB, respectively. (For BAS4623, it was found that replacing the valine present at position 1 in the native protein with a methionine resulted in better expression.) As can be seen from FIG. 1, each of these sequences contains a conserved region corresponding to amino acids 20-35 of BclA (SEQ ID NO: 1; shown in bold), and a more highly conserved region corresponding to amino acids 20-35 of BclA (underlined).

Additional proteins from *Bacillus cereus* family members also contain the conserved targeting region. In particular, in FIG. 1, SEQ ID NO: 9 is amino acids 1-30 of *Bacillus anthracis* Sterne strain BAS1882, SEQ ID NO: 11 is amino acids 1-39 of the *Bacillus weihenstephensis* KBAB4 2280 gene product, SEQ ID NO: 13 is amino acids 1-39 of the *Bacillus weihenstephensis* KBAB4 3572 gene product, SEQ ID NO: 15 is amino acids 1-49 of *Bacillus cereus* VD200 exosporium leader peptide, SEQ ID NO: 17 is amino acids 1-33 of *Bacillus cereus* VD166 exosporium leader peptide, SEQ ID NO: 19 is amino acids 1-39 of *Bacillus cereus* VD200 hypothetical protein IKG_04663, SEQ ID NO: 21 is amino acids 1-39 of *Bacillus weihenstephensis* KBAB4 YVTN β-propeller protein, SEQ ID NO: 23 is amino acids 1-30 of *Bacillus weihenstephensis* KBAB4 hypothetical protein bcerkbab4_2363, SEQ ID NO: 25 is amino acids 1-30 of *Bacillus weihenstephensis* KBAB4 hypothetical protein bcerkbab4_2131, SEQ ID NO: 27 is amino acids 1-36 of *Bacillus weihenstephensis* KBAB4 triple helix repeat containing collagen, SEQ ID NO: 29 is amino acids 1-39 of *Bacillus mycoides* 2048 hypothetical protein bmyco0001_21660, SEQ ID NO: 31 is amino acids 1-30 of *Bacillus mycoides* 2048 hypothetical protein bmyc0001_22540, SEQ ID NO: 33 is amino acids 1-21 of *Bacillus mycoides* 2048 hypothetical protein bmyc0001_21510, SEQ ID NO: 35 is amino acids 1-22 of *Bacillus thuringiensis* 35646 collagen triple helix repeat protein, SEQ ID NO: 43 is amino acids 1-35 of *Bacillus cereus* hypothetical protein WP_69652, SEQ ID NO: 45 is amino acids 1-41 of *Bacillus cereus* exosporium leader WP016117717, SEQ ID NO: 47 is amino acids 1-49 of *Bacillus cereus* exosporium peptide WP002105192, SEQ ID NO: 49 is amino acids 1-38 of *Bacillus cereus* hypothetical protein WP87353, SEQ ID NO: 51 is amino acids 1-39 of Bacillus cereus exosporium peptide 02112369, SEQ ID NO: 53 is amino acids 1-39 of Bacillus cereus exosporium protein WP016099770, SEQ ID NO: 55 is amino acids 1-36 of Bacillus thuringiensis hypothetical protein YP006612525, and SEQ ID NO: 57 is amino acids 1-136 of Bacillus mycoides hypothetical protein TIGR03720. As shown in FIG. 1, each of the N-terminal regions of these proteins contains a region that is conserved with amino acids 20-35 of BclA (SEQ ID NO: 1), and a more highly conserved region corresponding to amino acids 25-35 of BclA.

Any portion of BclA which includes amino acids 20-35 can be used as the targeting sequence. In addition, full-length exosporium proteins or exosporium protein fragments can be used for targeting the fusion proteins to the exosporium. Thus, full-length BclA or a fragment of BclA that includes amino acids 20-35 can be used for targeting to the exosporium. For example, full length BclA (SEQ ID NO: 2) or a midsized fragment of BclA that lacks the carboxy-terminus such as SEQ ID NO: 59 (amino acids 1-196 of BclA) can be used to target the fusion proteins to the exosporium. Midsized fragments such as the fragment of SEQ ID NO: 59 have less secondary structure than full length BclA and have been found to be suitable for use as a targeting sequence. The targeting sequence can also comprise much shorter portions of BclA which include amino acids 20-35, such as SEQ ID NO: 1 (amino acids 1-41 of BclA), amino acids 1-35 of SEQ ID NO: 1, amino acids 20-35 of SEQ ID NO: 1, or SEQ ID NO: 60 (a methionine residue linked to amino acids 20-35 of BclA). Even shorter fragments of BclA which include only some of amino acids 20-35 also exhibit the ability to target fusion proteins to the exosporium. For example, the targeting sequence can comprise amino acids 22-31 of SEQ ID NO: 1, amino acids 22-33 of SEQ ID NO: 1, or amino acids 20-31 of SEQ ID NO: 1.

Alternatively, any portion of BetA/BAS3290, BAS4623, BclB, BAS1882, the KBAB4 2280 gene product, the KBAB4 3572 gene product, B. cereus VD200 exosporium leader peptide, B. cereus VD166 exosporium leader peptide, B. cereus VD200 hypothetical protein IKG_04663, B. weihenstephensis KBAB4 YVTN β-propeller protein, B. weihenstephensis KBAB4 hypothetical protein bcerkbab4_2363, B. weihenstephensis KBAB4 hypothetical protein bcerkbab4_2131, B. weihenstephensis KBAB4 triple helix repeat containing collagen, B. mycoides 2048 hypothetical protein bmyco0001_21660, B. mycoides 2048 hypothetical protein bmyc0001_22540, B. mycoides 2048 hypothetical protein bmyc0001_21510, B. thuringiensis 35646 collagen triple helix repeat protein, B. cereus hypothetical protein WP_69652, B. cereus exosporium leader WP016117717, B. cereus exosporium peptide WP002105192, B. cereus hypothetical protein WP87353, B. cereus exosporium peptide 02112369, B. cereus exosporium protein WP016099770, B. thuringiensis hypothetical protein YP006612525, or B. mycoides hypothetical protein TIGR03720, which includes the amino acids corresponding to amino acids 20-35 of BclA can serve as the targeting sequence. As can be seen from FIG. 1, amino acids 12-27 of BetA/BAS3290, amino acids 23-38 of BAS4623, amino acids 13-28 of BclB, amino acids 9-24 of BAS1882, amino acids 18-33 of KBAB4 2280 gene product, amino acids 18-33 of KBAB4 3572 gene product, amino acids 28-43 of B. cereus VD200 exosporium leader peptide, amino acids 12-27 of B. cereus VD166 exosporium leader peptide, amino acids 18-33 of B. cereus VD200 hypothetical protein IKG_04663, amino acids 18-33 B. weihenstephensis KBAB4 YVTN β-propeller protein, amino acids 9-24 of B. weihenstephensis KBAB4 hypothetical protein bcerkbab4_2363, amino acids 9-24 of B. weihenstephensis KBAB4 hypothetical protein bcerkbab4_2131, amino acids 15-30 of B. weihenstephensis KBAB4 triple helix repeat containing collagen, amino acids 18-33 of B. mycoides 2048 hypothetical protein bmyco0001_21660, amino acids 9-24 of B. mycoides 2048 hypothetical protein bmyc0001_22540, amino acids 1-15 of B. mycoides 2048 hypothetical protein bmyc0001_21510, amino acids 1-16 of B. thuringiensis 35646 collagen triple helix repeat protein, amino acids 14-29 of B. cereus hypothetical protein WP_69652, amino acids 20-35 of B. cereus exosporium leader WP016117717, amino acids 28-43 of B. cereus exosporium peptide WP002105192, amino acids 17-32 of B. cereus hypothetical protein WP87353, amino acids 18-33 of B. cereus exosporium peptide 02112369, amino acids 18-33 of B. cereus exosporium protein WP016099770, amino acids 15-30 of B. thuringiensis hypothetical protein YP006612525, and amino acids 115-130 of B. mycoides hypothetical protein TIGR03720 correspond to amino acids 20-35 of BclA. Thus, any portion of these proteins that includes the above-listed corresponding amino acids can serve as the targeting sequence.

Furthermore, any amino acid sequence comprising amino acids 20-35 of BclA, or any of the above-listed corresponding amino acids can serve as the targeting sequence.

Thus, the targeting sequence can comprise amino acids 1-35 of SEQ ID NO: 1, amino acids 20-35 of SEQ ID NO: 1, SEQ ID NO: 1, SEQ ID NO: 60, amino acids 22-31 of SEQ ID NO: 1, amino acids 22-33 of SEQ ID NO: 1, or amino acids 20-31 of SEQ ID NO: 1. Alternatively, the targeting sequence consists of amino acids 1-35 of SEQ ID NO: 1, amino acids 20-35 of SEQ ID NO: 1, SEQ ID NO: 1, or SEQ ID NO: 60. Alternatively, the targeting sequence can consist of amino acids 22-31 of SEQ ID NO: 1, amino acids 22-33 of SEQ ID NO: 1, or amino acids 20-31 of SEQ ID NO: 1. Alternatively, the exosporium protein can comprise full length BclA (SEQ ID NO: 2), or the exosporium protein fragment can comprise a midsized fragment of BclA that lacks the carboxy-terminus, such as SEQ ID NO: 59 (amino acids 1-196 of BclA). Alternatively, the exosporium protein fragment can consist of SEQ ID NO: 59.

The targeting sequence can also comprise amino acids 1-27 of SEQ ID NO: 3, amino acids 12-27 of SEQ ID NO: 3, or SEQ ID NO: 3, or the exosporium protein can comprise full length BetA/BAS3290 (SEQ ID NO: 4). It has also been found that a methionine residue linked to amino acids 12-27 of BetA/BAS3290 can be used as a targeting sequence. Thus, the targeting sequence can comprise SEQ ID NO: 61. The targeting sequence can also comprise amino acids 14-23 of SEQ ID NO: 3, amino acids 14-25 of SEQ ID NO: 3, or amino acids 12-23 of SEQ ID NO: 3.

The targeting sequence can also comprise amino acids 1-38 of SEQ ID NO: 5, amino acids 23-38 of SEQ ID NO: 5, or SEQ ID NO: 5, or the exosporium protein can comprise full length BAS4623 (SEQ ID NO: 6).

Alternatively, the targeting sequence can comprise amino acids 1-28 of SEQ ID NO: 7, amino acids 13-28 of SEQ ID NO: 7, or SEQ ID NO: 7, or the exosporium protein can comprise full length BclB (SEQ ID NO: 8).

The targeting sequence can also comprise amino acids 1-24 of SEQ ID NO: 9, amino acids 9-24 of SEQ ID NO: 9, or SEQ ID NO: 9, or the exosporium protein can comprise full length BAS1882 (SEQ ID NO: 10). A methionine residue linked to amino acids 9-24 of BAS1882 can also be used as a targeting sequence. Thus, the targeting sequence can comprise SEQ ID NO: 69.

The targeting sequence can also comprise amino acids 1-33 of SEQ ID NO: 11, amino acids 18-33 of SEQ ID NO: 11, or SEQ ID NO: 11, or the exosporium protein can comprise the full length *B. weihenstephensis* KBAB4 2280 gene product (SEQ ID NO: 12). A methionine residue linked to amino acids 18-33 of the *B. weihenstephensis* KBAB4 2280 gene product can also be used as a targeting sequence. Thus, the targeting sequence can comprise SEQ ID NO: 62.

The targeting sequence can also comprise amino acids 1-33 of SEQ ID NO: 13, amino acids 18-33 of SEQ ID NO: 13, or SEQ ID NO: 13, or the exosporium protein can comprise the full length *B. weihenstephensis* KBAB4 3572 gene product (SEQ ID NO:14). A methionine residue linked to amino acids 18-33 of the *B. weihenstephensis* KBAB4 3572 gene product can also be used as a targeting sequence. Thus, the targeting sequence can comprise SEQ ID NO: 63.

Alternatively, the targeting sequence can comprise amino acids 1-43 of SEQ ID NO: 15, amino acids 28-43 of SEQ ID NO: 15, or SEQ ID NO: 15, or the exosporium protein can comprise full length *B. cereus* VD200 exosporium leader peptide (SEQ ID NO: 16).

The targeting sequence can also comprise amino acids 1-27 of SEQ ID NO: 17, amino acids 12-27 of SEQ ID NO: 17, or SEQ ID NO: 17, or the exosporium protein can comprise full-length *B. cereus* VD166 exosporium leader peptide (SEQ ID NO: 18). A methionine residue linked to amino acids 12-27 of the *B. cereus* VD166 exosporium leader peptide can also be used as a targeting sequence. Thus, the targeting sequence can comprise SEQ ID NO: 64.

The targeting sequence can also comprise amino acids 1-33 of SEQ ID NO: 19, amino acids 18-33 of SEQ ID NO: 19, or SEQ ID NO: 19, or the exosporium protein can comprise full length *B. cereus* VD200 hypothetical protein IKG_04663 (SEQ ID NO: 20).

Alternatively, the targeting sequence comprises amino acids 1-33 of SEQ ID NO: 21, amino acids 18-33 of SEQ ID NO: 21, or SEQ ID NO: 21, or the exosporium protein can comprise full length *B. weihenstephensis* KBAB4 YVTN β-propeller protein (SEQ ID NO: 22). A methionine residue linked to amino acids 18-33 of the *B. weihenstephensis* KBAB4 YVTN β-propeller protein can also be used as a targeting sequence. Thus, the targeting sequence can comprise SEQ ID NO: 65.

The targeting sequence can also comprise amino acids 1-24 of SEQ ID NO: 23, amino acids 9-24 of SEQ ID NO: 23, or SEQ ID NO: 23, or the exosporium protein can comprise full length *B. weihenstephensis* KBAB4 hypothetical protein bcerkbab4_2363 (SEQ ID NO: 24). A methionine residue linked to amino acids 9-24 of *B. weihenstephensis* KBAB4 hypothetical protein bcerkbab4_2363 can also be used as a targeting sequence. Thus, the targeting sequence can comprise SEQ ID NO: 66.

The targeting sequence comprise amino acids 1-24 of SEQ ID NO: 25, amino acids 9-24 of SEQ ID NO: 25, or SEQ ID NO: 25, or the exosporium protein can comprise full length *B. weihenstephensis* KBAB4 hypothetical protein bcerkbab4_2131 (SEQ ID NO: 26). A methionine residue linked to amino acids 9-24 of *B. weihenstephensis* KBAB4 hypothetical protein bcerkbab4_2131 can also be used as a targeting sequence. Thus, the targeting sequence can comprise SEQ ID NO: 67.

Alternatively, the targeting sequence comprises amino acids 1-30 of SEQ ID NO: 27, amino acids 15-30 of SEQ ID NO: 27, or SEQ ID NO: 27, or the exosporium protein can comprise full length *B. weihenstephensis* KBAB4 triple helix repeat containing collagen (SEQ ID NO: 28).

The targeting sequence can also comprise amino acids 1-33 of SEQ ID NO: 29, amino acids 18-33 of SEQ ID NO: 29, or SEQ ID NO: 29, or the exosporium protein can comprise full length *B. mycoides* 2048 hypothetical protein bmyco0001_21660 (SEQ ID NO:30).

The targeting sequence can also comprise amino acids 1-24 of SEQ ID NO: 31, amino acids 9-24 of SEQ ID NO: 31, or SEQ ID NO:31, or the exosporium protein can comprise full length *B. mycoides* 2048 hypothetical protein bmyc0001_22540 (SEQ ID NO:32). A methionine residue linked to amino acids 9-24 of *B. mycoides* 2048 hypothetical protein bmyc0001_22540 can also be used as a targeting sequence. Thus, the targeting sequence can comprise SEQ ID NO: 68.

Alternatively, the targeting sequence comprises amino acids 1-15 of SEQ ID NO: 33, SEQ ID NO: 33, or the exosporium protein comprises full length *B. mycoides* 2048 hypothetical protein bmyc0001_21510 (SEQ ID NO: 34).

The targeting sequence can also comprise amino acids 1-16 of SEQ ID NO: 35, SEQ ID NO: 35, or the exosporium protein can comprise full length *B. thuringiensis* 35646 collagen triple helix repeat protein (SEQ ID NO:36).

The targeting sequence can comprise amino acids 1-29 of SEQ ID NO: 43, amino acids 14-29 of SEQ ID NO: 43, or SEQ ID NO: 43, or the exosporium protein can comprise full length *B. cereus* hypothetical protein WP_69652 (SEQ ID NO: 44).

Alternatively, the targeting sequence can comprise amino acids 1-35 of SEQ ID NO: 45, amino acids 20-35 of SEQ ID NO: 45, or SEQ ID NO: 45, or the exosporium protein can comprise full length *B. cereus* exosporium leader WP016117717 (SEQ ID NO: 46). A methionine residue linked to amino acids 20-35 of *B. cereus* exosporium leader WP016117717 can also be used as a targeting sequence. Thus, the targeting sequence can comprise SEQ ID NO: 70.

The targeting sequence can comprise amino acids 1-43 of SEQ ID NO: 47, amino acids 28-43 of SEQ ID NO: 47, or SEQ ID NO: 47, or the exosporium protein can comprise full length *B. cereus* exosporium peptide WP002105192 (SEQ ID NO: 48).

The targeting sequence can comprise amino acids 1-32 of SEQ ID NO: 49, amino acids 17-32 of SEQ ID NO: 49, or SEQ ID NO: 49, or the exosporium protein can comprise full length *B. cereus* hypothetical protein WP87353 (SEQ ID NO: 50).

Alternatively, the targeting sequence can comprise amino acids 1-33 of SEQ ID NO: 51, amino acids 18-33 of SEQ ID NO: 51, or SEQ ID NO: 51, or the exosporium protein can comprise full length *B. cereus* exosporium peptide 02112369 (SEQ ID NO: 52).

The targeting sequence can comprise amino acids 1-33 of SEQ ID NO: 53, amino acids 18-33 of SEQ ID NO: 53, or SEQ ID NO: 53, or the exosporium protein can comprise full length *B. cereus* exosporium protein WP016099770 (SEQ ID NO: 54).

Alternatively, the targeting sequence can comprise acids 1-30 of SEQ ID NO: 55, amino acids 15-30 of SEQ ID NO: 55, or SEQ ID NO: 55, or the exosporium protein can comprise full length *B. thuringiensis* hypothetical protein YP006612525 (SEQ ID NO: 56).

The targeting sequence can also comprise amino acids 1-130 of SEQ ID NO: 57, amino acids 115-130 of SEQ ID NO: 57, or SEQ ID NO: 57, or the exosporium protein can comprise full length *B. mycoides* hypothetical protein TIGR03720 (SEQ ID NO: 58).

In addition, it can readily be seen from the sequence alignment in FIG. 1 that while amino acids 20-35 of BclA are conserved, and amino acids 25-35 are more conserved, some degree of variation can occur in this region without affecting the ability of the targeting sequence to target a protein to the exosporium. FIG. 1 lists the percent identity of each of corresponding amino acids of each sequence to amino acids 20-35 of BclA ("20-35% Identity") and to amino acids 25-35 of BclA ("25-35% Identity"). Thus, for example, as compared to amino acids 20-35 of BclA, the corresponding amino acids of BetA/BAS3290 are about 81.3% identical, the corresponding amino acids of BAS4623 are about 50.0% identical, the corresponding amino acids of BclB are about 43.8% identical, the corresponding amino acids of BAS1882 are about 62.5% identical, the corresponding amino acids of the KBAB4 2280 gene product are about 81.3% identical, and the corresponding amino acids of the KBAB4 3572 gene product are about 81.3% identical. The sequence identities over this region for the remaining sequences are listed in FIG. 1.

With respect to amino acids 25-35 of BclA, the corresponding amino acids of BetA/BAS3290 are about 90.9% identical, the corresponding amino acids of BAS4623 are about 72.7% identical, the corresponding amino acids of BclB are about 54.5% identical, the corresponding amino acids of BAS1882 are about 72.7% identical, the corresponding amino acids of the KBAB4 2280 gene product are about 90.9% identical, and the corresponding amino acids of the KBAB4 3572 gene product are about 81.8% identical. The sequence identities over this region for the remaining sequences are listed in FIG. 1.

Thus, the targeting sequence can comprise an amino acid sequence having at least about 43% identity with amino acids 20-35 of SEQ ID NO: 1, wherein the identity with amino acids 25-35 is at least about 54%. Alternatively, the targeting sequence consists of an amino acid sequence consisting of 16 amino acids and having at least about 43% identity with amino acids 20-35 of SEQ ID NO: 1, wherein the identity with amino acids 25-35 is at least about 54%.

The targeting sequence can also comprise an amino acid sequence having at least about 50% identity with amino acids 20-35 of SEQ ID NO: 1, wherein the identity with amino acids 25-35 is at least about 63%. Alternatively the targeting sequence consists of an amino acid sequence consisting of 16 amino acids and having at least about 50% identity with amino acids 20-35 of SEQ ID NO: 1, wherein the identity with amino acids 25-35 is at least about 63%.

The targeting sequence can also comprise an amino acid sequence having at least about 50% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 50% identity with amino acids 20-35 of SEQ ID NO: 1, wherein the identity with amino acids 25-35 is at least about 72%.

The targeting sequence can also comprise an amino acid sequence having at least about 56% identity with amino acids 20-35 of SEQ ID NO: 1, wherein the identity with amino acids 25-35 is at least about 63%. Alternatively, the targeting sequence consists of an amino acid sequence consisting of 16 amino acids and having at least about 56% identity with amino acids 20-35 of SEQ ID NO: 1, wherein the identity with amino acids 25-35 is at least about 63%.

Alternatively, the targeting sequence can comprise an amino sequence having at least about 62% identity with amino acids 20-35 of SEQ ID NO: 1, wherein the identity with amino acids 25-35 is at least about 72%. The targeting sequence can also consist of an amino acid sequence consisting of 16 amino acids and having at least about 62% identity with amino acids 20-35 of SEQ ID NO: 1, wherein the identity with amino acids 25-35 of SEQ ID NO: 1 is at least about 72%.

The targeting sequence can comprise an amino acid sequence having at least 68% identity with amino acids 20-35 of SEQ ID NO: 1, wherein the identity with amino acids 25-35 is at least about 81%. Alternatively, the targeting sequence consists of an amino acid sequence consisting of 16 amino acids and having at least 68% identity with amino acids 20-35 of SEQ ID NO: 1, wherein the identity with amino acids 25-35 is at least about 81%.

The targeting sequence can also comprise an amino sequence having at least about 75% identity with amino acids 20-35 of SEQ ID NO: 1, wherein the identity with amino acids 25-35 is at least about 72%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO: 1 is at least about 72%.

The targeting sequence can also comprise an amino sequence having at least about 75% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 75% identity with amino acids 20-35 of SEQ ID NO: 1, wherein the identity with amino acids 25-35 of SEQ ID NO: 1 is at least about 81%.

The targeting sequence can also comprise an amino acid sequence having at least about 81% identity with amino acids 20-35 of SEQ ID NO: 1, wherein the identity with amino acids 25-35 is at least about 81%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 81%.

The targeting sequence can comprise an amino acid sequence having at least about 81% identity with amino acids 20-35 of SEQ ID NO: 1, wherein the identity with amino acids 25-35 is at least about 90%. Alternatively, the targeting sequence consists of an amino acid sequence consisting of 16 amino acids and having at least about 81% identity with amino acids 20-35 of SEQ ID NO: 1, wherein the identity with amino acids 25-35 is at least about 90%.

The skilled person will recognize that variants of the above sequences can also be used as targeting sequences, so long as the targeting sequence comprises amino acids 20-35 of BclA, the corresponding amino acids of BetA/BAS3290, BAS4263, BclB, BAS1882, the KBAB4 2280 gene product, or the KBAB 3572 gene product, or a sequence comprising any of the above noted sequence identities to amino acids 20-35 and 25-35 of BclA is present.

It has further been discovered that certain *Bacillus cereus* family exosporium proteins which lack regions having homology to amino acids 25-35 of BclA can also be used to target a peptide or protein to the exosporium of a *Bacillus cereus* family member. In particular, the fusion proteins can comprise an exosporium protein comprising SEQ ID NO: 71 (*B. mycoides* InhA), an exosporium protein comprising SEQ ID NO: 72 (*B. anthracis* Sterne BAS1141 (ExsY)), an exosporium protein comprising SEQ ID NO: 73 (*B. anthracis* Sterne BAS1144 (BxpB/ExsFA)), an exosporium protein comprising SEQ ID NO: 74 (*B. anthracis* Sterne BAS1145 (CotY)), an exosporium protein comprising SEQ ID NO: 75 (*B. anthracis* Sterne BAS1140), an exosporium protein comprising SEQ ID NO: 76 (*B. anthracis* H9401 ExsFB), an exosporium protein comprising SEQ ID NO: 77 (*B. thuringiensis* HD74 InhA1), an exosporium protein comprising SEQ ID NO: 78 (*B. cereus* ATCC 10876 ExsJ), an exosporium protein comprising SEQ ID NO: 79 (*B. cereus* ExsH), an exosporium protein comprising SEQ ID NO: 80 (*B. anthracis* Ames YjcA), an exosporium protein comprising SEQ ID NO: 81 (*B. anthracis* YjcB), an exosporium protein comprising SEQ ID NO: 82 (*B. anthracis* Sterne BclC), an exosporium protein comprising SEQ ID NO: 83 (*Bacillus thuringiensis* serovar konkukian str. 97-27 acid phosphatase), or an exosporium protein comprising SEQ ID NO: 84 (*B. thuringiensis* HD74 InhA2). Inclusion of an exosporium protein comprising SEQ ID NO: 71, 72, 73, 74, 75, 76, 77, 78, 79, 80, 81, 82, 83, or 84 in the fusion proteins described herein will result in targeting to the exosporium of a *B. cereus* family member.

Moreover, exosporium proteins having a high degree of sequence identity with any of the full-length exosporium proteins or the exosporium protein fragments described above can also be used to target a peptide or protein to the exosporium of a *Bacillus cereus* family member. Thus, the fusion protein can comprise an exosporium protein comprising an amino acid sequence having at least 85% identity with any one of SEQ ID NOS: 2, 4, 6, 8, 10, 12, 14, 16, 18, 20, 22, 24, 26, 28, 30, 32, 34, 36, 44, 46, 48, 50, 52, 54, 56, 58, 59, 71, 72, 73, 74, 75, 76, 77, 78, 79, 80, 81, 82, 83, and 84. Alternatively, the fusion protein can comprise an exosporium protein having at least 90%, at least 95%, at least 98%, at least 99%, or 100% identity with any one of SEQ ID NOS: 2, 4, 6, 8, 10, 12, 14, 16, 18, 20, 22, 24, 26, 28, 30, 32, 34, 36, 44, 46, 48, 50, 52, 54, 56, 58, 59, 71, 72, 73, 74, 75, 76, 77, 78, 79, 80, 81, 82, 83, and 84.

Alternatively, the fusion protein can comprise an exosporium protein fragment consisting of an amino acid sequence having at least 85% identity with SEQ ID NO: 59. Alternatively, the fusion protein can comprise an exosporium protein fragment consisting of an amino acid sequence having at least 90%, at least 95%, at least 98%, at least 99%, or 100% identity with SEQ ID NO: 59.

In any of the targeting sequences, exosporium proteins, or exosporium protein fragments described herein, the targeting sequence, exosporium protein, or exosporium protein fragment can comprise the amino acid sequence GXT at its carboxy terminus, wherein X is any amino acid.

In any of the targeting sequences, exosporium proteins, and exosporium protein fragments described herein, the targeting sequence, exosporium protein, or exosporium protein fragment, can comprise an alanine residue at the position of the targeting sequence that corresponds to amino acid 20 of SEQ ID NO: 1.

Fusion Proteins

The fusion proteins can comprise a targeting sequence, an exosporium protein, or an exosporium protein fragment, and at least one plant growth stimulating protein or peptide. The plant growth stimulating protein or peptide can comprise a peptide hormone, a non-hormone peptide, an enzyme involved in the production or activation of a plant growth stimulating compound or an enzyme that degrades or modifies a bacterial, fungal, or plant nutrient source. The targeting sequence, exosporium protein, or exosporium protein fragment can be any of the targeting sequences, exosporium proteins, or exosporium protein fragments described above.

The fusion proteins can comprise a targeting sequence, an exosporium protein, or an exosporium protein fragment, and at least one protein or peptide that protects a plant from a pathogen. The targeting sequence, exosporium protein, or exosporium protein fragment can be any of the targeting sequences, exosporium proteins, or exosporium protein fragments described above.

The fusion protein can be made using standard cloning and molecular biology methods known in the art. For example, a gene encoding a protein or peptide (e.g., a gene encoding a plant growth stimulating protein or peptide) can be amplified by polymerase chain reaction (PCR) and ligated to DNA coding for any of the above-described targeting sequences to form a DNA molecule that encodes the fusion protein. The DNA molecule encoding the fusion protein can be cloned into any suitable vector, for example a plasmid vector. The vector suitably comprises a multiple cloning site into which the DNA molecule encoding the fusion protein can be easily inserted. The vector also suitably contains a selectable marker, such as an antibiotic resistance gene, such that bacteria transformed, transfected, or mated with the vector can be readily identified and isolated. Where the vector is a plasmid, the plasmid suitably also comprises an origin of replication. The DNA encoding the fusion protein is suitably under the control of a sporulation promoter which will cause expression of the fusion protein on the exosporium of a *B. cereus* family member endospore (e.g., a native bclA promoter from a *B. cereus* family member). Alternatively, DNA coding for the fusion protein can be integrated into the chromosomal DNA of the *B. cereus* family member host.

The fusion protein can also comprise additional polypeptide sequences that are not part of the targeting sequence, exosporium protein, exosporium protein fragment, or the plant growth stimulating protein or peptide, the protein or peptide that protects a plant from a pathogen, the protein or peptide that enhances stress resistance in a plant, or the plant binding protein or peptide. For example, the fusion protein can include tags or markers to facilitate purification or visualization of the fusion protein (e.g., a polyhistidine tag or a fluorescent protein such as GFP or YFP) or visualization of recombinant exosporium-producing *Bacillus* cells spores expressing the fusion protein.

Expression of fusion proteins on the exosporium using the targeting sequences, exosporium proteins, and exosporium protein fragments described herein is enhanced due to a lack of secondary structure in the amino-termini of these sequences, which allows for native folding of the fused proteins and retention of activity. Proper folding can be further enhanced by the inclusion of a short amino acid linker between the targeting sequence, exosporium protein, exosporium protein fragment, and the fusion partner protein.

Thus, any of the fusion proteins described herein can comprise an amino acid linker between the targeting sequence, the exosporium protein, or the exosporium protein fragment and the plant growth stimulating protein or peptide, the protein or peptide that protects a plant from a pathogen, the protein or peptide that enhances stress resistance in a plant, or the plant binding protein or peptide.

The linker can comprise a polyalanine linker or a polyglycine linker. A linker comprising a mixture of both alanine and glycine residues can also be used. For example, where the targeting sequence comprises SEQ ID NO: 1, a fusion protein can have one of the following structures:

No linker: SEQ ID NO: 1—Fusion Partner Protein

Alanine Linker: SEQ ID NO: 1—An-Fusion Partner Protein

Glycine Linker: SEQ ID NO: 1—Gn-Fusion Partner Protein

Mixed Alanine and Glycine Linker: SEQ ID NO: 1—(A/G)n-Fusion Partner Protein where An, Gn, and (A/G)n are any number of alanines, any number of glycines, or any number of a mixture of alanines and glycines, respectively. For example, n can be 1 to 25, and is preferably 6 to 10. Where the linker comprises a mixture of alanine and glycine residues, any combination of glycine and alanine residues can be used. In the above structures, "Fusion Partner Protein" represents the plant growth stimulating protein or peptide, the protein or peptide that protects a plant from a pathogen, the protein or peptide that enhances stress resistance in a plant, or the plant binding protein or peptide.

Alternatively or in addition, the linker can comprise a protease recognition site. Inclusion of a protease recognition site allows for targeted removal, upon exposure to a protease that recognizes the protease recognition site, of the plant growth stimulating protein or peptide, the protein or peptide that protects a plant from a pathogen, the protein or peptide that enhances stress resistance in a plant, or the plant binding protein or peptide.

Plant Growth Stimulating Proteins and Peptides

As noted above, the fusion proteins can comprise a targeting sequence, exosporium protein, or exosporium protein fragment and at least one plant growth stimulating protein or peptide. For example, the plant growth stimulating protein or peptide can comprise a peptide hormone, a non-hormone peptide, an enzyme involved in the production or activation of a plant growth stimulating compound, or an enzyme that degrades or modifies a bacterial, fungal, or plant nutrient source.

For example, where the plant growth stimulating protein or peptide comprises a peptide hormone, the peptide hormone can comprise a phytosulfokine (e.g., phytosulfokine-α), clavata 3 (CLV3), systemin, ZmIGF, or a SCR/SP11.

Where the plant growth stimulating protein or peptide comprises a non-hormone peptide, the non-hormone peptide can comprise a RKN 16D10, Hg-Syv46, an eNOD40 peptide, melittin, mastoparan, Mas7, RHPP, POLARIS, or kunitz trypsin inhibitor (KTI).

The plant growth stimulating protein or peptide can comprise an enzyme involved in the production or activation of a plant growth stimulating compound. The enzyme involved in the production or activation of a plant growth stimulating compound can be any enzyme that catalyzes any step in a biological synthesis pathway for a compound that stimulates plant growth or alters plant structure, or any enzyme that catalyzes the conversion of an inactive or less active derivative of a compound that stimulates plant growth or alters plant structure into an active or more active form of the compound.

The plant growth stimulating compound can comprise a compound produced by bacteria or fungi in the rhizosphere, e.g., 2,3-butanediol.

Alternatively, the plant growth stimulating compound can comprise a plant growth hormone, e.g., a cytokinin or a cytokinin derivative, ethylene, an auxin or an auxin derivative, a gibberellic acid or a gibberellic acid derivative, abscisic acid or an abscisic acid derivative, or a jasmonic acid or a jasmonic acid derivative.

Where the plant growth stimulating compound comprises a cytokinin or a cytokinin derivative, the cytokinin or the cytokinin derivative can comprise kinetin, cis-zeatin, trans-zeatin, 6-benzylaminopurine, dihydroxyzeatin, N6-(D2-isopentenyl) adenine, ribosylzeatin, N6-(D2-isopentenyl) adenosine, 2-methylthio-cis-ribosylzeatin, cis-ribosylzeatin, trans-ribosylzeatin, 2-methylthio-trans-ribosylzeatin, ribosylzeatin-5-monosphosphate, N6-methylaminopurine, N6-dimethylaminopurine, 2'-deoxyzeatin riboside, 4-hydroxy-3-methyl-trans-2-butenylaminopurine, ortho-topolin, meta-topolin, benzyladenine, ortho-methyltopolin, meta-methyltopolin, or a combination thereof.

Where the plant growth stimulating compound comprises an auxin or an auxin derivative, the auxin or the auxin derivative can comprise an active auxin, an inactive auxin, a conjugated auxin, a naturally occurring auxin, or a synthetic auxin, or a combination thereof. For example, the auxin or auxin derivative can comprise indole-3-acetic acid, indole-3-pyruvic acid, indole-3-acetaldoxime, indole-3-acetamide, indole-3-acetonitrile, indole-3-ethanol, indole-3-pyruvate, indole-3-acetaldoxime, indole-3-butyric acid, a phenylacetic acid, 4-chloroindole-3-acetic acid, a glucose-conjugated auxin, or a combination thereof.

The enzyme involved in the production or activation of a plant growth stimulating compound can comprise an acetoin reductase, an indole-3-acetamide hydrolase, a tryptophan monooxygenase, an acetolactate synthetase, an α-acetolactate decarboxylase, a pyruvate decarboxylase, a diacetyl reductase, a butanediol dehydrogenase, an aminotransferase (e.g., tryptophan aminotransferase), a tryptophan decarboxylase, an amine oxidase, an indole-3-pyruvate decarboxylase, an indole-3-acetaldehyde dehydrogenase, a tryptophan side chain oxidase, a nitrile hydrolase, a nitrilase, a peptidase, a protease, an adenosine phosphate isopentenyltransferase, a phosphatase, an adenosine kinase, an adenine phosphoribosyltransferase, CYP735A, a 5' ribonucleotide phosphohydrolase, an adenosine nucleosidase, a zeatin cis-trans isomerase, a zeatin O-glucosyltransferase, a β-glucosidase, a cis-hydroxylase, a CK cis-hydroxylase, a CK N-glucosyltransferase, a 2,5-ribonucleotide phosphohydrolase, an adenosine nucleosidase, a purine nucleoside phosphorylase, a zeatin reductase, a hydroxylamine reductase, a 2-oxoglutarate dioxygenase, a gibberellic 2B/3B hydrolase, a gibberellin 3-oxidase, a gibberellin 20-oxidase, a chitosinase, a chitinase, a β-1,3-glucanase, a β-1,4-glucanase, a β-1,6-glucanase, an aminocyclopropane-1-carboxylic acid deaminase, or an enzyme involved in producing a nod factor (e.g., nodA, nodB, or nodI).

Where the enzyme comprises a protease or peptidase, the protease or peptidase can be a protease or peptidase that cleaves proteins, peptides, proproteins, or preproproteins to create a bioactive peptide. The bioactive peptide can be any peptide that exerts a biological activity.

Examples of bioactive peptides include RKN 16D10 and RHPP.

The protease or peptidase that cleaves proteins, peptides, proproteins, or preproproteins to create a bioactive peptide can comprise subtilisin, an acid protease, an alkaline protease, a proteinase, an endopeptidase, an exopeptidase, thermolysin, papain, pepsin, trypsin, pronase, a carboxylase, a serine protease, a glutamic protease, an aspartate protease, a cysteine protease, a threonine protease, or a metalloprotease.

The protease or peptidase can cleave proteins in a protein-rich meal (e.g., soybean meal or yeast extract).

The plant growth stimulating protein can also comprise an enzyme that degrades or modifies a bacterial, fungal, or plant nutrient source. Such enzymes include cellulases, lipases, lignin oxidases, proteases, glycoside hydrolases, phosphatases, nitrogenases, nucleases, amidases, nitrate reductases, nitrite reductases, amylases, ammonia oxidases, ligninases, glucosidases, phospholipases, phytases, pectinases, glucanases, sulfatases, ureases, xylanases, and siderophores. When introduced into a plant growth medium or applied to a plant, seed, or an area surrounding a plant or a plant seed, fusion proteins comprising enzymes that degrade or modify a bacterial, fungal, or plant nutrient source can aid in the processing of nutrients in the vicinity of the plant and result in enhanced uptake of nutrients by the plant or by beneficial bacteria or fungi in the vicinity of the plant.

Suitable cellulases include endocellulases (e.g., an endogluconase such as a *Bacillus subtilis* endoglucanase, a *Bacillus thuringiensis* endoglucanase, a *Bacillus cereus* endoglucanase, or a *Bacillus clausii* endoglucanase), exocellulases (e.g., a *Trichoderma reesei* exocellulase), and β-glucosidases (e.g., a *Bacillus subtilis* β-glucosidase, a *Bacillus thuringiensis* β-glucosidase, a *Bacillus cereus* β-glucosidase, or a *Bacillus clausii* β-glucosidase).

The lipase can comprise a *Bacillus subtilis* lipase, a *Bacillus thuringiensis* lipase, a *Bacillus cereus* lipase, or a *Bacillus clausii* lipase.

In one embodiment, the lipase comprises a *Bacillus subtilis* lipase. The *Bacillus subtilis* lipase can be PCR amplified using the following primers: ggatccatggctgaacacaatcc (forward, SEQ ID NO: 37) and ggatccttaattcgtattctggcc (reverse, SEQ ID NO: 38).

In another embodiment, the cellulase is a *Bacillus subtilis* endoglucanase. The *Bacillus subtilis* endoglucanase can be PCR amplified using the following primers: ggatccatgaaacggtcaatc (forward, SEQ ID NO: 39) and ggatccttactaatttggttctgt (reverse, SEQ ID NO: 40).

In yet another embodiment, the fusion protein comprises an *E. coli* protease PtrB. The *E. coli* protease PtrB can be PCR amplified using the following primers: ggatccatgctaccaaaagcc (forward, SEQ ID NO: 41) and ggatccttagtccgcaggcgtagc (reverse, SEQ ID NO: 42).

In certain embodiments, the fusion protein contains an endoglucanase which derives from the nucleotide sequence in SEQ ID NO: 104.

The amino acid sequence for an exemplary endoglucanase that may be fused to the targeting sequence, an exosporium protein, or an exosporium protein fragment and, optionally, a linker sequence, such as a poly-A linker, is the fusion protein provided as SEQ ID NO: 107.

In other embodiments, the fusion protein contains a phospholipase that derives from the nucleotide sequence set forth in SEQ ID NO: 105.

The amino acid sequence for an exemplary phospholipase that may be fused to the targeting sequence, an exosporium protein, or an exosporium protein fragment and, optionally, a linker sequence, such as a poly-A linker, is the fusion protein provided as SEQ ID NO: 108.

In still other embodiments, the fusion protein contains a chitosanase that derives from the nucleotide sequence set forth in SEQ ID NO: 106. The amino acid sequence for an exemplary chitosanase that may be fused to the targeting sequence, an exosporium protein, or an exosporium protein fragment and, optionally, a linker sequence, such as a poly-A linker, in the fusion protein is provided as SEQ ID NO: 109.

To create fusion constructs, genes may be fused to the native bclA promoter of *Bacillus thuringiensis* DNA encoding the first 35 amino acids of BclA (amino acids 1-35 of SEQ ID NO: 1) using the splicing by overlapping extension (SOE) technique. Correct amplicons are cloned into the *E. coli/Bacillus* shuttle vector pHP13, and correct clones screened by DNA sequencing. Correct clones are electroporated into *Bacillus thuringiensis* (Cry-, plasmid-) and screened for chloramphenicol resistance. Correct transformants are grown in brain heart infusion broth overnight at 30° C., plated onto nutrient agar plates, and incubated at 30° C. for 3 days. Spores expressing the fusion construct (BEMD spores) may be collected off of the plates by washing in phosphate buffered saline (PBS) and purified by centrifugation and additional washes in PBS.

In such fusion proteins, the endoglucanase, phospholipase or chitosinase can comprise a nucleotide sequence encoding an amino acid sequence having at least 85% identity with SEQ ID NO: 107, 108 or 109, respectively.

In such fusion proteins, the endoglucanase, phospholipase or chitosinase can comprise an amino acid sequence having at least 90% identity with SEQ ID NO: 107, 108 or 109, respectively.

In such fusion proteins, the endoglucanase, phospholipase or chitosinase can comprise an amino acid sequence having at least 95% identity with SEQ ID NO: 107, 108 or 109, respectively.

In such fusion proteins, the endoglucanase, phospholipase or chitosinase can comprise an amino acid sequence having at least 98% identity with SEQ ID NO: 107, 108 or 109, respectively.

In such fusion proteins, the endoglucanase, phospholipase or chitosinase can compirse an amino acid sequence having at least 99% identity with SEQ ID NO: 107, 108 or 109, respectively.

Suitable lignin oxidases comprise lignin peroxidases, laccases, glyoxal oxidases, ligninases, and manganese peroxidases.

The protease can comprise a subtilisin, an acid protease, an alkaline protease, a proteinase, a peptidase, an endopeptidase, an exopeptidase, a thermolysin, a papain, a pepsin, a trypsin, a pronase, a carboxylase, a serine protease, a glutamic protease, an aspartate protease, a cysteine protease, a threonine protease, or a metalloprotease.

The phosphatase can comprise a phosphoric monoester hydrolase, a phosphomonoesterase (e.g., PhoA4), a phosphoric diester hydrolase, a phosphodiesterase, a triphosphoric monoester hydrolase, a phosphoryl anhydride hydrolase, a pyrophosphatase, a phytase (e.g., *Bacillus subtilis* EE148 phytase or *Bacillus thuringiensis* BT013A phytase), a trimetaphosphatase, or a triphosphatase.

The nitrogenase can comprise a Nif family nitrogenase (e.g., *Paenibacillus massiliensis* NifBDEHKNXV).

Proteins and Peptides that Protects Plants from Pathogens

The fusion proteins can comprise a targeting sequence, exosporium protein, or exosporium protein fragment, and at least one protein or peptide that protects a plant from a pathogen.

The protein or peptide can comprise a protein or peptide that stimulates a plant immune response. For example, the protein or peptide that stimulates a plant immune response can comprise a plant immune system enhancer protein or peptide. The plant immune system enhancer protein or peptide can be any protein or peptide that has a beneficial effect on the immune system of a plant. Suitable plant immune system enhancer proteins and peptides include harpins, α-elastins, β-elastins, systemins, phenylalanine ammonia-lyase, elicitins, defensins, cryptogeins, flagellin proteins, and flagellin peptides (e.g., flg22).

Alternatively, the protein or peptide that protects a plant from a pathogen can be a protein or peptide that has antibacterial activity, antifungal activity, or both antibacterial and antifungal activity. Examples of such proteins and peptides include bacteriocins, lysozymes, lysozyme peptides (e.g., LysM), siderophores, non-ribosomal active peptides, conalbumins, albumins, lactoferrins, lactoferrin peptides (e.g., LfcinB), streptavidin and TasA.

The protein or peptide that protects a plant from a pathogen can also be a protein or peptide that has insecticidal activity, helminthicidal activity, suppresses insect or worm predation, or a combination thereof. For example, the protein or peptide that protects a plant from a pathogen can comprise an insecticidal bacterial toxin (e.g., a VIP insecticidal protein), an endotoxin, a Cry toxin (e.g., a Cry toxin from *Bacillus thuringiensis*), a protease inhibitor protein or peptide (e.g., a trypsin inhibitor or an arrowhead protease inhibitor), a cysteine protease, or a chitinase. Where the Cry toxin is a Cry toxin from *Bacillus thuringiensis*, the Cry toxin can be a Cry5B protein or a Cry21A protein. Cry5B and Cry21A have both insecticidal and nematocidal activity.

The protein that protects a plant from a pathogen can comprise an enzyme. Suitable enzymes include proteases and lactonases. The proteases and lactonases can be specific for a bacterial signaling molecule (e.g., a bacterial lactone homoserine signaling molecule).

Where the enzyme is a lactonase, the lactonase can comprise 1,4-lactonase, 2-pyrone-4,6-dicarboxylate lactonase, 3-oxoadipate enol-lactonase, actinomycin lactonase, deoxylimonate A-ring-lactonase, gluconolactonase L-rhamnono-1,4-lactonase, limonin-D-ring-lactonase, steroid-lactonase, triacetate-lactonase, or xylono-1,4-lactonase.

The enzyme can also be an enzyme that is specific for a cellular component of a bacterium or fungus. For example, the enzyme can comprise a β-1,3-glucanase, a β-1,4-glucanase, a β-1,6-glucanase, a chitosinase, a chitinase, a chitosinase-like enzyme, a lyticase, a peptidase, a proteinase, a protease (e.g., an alkaline protease, an acid protease, or a neutral protease), a mutanolysin, a stapholysin, or a lysozyme.

Proteins and Peptides that Enhance Stress Resistance in Plants

The fusion proteins can comprise a targeting sequence, exosporium protein, or exosporium protein fragment and at least one protein or peptide that enhances stress resistance in a plant.

For example, the protein or peptide that enhances stress resistance in a plant comprises an enzyme that degrades a stress-related compound. Stress-related compounds include, but are not limited to, aminocyclopropane-1-carboxylic acid (ACC), reactive oxygen species, nitric oxide, oxylipins, and phenolics. Specific reactive oxygen species include hydroxyl, hydrogen peroxide, oxygen, and superoxide. The enzyme that degrades a stress-related compound can comprise a superoxide dismutase, an oxidase, a catalase, an aminocyclopropane-1-carboxylic acid deaminase, a peroxidase, an antioxidant enzyme, or an antioxidant peptide.

The protein or peptide that enhances stress resistance in a plant can also comprise a protein or peptide that protects a plant from an environmental stress. The environmental stress can comprise, for example, drought, flood, heat, freezing, salt, heavy metals, low pH, high pH, or a combination thereof. For instance, the protein or peptide that protects a plant from an environmental stress can comprises an ice nucleation protein, a prolinase, a phenylalanine ammonia lyase, an isochorismate synthase, an isochorismate pyruvate lyase, or a choline dehydrogenase.

Plant Binding Proteins and Peptides

The fusion proteins can comprise a targeting sequence, exosporium protein, or exosporium protein fragment and at least plant binding protein or peptide. The plant binding protein or peptide can be any protein or peptide that is capable of specifically or non-specifically binding to any part of a plant (e.g., a plant root or an aerial portion of a plant such as a leaf, stem, flower, or fruit) or to plant matter. Thus, for example, the plant binding protein or peptide can be a root binding protein or peptide, or a leaf binding protein or peptide.

Suitable plant binding proteins and peptides include adhesins (e.g., rhicadhesin), flagellins, omptins, lectins, expansins, biofilm structural proteins (e.g., TasA or YuaB) pilus proteins, curlus proteins, intimins, invasins, agglutinins, and afimbrial proteins.

Recombinant *Bacillus* that Express the Fusion Proteins

The fusion proteins described herein can be expressed by recombinant exosporium-producing *Bacillus* cells. The fusion protein can be any of the fusion proteins discussed above.

The recombinant exosporium-producing *Bacillus* cells can coexpress two or more of any of the fusion proteins discussed above. For example, the recombinant exosporium-producing *Bacillus* cells can coexpress at least one fusion protein that comprises a plant binding protein or peptide, together with at least one fusion protein comprising a plant growth stimulating protein or peptide, at least one fusion protein comprising a protein or peptide that protects a plant from a pathogen, or at least one protein or peptide that enhances stress resistance in a plant.

The recombinant exosporium-producing *Bacillus* cells can comprise *Bacillus anthracis, Bacillus cereus, Bacillus thuringiensis, Bacillus mycoides, Bacillus pseudomycoides, Bacillus samanii, Bacillus gaemokensis, Bacillus weihenstephensis, Bacillus toyoiensis* or a combination thereof. For example, the recombinant exosporium-producing *Bacillus* cells can comprise *Bacillus cereus, Bacillus thuringiensis, Bacillus pseudomycoides*, or *Bacillus mycoides*. In particular, the recombinant exosporium-producing *Bacillus* cells can comprise *Bacillus thuringiensis* or *Bacillus mycoides*.

To generate a recombinant exosporium-producing *Bacillus* cells expressing a fusion protein, any *Bacillus cereus* family member can be conjugated, transduced, or transformed with a vector encoding the fusion protein using standard methods known in the art (e.g., by electroporation). The bacteria can then be screened to identify transformants by any method known in the art. For example, where the vector includes an antibiotic resistance gene, the bacteria can be screened for antibiotic resistance. Alternatively, DNA encoding the fusion protein can be integrated into the chromosomal DNA of a *B. cereus* family member host. The recombinant exosporium-producing *Bacillus* cells can then exposed to conditions which will induce sporulation. Suitable conditions for inducing sporulation are known in the art. For example, the recombinant exosporium-producing *Bacillus* cells can be plated onto agar plates, and incubated at a temperature of about 30° ° C. for several days (e.g., 3 days).

Inactivated strains, non-toxic strains, or genetically manipulated strains of any of the above species can also suitably be used. For example, a *Bacillus thuringiensis* that lacks the Cry toxin can be used. Alternatively or in addition, once the recombinant *B. cereus* family spores expressing the fusion protein have been generated, they can be inactivated to prevent further germination once in use. Any method for inactivating bacterial spores that is known in the art can be used. Suitable methods include, without limitation, heat treatment, gamma irradiation, x-ray irradiation, UV-A irradiation, UV-B irradiation, chemical treatment (e.g., treatment with gluteraldehyde, formaldehyde, hydrogen peroxide, acetic acid, bleach, or any combination thereof), or a combination thereof. Alternatively, spores derived from nontoxigenic strains, or genetically or physically inactivated strains, can be used.

Recombinant Exosporium-Producing *Bacillus* Cells Having Plant-Growth Promoting Effects and/or Other Beneficial Attributes Many *Bacillus cereus* family member strains have inherent beneficial attributes. For example, some strains have plant-growth promoting effects. Any of the fusion proteins described herein can be expressed in such strains.

For example, the recombinant exosporium-producing *Bacillus* cells can comprise a plant-growth promoting strain of bacteria.

The plant-growth promoting strain of bacteria can comprise a strain of bacteria that produces an insecticidal toxin (e.g., a Cry toxin), produces a fungicidal compound (e.g., a β-1,3-glucanase, a chitosinase, a lyticase, or a combination thereof), produces a nematocidal compound (e.g., a Cry toxin), produces a bacteriocidal compound, is resistant to one or more antibiotics, comprises one or more freely replicating plasmids, binds to plant roots, colonizes plant roots, forms biofilms, solubilizes nutrients, secretes organic acids, or any combination thereof.

For example, where the recombinant exosporium-producing *Bacillus* cells comprises a plant-growth promoting strain of bacteria, the plant growth-promoting strain of bacteria can comprise *Bacillus mycoides* BT155 (NRRL No. B-50921), *Bacillus mycoides* EE118 (NRRL No. B-50918), *Bacillus mycoides* EE141 (NRRL No. B-50916), *Bacillus mycoides* BT46-3 (NRRL No. B-50922), *Bacillus cereus* family member EE128 (NRRL No. B-50917), *Bacillus thuringiensis* BT013A (NRRL No. B-50924), or *Bacillus cereus* family member EE349 (NRRL No. B-50928). *Bacillus thuringiensis* BT013A is also known as *Bacillus thuringiensis* 4Q7. Each of these strains was deposited with the United States Department of Agriculture (USDA) Agricultural Research Service (ARS), having the address 1815 North University Street, Peoria, Illinois 61604, U.S.A., on Mar. 10, 2014, and is identified by the NRRL deposit number provided in parentheses. These deposits will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicants will make available to the public, pursuant to 37 C.F.R. § 1.808, sample(s) of the deposit with the NRRL.

These plant-growth promoting strains were isolated from the rhizospheres of various vigorous plants and were identified by their 16S rRNA sequences, and through biochemical assays. The strains were identified at least to their genus designation by means of conventional biochemistry and morphological indicators. Biochemical assays for confirmed Gram-positive strains such as *Bacillus* included growth on PEA medium and nutrient agar, microscopic examination, growth on 5% and 7.5% NaCl medium, growth at pH 5 and pH 9, growth at 42° C. and 50° C., the ability to produce acid upon fermentation with cellobiose, lactose, glycerol, glucose, sucrose, d-mannitol, and starch; fluorescent pigment production; gelatin hydrolysis; nitrate reduction; catalase production, starch hydrolysis; oxidase reaction, urease production and motility.

For example, the recombinant exosporium-producing *Bacillus* cells comprising a plant-growth promoting strain of bacteria can comprise *Bacillus mycoides* BT155, *Bacillus mycoides* EE141, or *Bacillus thuringiensis* BT013A. The recombinant exosporium-producing *Bacillus* cells can express any of the fusion proteins described herein, e.g., a fusion protein comprising the targeting sequence of SEQ ID NO: 60 and a non-hormone peptide (e.g., kunitz trypsin inhibitor (KTI)), an enzyme involved in the production or activation of a plant growth stimulating compound (e.g., a chitosinase), a plant binding protein or peptide (e.g., TasA); a protein or peptide that protects a plant from a pathogen (e.g., TasA), or an enzyme that degrades or modifies a bacterial, fungal, or plant nutrient source (e.g., a phosphatase such as PhoA or phytase, or an endoglucanase).

Promoters

In any of the recombinant exosporium-producing *Bacillus* cells described herein, the fusion protein can be expressed under the control of a promoter that is native to the targeting sequence, the exosporium protein, or the exosporium protein fragment of the fusion protein. For example, where the fusion protein comprises a targeting sequence derived from *B. anthracis* Sterne BclA (e.g., amino acids 20-35 of SEQ ID NO: 1, amino acids 1-35 of SEQ ID NO: 1, SEQ ID NO: 1, or SEQ ID NO: 60) or where the fusion protein comprises full length BclA (SEQ ID NO: 2) or a fragment of full length BclA (e.g., SEQ ID NO: 59), the fusion protein can be expressed under the control of a promoter that is normally associated with the BclA gene in the genome of *B. anthracis* Sterne (e.g., the promoter of SEQ ID NO: 85).

Alternatively, the fusion protein can be expressed under the control of a high-expression sporulation promoter. In some cases, the promoter that is native to the targeting sequence, exosporium protein, or exosporium protein fragment will be a high-expression sporulation promoter. In other cases, the promoter that is native to the targeting sequence, exosporium protein, or exosporium protein fragment will not be a high-expression sporulation promoter. In the latter cases, it may be advantageous to replace the native promoter with a high-expression sporulation promoter. Expression of the fusion protein under the control of a high-expression sporulation promoter provides for increased expression of the fusion protein on the exosporium of the *Bacillus cereus* family member.

The high-expression sporulation promoter can comprise one or more sigma-K sporulation-specific polymerase promoter sequences.

Suitable high-expression sporulation promoters for use in expressing the fusion proteins in a *Bacillus cereus* family member include those listed in Table 2 below:

TABLE 2

Promoter Sequences

| Promoter (SEQ ID NO.) | Sequence |
|---|---|
| BclA promoter (*B. anthracis* Sterne) (SEQ ID NO: 85) | TAATCACCCTCTTCCAAATCAATCATATGTTATACATATACTAAACT TTCCATTTTTTTAAATTGTTCAAGTAGTTTAAGATTTCTTTTCAATAAT TCAAATGTCCGTGTCATTTTCTTTCGGTTTTGCATCTACTATATAATG AACGCTTTATGGAGGTGAATTTATG |

TABLE 2-continued

Promoter Sequences

| Promoter (SEQ ID NO.) | Sequence |
|---|---|
| BetA promoter (*B. anthracis* Sterne) (SEQ ID NO: 86) | ATTTATTTCATTCAATTTTTCCTATTTAGTACCTACCGCACTCACAAAA AGCACCTCTCATTAATTTATATTATAGTCATTGAAATCTAATTTAATGA AATCATCATACTATATGTTTTATAAGAAGTAAAGGTACCATACTTAA TTAATACATATCTATACACTTCAATATCACAGCATGCAGTTGAATTATA TCCAACTTTCATTTCAAATTAAATAAGTGCCTCCGCTATTGTGAATGTC ATTTACTCTCCCTACTACATTTAATAATTATGACAAGCAATCATAGGA GGTTACTACATG |
| BAS 1882 promoter (*B. anthracis* Sterne) (SEQ ID NO: 87) | AATTACATAACAAGAACTACATTAGGGAGCAAGCAGTCTAGCGAAAGCT AACTGCTTTTTTATTAAATAACTATTTTATTAAATTTCATATATACAAT CGCTTGTCCATTTCATTTGGCTCTACCCACGCATTTACTATTAGTAAT ATGAATTTTTCAGAGGTGGATTTTATT |
| Gene 3572 promoter (*B. weihenstephensis* KBAB4) (SEQ ID NO: 88) | CTATGATTTAAGATACACAATAGCAAAAGAGAAACATATTATATAACG ATAAATGAAACTTATGTATATGTATGGTAACTGTATATATTACTACAA TACAGTATACTCATAGGAGGTAGGTATG |
| YVTN β-propeller protein promoter (*B. weihenstephensis* KBAB4) (SEQ ID NO: 89) | GGTAGGTAGATTTGAAATATGATGAAGAAAAGGAATAACTAAAAGGAGT CGATATCCGACTCCTTTTAGTTATAAATAATGTGGAATTAGAGTATAAT TTTATATAGGTATATTGTATTAGATGAACGCTTTATCCTTTAATTGTGA TTAATGATGGATTGTAAGAGAAGGGGCTTACAGTCCTTTTTTTATGGTG TTCTATAAGCCTTTTTAAAAGGGGTACCACCCCACACCCAAAAACAGGG GGGGTTATAACTACATATTGGATGTTTTGTAACGTACAAGAATCGGTAT TAATTACCCTGTAAATAAGTTATGTGTATATAAGGTAACTTTT ATATATTCTCCTACAATAAAATAAAGGAGGTAATAAAGTG |
| Cry1 A promoter (*B. thuringiensis* HD-73) (SEQ ID NO: 90) | AACCCTTAATGCATTGGTTAAACATTGTAAAGTCTAAAGCATGGATAAT GGGCGAGAAGTAAGTAGATTGTTAACACCCTGGGTCAAAAATTGATATT TAGTAAAATTAGTTGCACTTTGTGCATTTTTTCATAAGATGAGTC ATATGTTTTAAATTGTAGTAATGAAAAACAGTATTATATCATAATGA ATTGGTATCTTAATAAAAGATGGAGGTAACTTA |
| ExsY promoter (*B. thuringiensis* serovar konkukian str. 97-27) (SEQ ID NO: 91) | TAATTCCACCTTCCCTTATCCTCTTTCGCCTATTTAAAAAAAGGTCTTG AGATTGTGACCAAATCTCCTCAACTCCAATATCTTATTAATGTAAATA CAAACAAGAAGATAAGGAGTGACATTAA |
| CotY promoter (*B. thuringiensis* A1 Hakam) (SEQ ID NO: 92) | AGGATGTCTTTTTTTATATTGTATTATGTACATCCCTACTATATAAATT CCCTGCTTTTATCGTAAGAATTAACGTAATATCAACCATATCCCGTTC ATATTGTAGTAGTGTATGTCAGAACTCACGAGAAGGAGTGAACATAA |
| YjcA promoter (*B. thuringiensis* serovar kurstaki str. HD73) (SEQ ID NO: 93) | TTAATGTCACTCCTTATCTTCTTGTTTGTATTTACATTAATAAGATATT GGAGTTGAGGAGATTTGGTCACAATCTCAAGACCTTTTTTTTAAATAGG CGAAAGAGGATAAGGGAAGGTGGAATTA |
| YjcB promoter (*B. thuringiensis* serovar kurstaki str. HD73) (SEQ ID NO: 94) | ATATATTTTCATAATACGAGAAAAAGCGGAGTTTAAAAGAATGAGGGAA CGGAAATAAAGAGTTGTTCATATAGTAAATAGACAGAATTGACAGTAGA GGAGA |
| BxpB promoter (*B. thuringiensis* A1 Hakam) (SEQ ID NO: 95) | AAACTAAATAATGAGCTAAGCATGGATTGGGTGGCAGAATTATCTGCCA CCCAATCCATGCTTAACGAGTATTATTATGTAAATTTCTTAAAATTGGG AACTTGTCTAGAACATAGAACCTGTCCTTTTCATTAACTGAAAGTAGAA ACAGATAAAGGAGTGAAAAACA |
| Rhamnose promoter (*B. thuringiensis* A1 Hakam) (SEQ ID NO: 96) | ATTCACTACAACGGGGATGAGTTTGATGCGGATACATATGAGAAGTAC CGGAAAGTGTTTGTAGAACATTACAAAGATATATTATCTCCATCATAA AGGAGAGATGCAAAG |

TABLE 2-continued

Promoter Sequences

| Promoter (SEQ ID NO.) | Sequence |
|---|---|
| CotY/CotZ promoter (*B. anthracis* Sterne) (SEQ ID NO: 97) | CGCGCACCACTTCGTCGTACAACAACGCAAGAAGAAGTTGGGGATACAG CAGTATTCTTATTCAGTGATTTAGCACGCGGCGTAACAGGAGAAAACAT TCACGTTGATTCAGGGTATCATATCTTAGGATAAATATAATATTAATT TTAAAGGACAATCTCTACATGTTGAGATTGTCCTTTTTATTTGTTCTTA GAAAGAACGATTTTTAACGAAAGTTCTTACCACGTTATGAATATAAGTA TAATAGTACACGATTTATTCAGCTACGTA |
| BclC promoter (*B. anthracis* Sterne) (SEQ ID NO: 98) | TGAAGTATCTAGAGCTAATTTACGCAAAGGAATCTCAGGACAACACTTT CGCAACACCTATATTTTAAATTTAATAAAAAAAGAGACTCCGGAGTCAG AAATTATAAAGCTAGCTGGGTTCAAATCAAAAATTTCACTAAAACGATA TTATCAATACGCAGAAAATGGAAAAAACGCCTTATCATAAGGCGTTTTT TCCATTTTTTCTTCAAACAAACGATTTTACTATGACCATTTAACTAATT TTTGCATCTACTATGATGAGTTTCATTCACATTCTCATTAGAAAGGAG AGATTTAATG |
| Sigma K promoter (*B. anthracis* Sterne) (SEQ ID NO: 99) | TATATCATATGTAAAATTAGTTCTTATTCCCACATATCATATAGAATC GCCATATTATACATGCAGAAAACTAAGTATGGTATTATTCTTAAATTGT TTAGCACCTTCTAATATTACAGATAGAATCCGTCATTTTCAACAGTGAA CATGGATTTCTTCTGAACACAACTCTTTTTCTTTCCTTATTTCCAAAAA GAAAAGCAGCCCATTTTAAAATACGGCTGCTTGTAATGTACATTA |
| InhA promoter (*B. thuringiensis* A1 Hakam) (SEQ ID NO: 100) | TATCACATAACTCTTTATTTTAATATTTCGACATAAAGTGAAACTTTA ATCAGTGGGGGCTTTGTTCATCCCCCCACTGATTATTAATTGAACCAAG GGATAAAAAGATAGAGGGTCTGACCAGAAAACTGGAGGGCATGATTCTA TAACAAAAAGCTTAATGTTTATAGAATTATGTCTTTTTATATAGGGAGG GTAGTAAACAGAGATTTGGACAAAAATGCACCGATTTATCTGAATTTTA AGTTTTATAAAGGGGAGAAATG |
| BclA cluster glycosyl transferase operon 1 (*B. thuringiensis* serovar konkukian str. 97-27) (SEQ ID NO: 101) | ATTTTTTACTTAGCAGTAAAACTGATATCAGTTTTACTGCTTTTTCATT TTTAAATTCAATCATTAAATCTTCCTTTTCTACATAGTCATAATGTTGT ATGACATTCCGTAGGAGGCACTTATA |
| BclA cluster glycosyl transferase operon 2 (*B. thuringiensis* serovar kurstaki str. HD73) (SEQ ID NO: 102) | ACATAAATTCACCTCCATAAAGCGTTCATTATATAGTAGATGCAAACC GAAAGAAAATGACACGGACATTTGAATTATTGAAAAGAAATCTTAAACT ACTTGAACAATTTAAAAAAATGGAAAGTTTAGTATATGTATAAC ATATGATTGATTTGGAAGAGGGTGATTA |
| Glycosyl transferase promoter (*B. thuringiensis* A1 Hakam) (SEQ ID NO: 103) | TTCTATTTTCCAACATAACATGCTACGATTAAATGGTTTTTTGCAAATG CCTTCTTGGGAAGAAGGATTAGAGCGTTTTTTATAGAAACCAAAAGTC ATTAACAATTTTAAGTTAATGACTTTTTTGTTTGCCTTTAAGAGGTTTT ATGTTACTATAATTATAGTATCAGGTACTAATAACAAGTATAAGTATTT CTGGGAGGATATATCA |

In the promoter sequences listed in Table 2 above, the locations of the sigma-K sporulation-specific polymerase promoter sequences are indicated by bold and underlined text. The Cry1A promoter (*B. thuringiensis* HD-73; SEQ ID NO: 90) has a total of four sigma-K sequences, two of which overlap with one another, as indicated by the double underlining in Table 2.

Preferred high-expression sporulation promoters for use in expressing the fusion proteins in a *Bacillus cereus* family member include the BetA promoter (*B. anthracis* Sterne; SEQ ID NO: 86), the BclA promoter (*B. anthracis* Sterne; SEQ ID NO: 85), the BclA cluster glycosyl transferase operons 1 and 2 promoters (*B. anthracis* Sterne; SEQ ID NOS: 101 and 102), and the YVTN β-propeller protein promoter (*B. weihenstephensis* KBAB 4; SEQ ID NO: 89). In any of the recombinant exosporium-producing *Bacillus* cells described herein, the fusion protein can be expressed under the control of a sporulation promoter comprising a nucleic acid sequence having at least 80%, at least 90%, at least 95%, at least 98%, at least 99%, or 100% identity with a nucleic acid sequence of any one of SEQ ID NOS: 85-103.

When the sporulation promoter comprising a nucleic acid sequence having at least 80%, at least 90%, at least 95%, at least 98%, or at least 99% identity with a nucleic acid sequence of any one of SEQ ID NOS: 85-103, the sigma-K sporulation-specific polymerase promoter sequence or sequences preferably have 100% identity with the corresponding nucleotides of SEQ ID NO: 85, 86, 87, 88, 89, 90, 91, 92, 93, 94, 95, 96, 97, 98, 99, 100, 101, 102, or 103. For example, as illustrated in Table 2 above, the BclA promoter of *B. anthracis* Sterne (SEQ ID NO: 85) has sigma-K sporulation-specific polymerase promoter sequences at nucleotides 24-32, 35-43, and 129-137. Thus, if the sporulation promoter comprises a sequence having at least 90% identity with the nucleic acid sequence of SEQ ID NO: 85, it is preferred that the nucleotides of the sporulation promoter corresponding to nucleotides 24-32, 35-43, and 129-137 of SEQ ID NO: 85 have 100% identity with nucleotides 24-32, 35-43, and 129-137 of SEQ ID NO: 85.

In any of the methods described herein for stimulating plant growth, plants grown in the plant growth medium comprising the recombinant exosporium-producing *Bacillus* cells and at least one further biological control agent selected from the particular microorganisms disclosed herein exhibit increased growth as compared to the growth of plants in the identical plant growth medium that does not contain the recombinant exosporium-producing *Bacillus* cells.

In any of the compositions and methods described herein for stimulating plant growth, the recombinant exosporium-producing *Bacillus* cells can comprise any of the recombinant plant-growth promoting strains of bacteria described above.

In any of the compositions or methods for stimulating plant growth disclosed herein, the fusion protein can be expressed under the control of any of the promoters described above.

Synthetic Nodulation Factors and Plant Growth Stimulators

In some embodiments, the compositions comprising recombinant exosporium-producing *Bacillus* cells that express a fusion protein and at least one of the biological control agents described herein further comprise a synthetic nodulation factor and/or plant growth stimulator. A non-limiting example of such a synthetic compound is a compound of general formula (I)

(I)

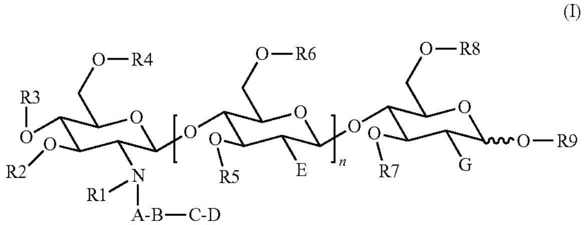

wherein:

n is 2 or 3;

A is —C(O)—;

B is a phenylene;

C is —O—;

D is a linear hydrocarbon-based chain comprising 11 carbons, which is saturated or unsaturated between carbons 4 and 5;

E and G are independently selected from the group consisting of a substituent NHR20;

R1, R2, R3, R4, R5, R6, R7, and R9 are H;

R8 is selected from the group consisting of H, fucosyl, methylfucosyl, $SO_3H$, $SO_3Li$, $SO_3Na$, $SO_3K$, and $SO_3N(C_{1-8}\text{-alkyl})_4$;

R20 is $C(O)C_{1-6}$-alkyl; and any agriculturally acceptable geometrical and/or optical isomer, enantiomer and/or diastereoisomer, tautomer, salt, N-oxide, sulfoxide, or sulfone thereof.

The salt may be selected from the group consisting of lithium, sodium, potassium, and tetraalkylammonium salts.

In certain embodiments, E and G are $NHC(O)CH_3$.

In other embodiments, R8 is selected from the group consisting of H, $SO_3H$, $SO_3Li$, $SO_3Na$, $SO_3K$, $SO_3N(C_{1-8}alkyl)_4$ and a substituent of formula:

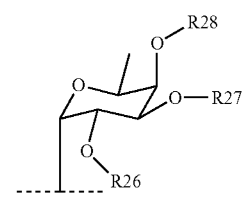

wherein:

R26 is selected from the group consisting of H and $CH_3$; and

R27 and R28 are independently selected from the group consisting of H, $C(O)CH_3$, $SO_3H$, $SO_3Li$, SOSNa, $SO_3K$ and $SO_3N(C_{1-8}alkyl)_4$.

In some aspects, R26, R27, and R28 are all hydrogen.

Additional non-limiting examples of a synthetic nodulation factor and/or plant growth stimulator that can be used in the present invention include compounds of the structural formulae:

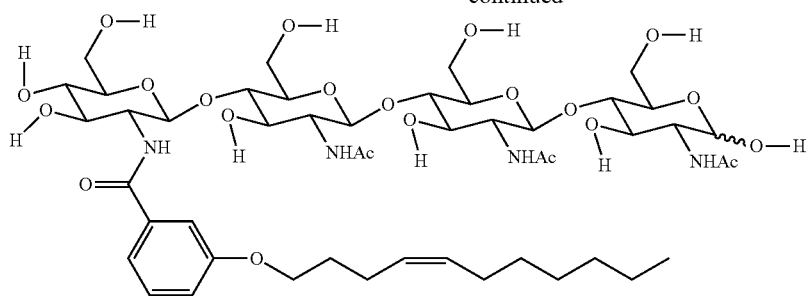
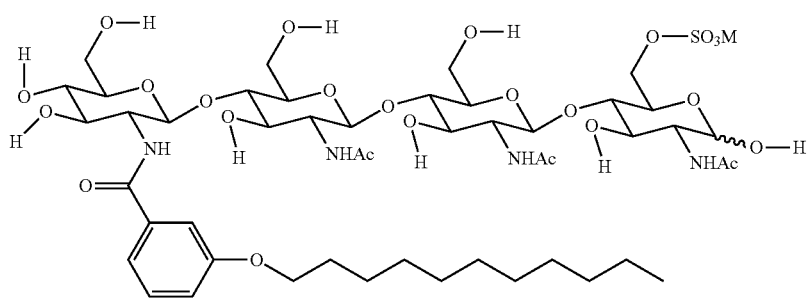
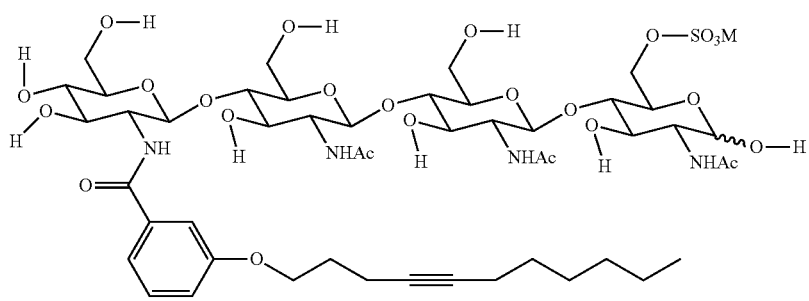
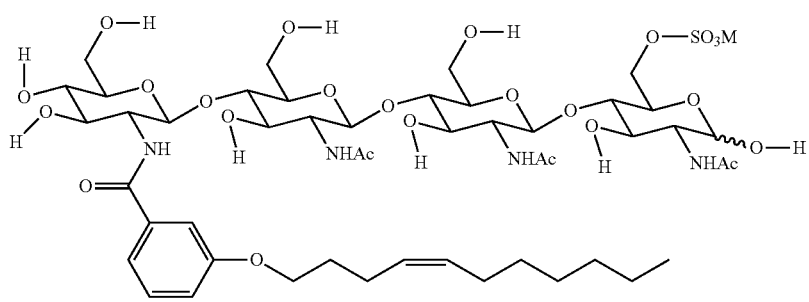
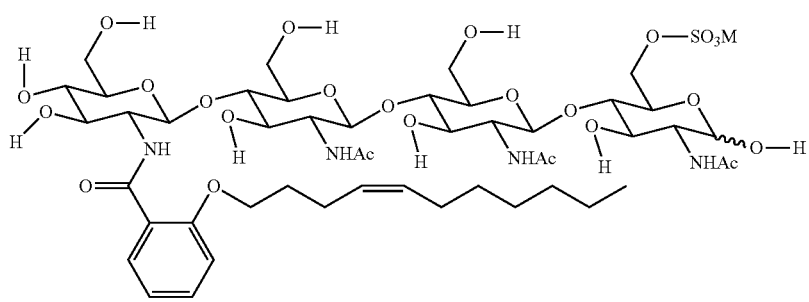

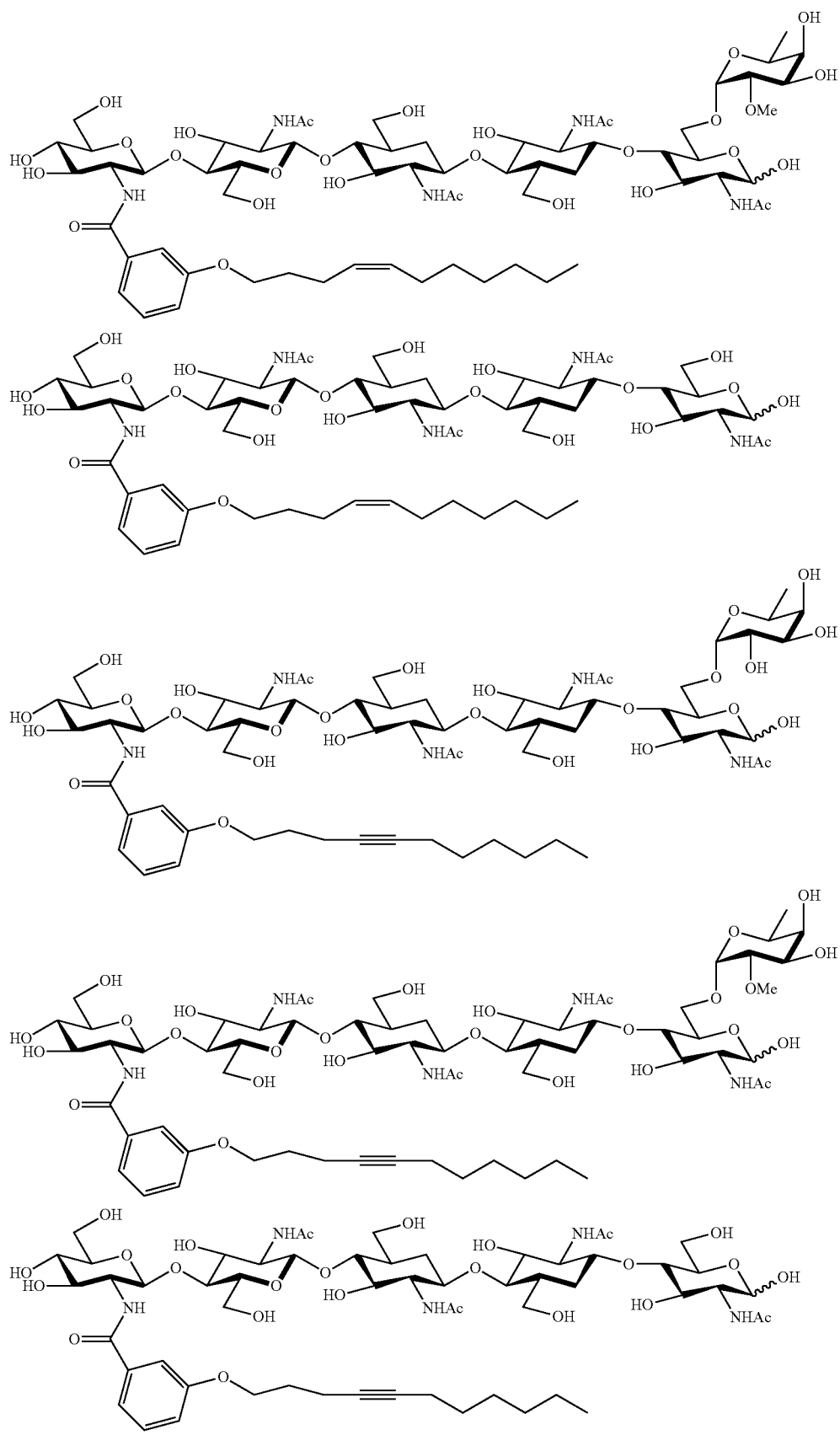

-continued
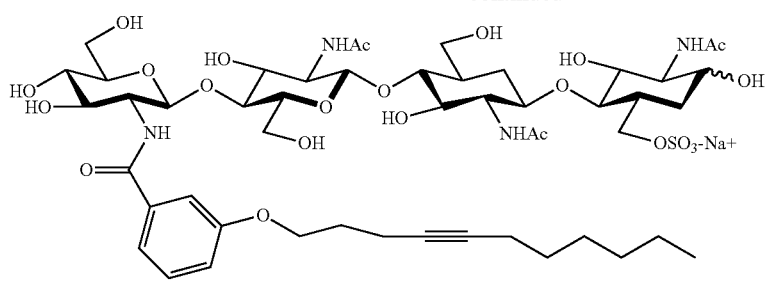
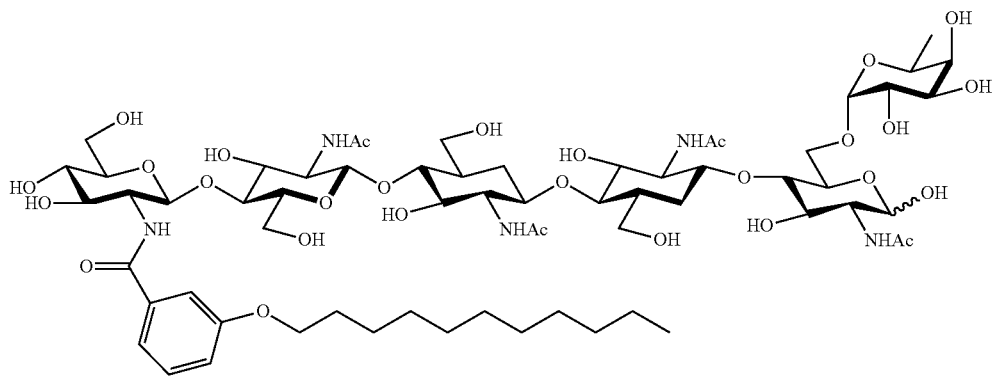
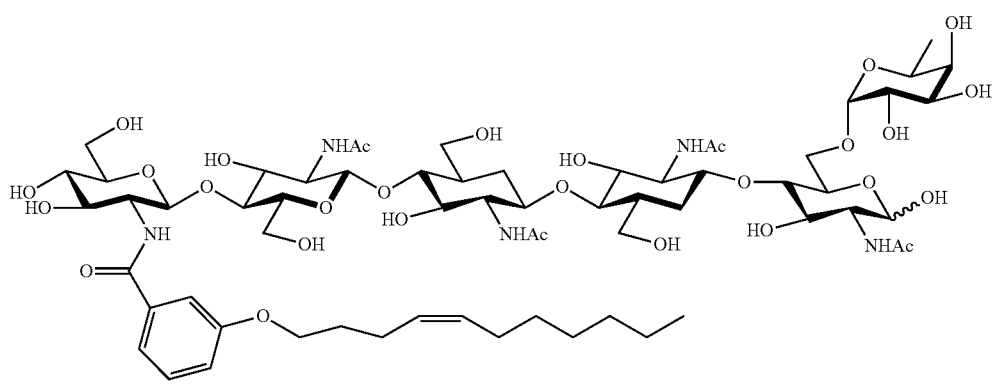
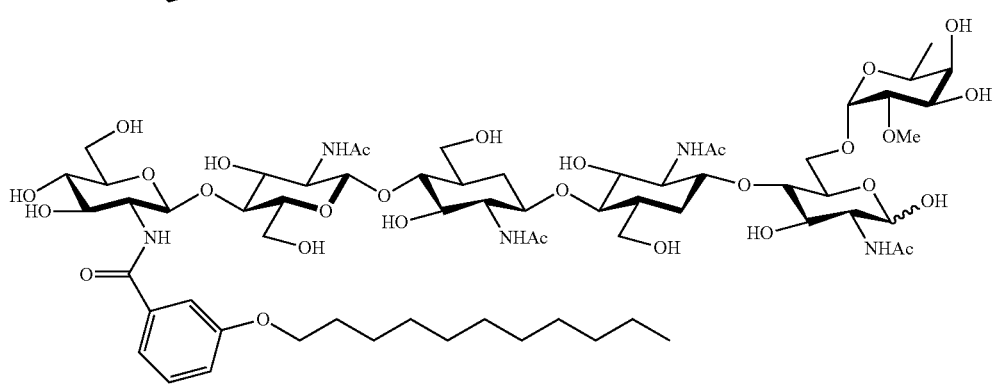
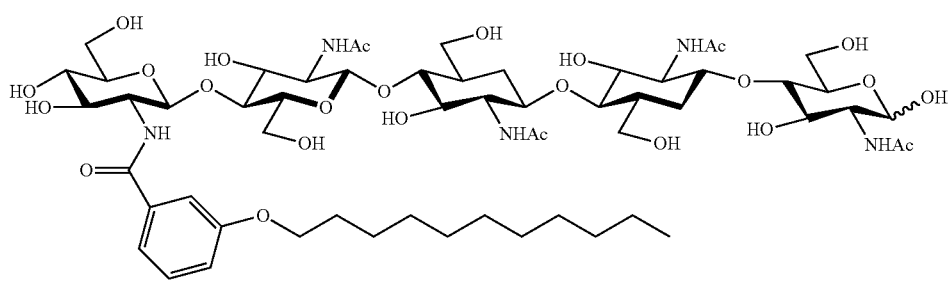

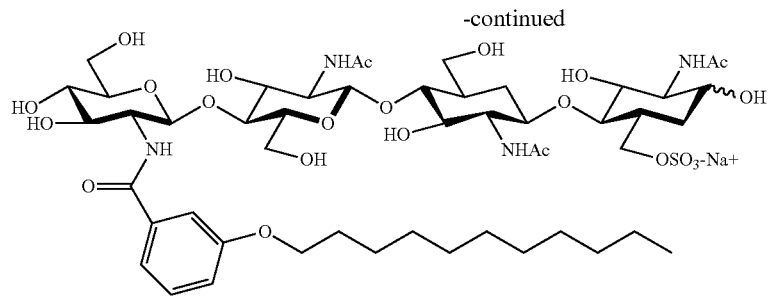

in which, when it is present, M is selected from the group consisting of $H^+$, $Li^+$, $Na^+$, $K^+$ and $(C_{1-8}alkyl)_4N^+$.

In certain aspects, the synthetic nodulation factor and/or plant growth stimulator is a compound selected from the group consisting of:

tive strain that exhibits activity against insects, mites, nematodes and/or phytopathogens. The present invention relates to the combinations of the above-described recombinant *Bacillus* cells with the particular biological control agents described herein and/or to mutants of specific strains of

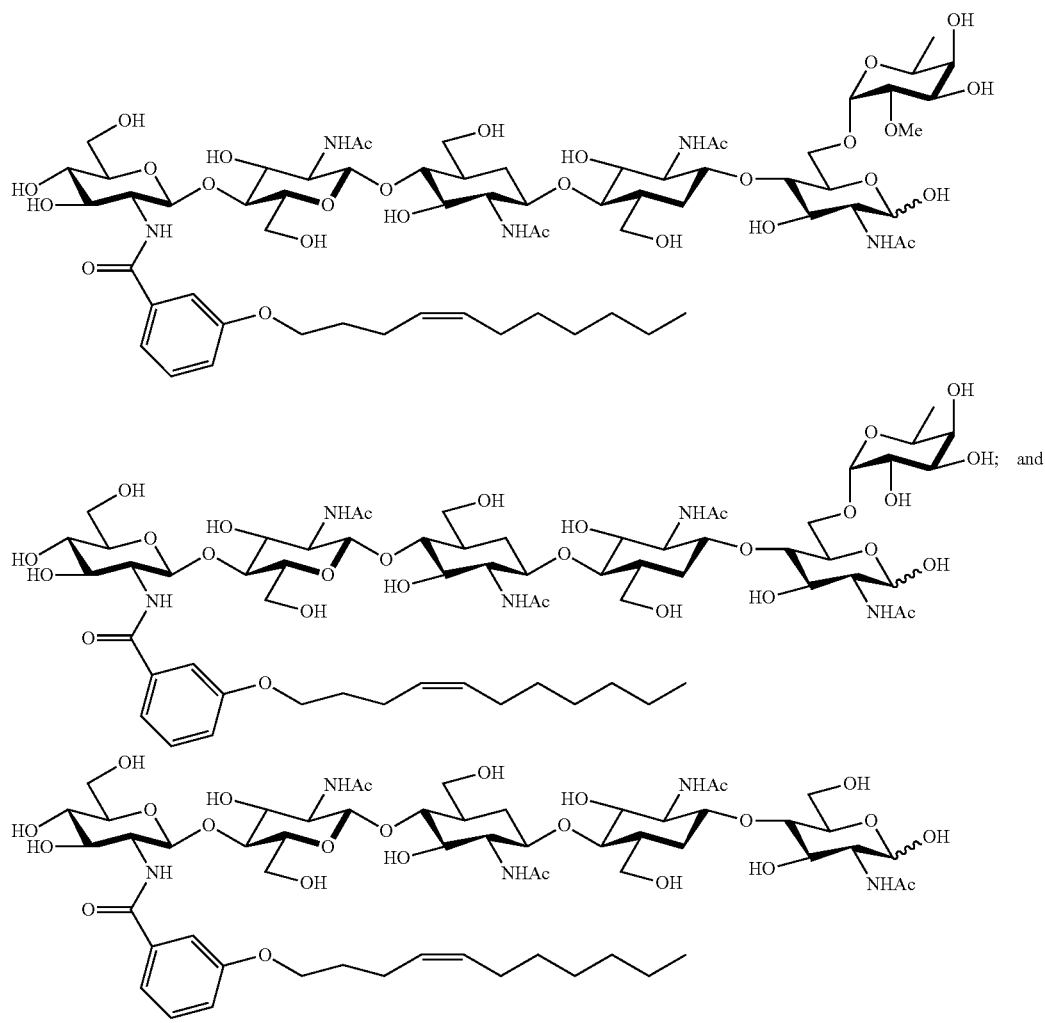

Additional Biological Control Agents

Biological control agents can include, in particular, bacteria, fungi or yeasts, protozoa, viruses, entomopathogenic nematodes, inoculants and botanicals and/or mutants of them having all identifying characteristics of the respective strain, and/or at least one metabolite produced by the respecmicroorganisms described herein, where the mutants have all the identifying characteristics of the respective strain, and/or at least one metabolite produced by the respective strain that exhibits activity against insects, mites, nematodes and/or phytopathogens or promotes plant growth and/or enhances plant health.

The bacterial cells, spores and metabolites in culture broth resulting from fermentation (the "whole broth" or "fermentation broth") of the particular microorganisms described herein may be used directly or concentrated by conventional industrial methods, such as centrifugation, filtration, and evaporation, or processed into dry powder and granules by spray drying, drum drying and freeze drying, for example.

The terms "whole broth" and "fermentation broth," as used herein, refer to the culture broth resulting from fermentation before any downstream treatment. The whole broth encompasses the microorganism and its component parts, unused raw substrates, and metabolites produced by the microorganism during fermentation. The term "broth concentrate," as used herein, refers to whole broth (fermentation broth) that has been concentrated by conventional industrial methods, as described above, but remains in liquid form. The term "fermentation solid," as used herein, refers to dried fermentation broth. The term "fermentation product," as used herein, refers to whole broth, broth concentrate and/or fermentation solids. Compositions of the present invention include fermentation products. In some embodiments, the concentrated fermentation broth is washed, for example, via a diafiltration process, to remove residual fermentation broth and metabolites.

In another embodiment, the fermentation broth or broth concentrate can be dried with or without the addition of carriers, inerts, or additives using conventional drying processes or methods such as spray drying, freeze drying, tray drying, fluidized-bed drying, drum drying, or evaporation.

According to the invention, biological control agents, which are summarized under the term "bacteria", include spore-forming, root-colonizing bacteria, or bacteria and their metabolites useful as biological insecticides, -nematicides, miticides, or -fungicide or soil amendments improving plant health and growth. Bacteria to be used or employed according to the invention follow.

*B. cereus* strains, including strain CNCM I-1562 (cf. U.S. Pat. No. 6,406,690), *Bacillus firmus, Bacillus pumilus*, in particular strain GB34 (products known as YIELD SHIELD®), and strain QST2808 (products known as SONATA® QST2808) *Bacillus subtilis*, in particular strain GB03 (products known as KODIAK®), strain QST713 (products known as SERENADE® QST713), strain AQ30002 (aka QST30002; NRRL Accession No. B-50421, known from WO 2012/087980, which is incorporated herein by reference), strain AQ30004 (aka QST30004; NRRL Accession No. B-50455, known from WO 2012/087980, which is incorporated herein by reference), strain AQ743 (NRRL Accession No. B-21665), strain AQ153 (ATCC Accession No. 55614 as described in WO 98/21964), (1.79) *Streptomyces galbus* strain AQ 6047 (Accession Number NRRL 30232), (1.91) *Rhodococcus globerulus* AQ719 (NRRL Accession No. B-21663), (1.92) *Bacillus* sp. AQ175 (ATCC Accession No. 55608), (1.93) *Bacillus* sp. AQ 177 (ATCC Accession No. 55609), (1.94) *Bacillus* sp. AQ178 (ATCC Accession No. 53522), (1.95) *Streptomyces* sp. strain described in WO 02/26041 A2 (NRRL Accession No. B-30145), (1.96) *Streptomyces microflavus* strain NRRL B-50550, (1.97) *Streptomyces microflavus* strain M (Accession No. 091013-02), gougerotin-containing fermentation products of *Streptomyces*, as described in WO2014/059275, and *Streptomyces galbus* QST6047, described in U.S. Pat. No. 6,682,925.

In a particular embodiment the following bacteria are used in combination with the exosporium-producing recombinant *Bacillus* cells described above:

*Bacillus firmus*, in particular strain I-1582 (products known as Bionem, Votivo, Flocter),

*Bacillus pumilus*, in particular strain GB34 (products known as YIELD SHIELD®), and strain QST2808 (products known as SONATA® QST2808),

*Bacillus subtilis*, in particular strain GB03 (products known as KODIAK®), strain QST713 (products known as SERENADE® QST713); NRRL Accession No. B-50455, known from WO 2012/087980, which is incorporated herein by reference), or *B. subtilis* var. *amyloliquefaciens* strain FZB24 (products known as TAEGRO®), strain AQ743 (NRRL Accession No. B-21665), strain AQ153 (ATCC Accession No. 55614 as described in WO 98/21964), In one embodiment the composition of the present invention comprises a combination of at least one of the particular biological control agents described herein and at least one further biological control agent selected from the group consisting of *Bacillus chitinosporus* AQ746 (NRRL Accession No. B-21618), *Bacillus mycoides* AQ726 (NRRL Accession No. B-21664), *Bacillus pumilus* QST2808 (NRRL Accession No. B-30087), *Bacillus pumilus* AQ717 (NRRL Accession No. B-21662), *Bacillus* sp. AQ175 (ATCC Accession No. 55608), *Bacillus* sp. AQ177 (ATCC Accession No. 55609), *Bacillus* sp. AQ178 (ATCC Accession No. 53522), *Bacillus subtilis* AQ743 (NRRL Accession No. B-21665), *Bacillus subtilis* AQ713 (NRRL Accession No. B-21661), *Bacillus subtilis* AQ153 (ATCC Accession No. 55614), *Muscodor albus* 620 (NRRL Accession No. 30547), *Muscodor roseus* A3-5 (NRRL Accession No. 30548), *Rhodococcus globerulus* AQ719 (NRRL Accession No. B-21663), *Streptomyces galbus* (NRRL Accession No. 30232), *Streptomyces* sp. (NRRL Accession No. B-30145), *Bacillus subtilis* AQ30002 (NRRL Accession No. B-50421), and *Bacillus subtilis* AQ30004 (NRRL Accession No. B-50455) and/or a mutant of these strains having all the identifying characteristics of the respective strain, and/or at least one metabolite produced by the respective strain that exhibits activity against insects, mites, nematodes and/or phytopathogens.

Said further biological control agents are known in the art as follows:

*Bacillus chitinosporus* AQ746 (NRRL Accession No. B-21618) is known from WO 98/21966 A2. It is specifically active against nematodes and insects and produces non-exotoxin, non-proteinaceous, active metabolites in its supernatant. Those metabolites are active against nematodes and cockroaches, but inactive against flies, corn rootworm or beet armyworm.

*Bacillus mycoides* AQ726 (NRRL Accession No. B-21664) and its water-soluble metabolites kill or stunt insects such as corn rootworm larvae and aphids (WO 99/09820 A1).

As described in WO 00/58442 A1 *Bacillus pumilus* QST2808 (NRRL Accession No. B-30087) is able to inhibit a broad range of fungal plant diseases in vivo. Commercially available formulations of this strain are sold under the tradenames SONATA® and BALLAD® PLUS from Bayer CropScience LP (North Carolina, USA).

*Bacillus pumilus* AQ717 (NRRL Accession B-21662) is known from WO 99/10477 A1. It produces a metabolite that exhibits pesticidal activity against corn rootworms, nematodes and beet armyworms.

The bacterial strains *Bacillus* sp. AQ175 (ATCC Accession No. 55608), *Bacillus* sp. AQ177 (ATCC Accession No. 55609) and *Bacillus* sp. AQ178 (ATCC Accession No.

53522) described in WO 98/21967 A1 are effective in treating and protecting plants from aboveground fungal and bacterial infections.

The metabolite-producing strain *Bacillus subtilis* AQ743 (NRRL Accession No. B-21665) kills or stunts corn rootworm larvae, beet armyworm larvae, fly adults and nematodes (cf. WO 99/09819).

*Bacillus subtilis* AQ713 (Accession No. B-21661), also named *Bacillus subtilis* QST713, exhibits broad fungicidal and bactericidal activity and also exhibits corn rootworm activity (WO 98/50422 A1). Commercially available formulation of this strain are available under the tradenames SERENADE® MAX, SERENADE SOIL®, SERENADE® ASO, SERENADE® CPB and RHAPSODY® from Bayer CropScience LP (North Carolina, USA). The SERENADE® product (U.S. EPA Registration No. 69592-12) contains a patented strain of *Bacillus subtilis* (strain QST713) and many different lipopeptides that work synergistically to destroy disease pathogens and provide superior antimicrobial activity. The SERENADE® product is used to protect plants such as vegetables, fruit, nut and vine crops against diseases such as Fire Blight, *Botrytis*, Sour Rot, Rust, *Sclerotinia*, Powdery Mildew, Bacterial Spot and White Mold. The SERENADE® products are available as either liquid or dry formulations which can be applied as a foliar and/or soil treatment. Copies of U.S. EPA Master Labels for the SERENADE® products, including SERENADE® ASO, SERENADE® MAX, and SERENADE SOIL®, are publicly available through National Pesticide Information Retrieval System's (NPIRSv) USEPA/OPP Pesticide Product Label System (PPLS).

SERENADE® ASO (Aqueous Suspension-Organic) contains 1.34% of dried QST713 as an active ingredient and 98.66% of other ingredients. SERENADE® ASO is formulated to contain a minimum of $1 \times 10^9$ cfu/g of QST713 while the maximum amount of QST713 has been determined to be $3.3 \times 10^{10}$ cfu/g. For further information, see the U.S. EPA Master Labels for SERENADE® ASO dated Jan. 4, 2010, which is incorporated by reference herein in its entirety.

SERENADE® MAX contains 14.6% of dried QST713 as an active ingredient and 85.4% of other ingredients. SERENADE® MAX is formulated to contain a minimum of $7.3 \times 10^9$ cfu/g of QST713 while the maximum amount of QST713 has been determined to be $7.9 \times 10^{10}$ cfu/g. For further information, see the U.S. EPA Master Label for SERENADE® MAX, which is incorporated by reference herein in its entirety.

*Bacillus subtilis* AQ153 (ATCC Accession No. 55614) as described in WO 98/21964 A1 is effective in inhibiting growth of plant pathogenic bacteria and fungi.

WO 02/02082898 A1 describes endophytic fungi including *Muscodor albus* 620, also known as *Muscodor albus* QST20799 (NRRL Accession No. 30547) and *Muscodor roseus* A3-5 (NRRL Accession No. 30548) that produce a mixture of volatile antibiotics with activity against fungi, bacteria, insects and nematodes.

*Rhodococcus globerulus* AQ719 (NRRL Accession No. B-21663) produces metabolites that exhibits pesticidal activity against corn rootworms (U.S. Pat. No. 6,027,723 A).

WO 01/79480 A2 describes a strain of *Streptomyces galbus* (NRRL Accession No. 30232) which shows insecticidal activity against Lepidoptera.

The *Streptomyces* sp. strain described in WO 02/26041 A2 (NRRL Accession No. B-30145) exhibits antifungal activity on specific plant pathogens such as *Alternaria*, *Phytophthora*, *Botrytis*, *Rhizoctonia* and *Sclerotinia*.

The strains *Bacillus subtilis* AQ30002 (also known as QST30002) (NRRL Accession No. B-50421, deposited on Oct. 5, 2010) and *Bacillus subtilis* AQ30004 (also known as QST30004) (NRRL Accession No. B-50455, deposited on Oct. 5, 2010) are known from WO 2012/087980 A1, which is incorporated herein by reference. As described therein, these BCAs exhibit a broad fungicidal and bactericidal activity. B19 and B20 have a mutation in the swrA gene that results in impaired swarming ability and enhanced plant health promotion compared to a strain containing a wildtype swrA gene. The mutation causes these BCAs to form a more robust biofilm than the wildtype strain, thereby enhancing its fungicidal and bactericidal activity.

In some embodiments, the biological control agent is a *Bacillus subtilis* strain, such as *Bacillus subtilis* QST713, which produces a fengycin-type compound, an iturin-type compound, and/or a surfactin-type compound. In some aspects, the lipopeptide is a fengycin-type compound such as plipastatin A1, plipastatin B1, plipastatin B2, fengycin A, fengycin B, agrastatin 1, or agrastatin 2. In other aspects, the lipopeptide is an iturin-type compound such as iturin A, mycosubtilin, or bacillomycin.

Other lipopeptide-producing strains that are suitable for use in the compositions and methods of the present invention include *Bacillus amyloliquefaciens* strain D747 (available as BACSTAR® from Etec Crop Solutions, NZ and also available as DOUBLE NICKEL™ from Certis, US); *Bacillus subtilis* MBI600 (available as SUBTILEX® from Becker Underwood, U.S. EPA Reg. No. 71840-8); *Bacillus subtilis* Y1336 (available as BIOBAC® WP from Bion-Tech, Taiwan, registered as a biological fungicide in Taiwan under Registration Nos. 4764, 5454, 5096 and 5277); *Bacillus amyloliquefaciens*, in particular strain FZB42 (available as RHIZOVITAL® from ABITEP, DE); and *Bacillus subtilis* var. *amyloliquefaciens* FZB24 is available from Novozymes Biologicals Inc. (Salem, Virginia) or Syngenta Crop Protection, LLC (Greensboro, North Carolina) as the fungicide TAEGRO® or TAEGRO® ECO (EPA Registration No. 70127-5).

In some embodiments, the biological control agent in the synergistic combinations of the present invention is:
*Bacillus firmus*, including strain I-1582 (products known as Bionem, Votivo, Flocter), disclosed in U.S. Pat. No. 6,406,690 (which is herein incorporated by reference) and deposited with the CNCM on May 29, 1995, with Accession No. CNCM I-1582,
*Bacillus pumilus*, including strain GB34 (products known as YIELD SHIELD®) and strain QST2808 (products known as SONATA® QST2808),
*Bacillus subtilis* and *Bacillus amyloliquefaciens*, including those that produce lipopeptides and, in particular, a combination of plipastatins or fengycins, surfactins and/or iturins. Also, as to *Bacillus subtilis*, in particular strain GB03 (products known as KODIAK®, c.f. U.S. EPA, Pesticide Fact Sheet—*Bacillus subtilis* GB03 1992), strain QST713 (products known as SERENADE® QST713), strain AQ30002 (aka QST30002; NRRL Accession No. B-50421, known from WO 2012/087980, which is incorporated herein by reference), and strain AQ30004 (aka QST30004; NRRL Accession No. B-50455, known from WO 2012/087980, which is incorporated herein by reference).

According to the invention biological control agents which may be comprised in the composition of the invention and that are summarized under the term "fungi" or "yeasts" are the following organisms and and/or mutants of them having all identifying characteristics of the respective strain, and/or metabolites produced by the respective strain that exhibit activity against insects, mites, nematodes and/or phytopathogens (the numbering is used in the complete description):

*Muscodor albus*, in particular strain QST20799 (products known as ARABESQUE™ or ANDANTE™), *Coniothyrium minitans*, in particular strain CON/M/91-8 (products known as CONTANS®), *Lagenidium giganteum* (products known as LAGINEX® by AgraQuest, Inc.), *Paecilomyces lilacinus*, in particular spores of *P. lilacinus* strain 251 (products known as BIOACT® cf. *Crop Protection* 2008, 27, 352-361).

According to one embodiment of the present invention the biological control agent comprises not only the pure cultures of the respective microorganisms, but also their suspensions in a whole broth culture or a metabolite-containing supernatant or a purified metabolite obtained from whole broth culture of the strain. "Whole broth culture" refers to a liquid culture containing both cells and media. "Supernatant" refers to the liquid broth remaining when cells grown in broth are removed by centrifugation, filtration, sedimentation, or other means well known in the art.

The above-mentioned metabolites produced by the non-pathogenic microorganisms include antibiotics, enzymes, siderophores and growth promoting agents, for example zwittermicin-A, kanosamine, polyoxine, enzymes such as α-amylase, chitinases, and pektinases, phytohormones and precursors thereof, such as auxines, gibberlin-like substances, cytokinin-like compounds, lipopeptides such as iturins, plipastatins or surfactins, e.g., agrastatin A, bacillomycin D, bacilysin, difficidin, macrolactin, fengycin, bacilysin and bacillaene.

According to the invention, the biological control agents described herein may be employed or used in any physiologic state such as active or dormant.

Compositions According to the Present Invention

According to the present invention the composition comprises a) a recombinant exosporium-producing *Bacillus* cells that expresses a fusion protein comprising: (i) at least one plant growth stimulating protein or peptide selected from the group consisting of an enzyme involved in the production or activation of a plant growth stimulating compound; an enzyme that degrades or modifies a bacterial, fungal, or plant nutrient source; and a protein or peptide that protects a plant from a pathogen; and (ii) a targeting sequence that localizes the fusion protein to the exosporium of the *Bacillus cereus* family member; and b) at least one further and different particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in a synergistically effective amount.

A "synergistically effective amount" according to the present invention represents a quantity of a combination of a recombinant exosporium-producing *Bacillus* cells that expresses a fusion protein and at least one further particular biological control agent described herein that is more effective against insects, mites, nematodes and/or phytopathogens than the recombinant exosporium-producing *Bacillus* cells that expresses a fusion protein or such further biological control agent alone. A "synergistically effective amount" according to the present invention also represents a quantity of a combination of a recombinant exosporium-producing *Bacillus* cells that expresses a fusion protein and at least one further particular biological control agent described herein that is more effective at enhancing plant growth and/or promoting plant health than the recombinant exosporium-producing *Bacillus* cells that expresses a fusion protein or such further biological control agent alone.

The present invention comprises each and every combination of each of the further particular biological control agents described herein with the recombinant exosporium-producing *Bacillus* cells.

In a preferred embodiment the composition according to the present invention comprises at least one additional fungicide and/or at least one insecticide, with the proviso that the recombinant exosporium-producing *Bacillus* cells, the insecticide and the fungicide are not identical.

The term "active compound" or "active ingredient" is used in the present description to designate the recombinant exosporium-producing *Bacillus* cells, the at least one further biological control agent and/or a mutant of it having all identifying characteristics of the respective strain, and/or at least one metabolite produced by the respective strain that exhibits activity against insects, mites, nematodes and/or phytopathogens, the at least one insecticide and the at least one fungicide.

Further Additives

One aspect of the present invention is to provide a composition as described above additionally comprising at least one auxiliary selected from the group consisting of extenders, solvents, spontaneity promoters, carriers, emulsifiers, dispersants, frost protectants, thickeners and adjuvants. Those compositions are referred to as formulations.

Accordingly, in one aspect of the present invention such formulations, and application forms prepared from them, are provided as crop protection agents and/or pesticidal agents, such as drench, drip and spray liquors, comprising the composition of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on Development and Use of FAO and WHO Specifications for Pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared either in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular: for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur, et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.0001% and 98% by weight of active compound or, with particular preference, between 0.01% and 95% by weight of active compound, more preferably between 0.5% and 90% by weight of active compound, based on the weight of the formulation. The content of the active compound is defined as the sum of the recombinant exosporium-producing *Bacillus* cells and the further particular biological control agent described herein and/or a mutant of a particular microorganism strain described herein having all identifying characteristics of the respective strain, and/or at least one metabolite produced by the respective strain that exhibits activity against insects, mites, nematodes and/or phytopathogens, and fungicide and/or insecticide, if present.

The active compound content of the application forms (crop protection products) prepared from the formulations may vary within wide ranges. The active compound concentration of the application forms may be situated typically between 0.0001% and 95% by weight of active compound, preferably between 0.0001% and 1% by weight, based on the weight of the application form. Application takes place in a customary manner adapted to the application forms.

Furthermore, in one aspect of the present invention a kit of parts is provided comprising recombinant exosporium-producing *Bacillus* cells and at least one further particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in a synergistically effective amount in a spatially separated arrangement.

In a further embodiment of the present invention the above-mentioned kit of parts further comprises at least one fungicide and/or at least one insecticide, with the proviso that the recombinant exosporium-producing *Bacillus* cells, insecticide and fungicide are not identical. The fungicide and/or the insecticide can be present either in the recombinant exosporium-producing *Bacillus cereus* family member-based biological control agent component of the kit of parts or in the component of the kit of parts comprising the particular biological control agent disclosed herein, being spatially separated or in both of these components. In one embodiment, the fungicide and the insecticide are present in the recombinant exosporium-producing *Bacillus cereus* family member-based biological control agent component.

Moreover, the kit of parts according to the present invention can additionally comprise at least one auxiliary selected from the group consisting of extenders, solvents, spontaneity promoters, carriers, emulsifiers, dispersants, frost protectants, thickeners and adjuvants as mentioned below. This at least one auxiliary can be present either in the recombinant exosporium-producing *Bacillus cereus* family member-based biological control agent component of the kit of parts or in the component of the kit of parts comprising the particular biological control agent disclosed herein, being spatially separated or in both of these components.

In another aspect of the present invention the composition as described above is used for reducing overall damage of plants and plant parts as well as losses in harvested fruits or vegetables caused by insects, mites, nematodes and/or phytopathogens.

Furthermore, in another aspect of the present invention the composition as described above increases the overall plant health.

The term "plant health" generally comprises various sorts of improvements of plants that are not connected to the control of pests. For example, advantageous properties that may be mentioned are improved crop characteristics including: emergence, crop yields, protein content, oil content, starch content, more developed root system, improved root growth, improved root size maintenance, improved root effectiveness, improved stress tolerance (e.g., against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination.

With regard to the use according to the present invention, improved plant health preferably refers to improved plant characteristics including: crop yield, more developed root system (improved root growth), improved root size maintenance, improved root effectiveness, tillering increase, increase in plant height, bigger leaf blade, less dead basal leaves, stronger tillers, greener leaf color, photosynthetic activity, more productive tillers, enhanced plant vigor, and increased plant stand.

With regard to the present invention, improved plant health preferably especially refers to improved plant properties selected from crop yield, more developed root system, improved root growth, improved root size maintenance, improved root effectiveness, tillering increase, and increase in plant height.

The effect of a composition according to the present invention on plant health as defined herein can be determined by comparing plants which are grown under the same environmental conditions, whereby a part of said plants is treated with a composition according to the present invention and another part of said plants is not treated with a composition according to the present invention. Instead, said other part is not treated at all or is treated with a placebo (i.e., an application without a composition according to the invention such as an application without all active ingredients (i.e., without the recombinant exosporium-producing *Bacillus* cells as described herein and without a further particular biological control agent as described herein), or an application without the recombinant exosporium-producing *Bacillus* cells as described herein, or an application without a further particular biological control agent disclosed herein.

The composition according to the present invention may be applied in any desired manner, such as in the form of a seed coating, soil drench, and/or directly in-furrow and/or as a foliar spray and applied either pre-emergence, post-emergence or both. In other words, the composition can be applied to the seed, the plant or to harvested fruits and vegetables or to the soil wherein the plant is growing or wherein it is desired to grow (plant's locus of growth).

Reducing the overall damage of plants and plant parts often results in healthier plants and/or in an increase in plant vigor and yield.

Preferably, the composition according to the present invention is used for treating conventional or transgenic plants or seed thereof.

The present invention also relates to methods for stimulating plant growth using any of the compositions described above comprising recombinant exosporium-producing *Bacillus* cells that express a fusion protein and at least one of the further particular biological control agents described herein. The method for stimulating plant growth comprises applying to a plant, a plant part, to the locus surrounding the plant or in which the plant will be planted (e.g., soil or other growth medium) a composition comprising recombinant exosporium-producing *Bacillus* cells that express a fusion protein comprising: (i) at least one plant growth stimulating protein or peptide; and (ii) a targeting sequence, exosporium protein, or exosporium protein fragment, and at least one further particular biological control agent disclosed herein and/or a mutant of a specific strain of a microorganism disclosed herein having all identifying characteristics of the respective strain, and/or at least one metabolite produced by the respective strain that exhibits activity against insects, mites, nematodes and/or phytopathogens in a synergistically effective amount.

In another aspect of the present invention a method for reducing overall damage of plants and plant parts as well as losses in harvested fruits or vegetables caused by insects, mites, nematodes and/or phytopathogens is provided comprising the step of simultaneously or sequentially applying the recombinant exosporium-producing *Bacillus* cells and at least one further particular biological control agent described herein in a synergistically effective amount.

In one embodiment of the present method the composition further comprises at least one fungicide. In one aspect, the at least one fungicide is a synthetic fungicide. In a further aspect of this embodiment, the at least one fungicide is selected from the following group: bitertanol, bixafen, bromuconazole, carbendazim, carpropamid, dichlofluanid, fenamidone, fenhexamid, fentin acetate, fentin hydroxide, fluopicolide, fluopyram, fluoxastrobin, fluquinconazole, fosetyl, iprodione, iprovalicarb, isotianil, metominostrobin, ofurace, pencycuron, penflufen, prochloraz, propamocarb, propineb, prothioconazole, pyrimethanil, spiroxamine, tebuconazole, tolylfluanid, triadimefon, triadimenol, triazoxide, and trifloxystrobin.

In another embodiment, the composition comprises at least one insecticide in addition to the fungicide or in place of the fungicide, provided that the insecticide, the fungicide, the recombinant exosporium-producing *Bacillus* cells and the particular biological control agent disclosed herein are not identical.

In one embodiment, the at least one insecticide is a synthetic insecticide. In a further embodiment, the at least one insecticide is selected from the following group: acetamiprid, aldicarb, amitraz, beta-cyfluthrin, carbaryl, clothianidin, cyfluthrin, cypermethrin, deltamethrin, endosulfan, ethion, ethiprole, ethoprophos, fenamiphos, fenobucarb, fenthion, fipronil, flubendiamide, fluopyram, flupyradifurone, formetanate, heptanophos, imidacloprid, methamidophos, methiocarb, methomyl, niclosamide, oxydemetonmethyl, phosalone, silafluofen, spirodiclofen, spiromesifen, spirotetramat, thiacloprid, thiodicarb, tralomethrin, triazophos, triflumuron, and vamidothion.

The method of the present invention includes the following application methods, namely both of the recombinant exosporium-producing *Bacillus* cells and the at least one further particular biological control agent disclosed herein may be formulated into a single, stable composition with an agriculturally acceptable shelf life (so called "solo-formulation"), or being combined before or at the time of use (so called "combined-formulations").

If not mentioned otherwise, the expression "combination" stands for the various combinations of the recombinant exosporium-producing *Bacillus* cells and the at least one further particular biological control agent disclosed herein, and optionally the at least one fungicide and/or the at least one insecticide, in a solo-formulation, in a single "ready-mix" form, in a combined spray mixture composed from solo-formulations, such as a "tank-mix", and especially in a combined use of the single active ingredients when applied in a sequential manner, i.e., one after the other within a reasonably short period, such as a few hours or days, e.g., 2 hours to 7 days. The order of applying the composition according to the present invention is not essential for working the present invention. Accordingly, the term "combination" also encompasses the presence of the recombinant exosporium-producing *Bacillus* cells and the at least one further particular biological control agent disclosed herein, and optionally the at least one fungicide and/or insecticide on or in a plant to be treated or its surrounding, habitat or storage space, e.g., after simultaneously or consecutively applying the recombinant exosporium-producing *Bacillus* cells and the at least one further particular biological control agent disclosed herein, and optionally the at least one fungicide and/or the at least one insecticide to a plant its surrounding, habitat or storage space.

If the recombinant exosporium-producing *Bacillus* cells and the at least one further particular biological control agent described herein, and optionally the at least one fungicide and/or the at least one insecticide are employed or used in a sequential manner, it is preferred to treat the plants or plant parts (which includes seeds and plants emerging from the seed), harvested fruits and vegetables according to the following method: Firstly applying the at least one fungicide and/or the at least one insecticide on the plant or plant parts, and secondly applying the further particular biological control agent described herein and the recombinant exosporium-producing *Bacillus* cells to the same plant or plant parts. By this application manner the amount of residues of insecticides/fungicides on the plant upon harvesting is as low as possible. The time periods between the first and the second application within a (crop) growing cycle may vary and depend on the effect to be achieved. For example, the first application is done to prevent an infestation of the plant or plant parts with insects, mites, nematodes and/or phytopathogens (this is particularly the case when treating seeds) or to combat the infestation with insects, mites, nematodes and/or phytopathogens (this is particularly the case when treating plants and plant parts) and the second application is done to prevent or control the infestation with insects, mites, nematodes and/or phytopathogens and/or to promote plant growth. Control in this context means that the composition comprising the recombinant exosporium-producing *Bacillus* cells and the particular biological control agent disclosed herein are not able to fully exterminate the pests or phytopathogenic fungi but are able to keep the infestation on an acceptable level.

The present invention also provides methods of enhancing the killing, inhibiting, preventative and/or repelling activity of the compositions of the present invention by multiple applications. In some other embodiments, the compositions of the present invention are applied to a plant and/or plant part for two times, during any desired development stages or under any predetermined pest pressure, at an interval of about 1 hour, about 5 hours, about 10 hours, about 24 hours, about two days, about 3 days, about 4 days, about 5 days, about 1 week, about 10 days, about two weeks, about three weeks, about 1 month or more. Still in some embodiments, the compositions of the present invention are applied to a plant and/or plant part for more than two times, for example, 3 times, 4 times, 5 times, 6 times, 7 times, 8 times, 9 times, 10 times, or more, during any desired development stages or under any predetermined pest pressure, at an interval of about 1 hour, about 5 hours, about 10 hours, about 24 hours, about two days, about 3 days, about 4 days, about 5 days, about 1 week, about 10 days, about two weeks, about three weeks, about 1 month or more. The intervals between each application can vary if it is desired. One skilled in the art will be able to determine the application times and length of interval depending on plant species, plant pest species, and other factors.

By following the before mentioned steps, a very low level of residues of the at least one fungicide and/or at least one insecticide on the treated plant, plant parts, and the harvested fruits and vegetables can be achieved.

If not mentioned otherwise the treatment of plants or plant parts (which includes seeds and plants emerging from the seed), harvested fruits and vegetables with the composition according to the invention is carried out directly or by action on their surroundings, habitat or storage space using customary treatment methods, for example dipping, spraying, atomizing, irrigating, evaporating, dusting, fogging, broadcasting, foaming, painting, spreading-on, watering (drenching), drip irrigating. It is furthermore possible to apply the recombinant exosporium-producing *Bacillus* cells, the at least one further particular biological control agent described herein, and optionally the at least one fungicide and/or the at least one insecticide as solo-formulation or combined-formulations by the ultra-low volume method, or to inject the composition according to the present invention as a composition or as sole-formulations into the soil (in-furrow).

The term "plant to be treated" encompasses every part of a plant including its root system and the material—e.g., soil or nutrition medium—which is in a radius of at least 10 cm, 20 cm, 30 cm around the caulis or bole of a plant to be treated or which is at least 10 cm, 20 cm, 30 cm around the root system of said plant to be treated, respectively.

The amount of the recombinant exosporium-producing *Bacillus* cells, which is used or employed in combination with at least one further particular biological control agent described herein, optionally in the presence of at least one fungicide and/or the at least one insecticide, depends on the final formulation as well as size or type of the plant, plant parts, seeds, harvested fruits and vegetables to be treated. Usually, the recombinant exosporium-producing *Bacillus* cells to be employed or used according to the invention is present in about 1% to about 80% (w/w), preferably in about 1% to about 60% (w/w), more preferably about 10% to about 50% (w/w) of its solo-formulation or combined-formulation with the at least one further particular biological control agent described herein, and optionally the fungicide and/or the at least one insecticide.

Also the amount of the at least one further particular biological control agent disclosed herein which is used or employed in combination with the recombinant exosporium-producing *Bacillus* cells, optionally in the presence of at least one fungicide and/or the at least one insecticide, depends on the final formulation as well as size or type of the plant, plant parts, seeds, harvested fruit or vegetable to be treated. Usually, the further particular biological control agent described herein to be employed or used according to the invention is present in about 0.1% to about 80% (w/w), preferably 1% to about 60% (w/w), more preferably about 10% to about 50% (w/w) of its solo-formulation or combined-formulation with the recombinant exosporium-producing *Bacillus* cells, and optionally the at least one fungicide and/or the at least one insecticide.

Application of the recombinant exosporium-producing *Bacillus* cells may be effected as a foliar spray, as a soil treatment, and/or as a seed treatment/dressing. When used as a foliar treatment, in one embodiment, about 1/16 to about 5 gallons of whole broth are applied per acre. When used as a soil treatment, in one embodiment, about 1 to about 5 gallons of whole broth are applied per acre. When used for seed treatment about 1/32 to about 1/4 gallons of whole broth are applied per acre. For seed treatment, the end-use formulation contains at least $1 \times 10^4$, at least $1 \times 10^5$, at least $1 \times 10^6$, $1 \times 10^7$, at least $1 \times 10^8$, at least $1 \times 10^9$, at least $1 \times 10^{10}$ colony forming units per gram.

The recombinant exosporium-producing *Bacillus* cells and at least one further particular biological control agent disclosed herein, and if present preferably also the fungicide and/or the insecticide are used or employed in a synergistic weight ratio. The skilled person is able to find out the synergistic weight ratios for the present invention by routine methods. The skilled person understands that these ratios refer to the ratio within a combined-formulation as well as to the calculative ratio of the recombinant exosporium-producing *Bacillus* cells described herein and the at least one further particular biological control agent disclosed herein when both components are applied as mono-formulations to a plant to be treated. The skilled person can calculate this ratio by simple mathematics since the volume and the amount of the recombinant exosporium-producing *Bacillus* cells and the at least one further particular biological control agent disclosed herein, respectively, in a mono-formulation is known to the skilled person.

The ratio can be calculated based on the amount of the at least one further particular biological control agent disclosed herein, at the time point of applying said component of a combination according to the invention to a plant or plant part and the amount of the recombinant exosporium-producing *Bacillus* cells shortly prior (e.g., 48 h, 24 h, 12 h, 6 h, 2 h, 1 h) or at the time point of applying said component of a combination according to the invention to a plant or plant part.

The application of the recombinant exosporium-producing *Bacillus* cells and the at least one further particular biological control agent disclosed herein to a plant or a plant part can take place simultaneously or at different times as long as both components are present on or in the plant after the application(s). In cases where the recombinant exosporium-producing *Bacillus* cells and further particular biological control agent disclosed herein are applied at different times and the further particular biological control agent disclosed herein is applied prior to the recombinant exosporium-producing *Bacillus* cells, the skilled person can determine the concentration of further particular biological control agent disclosed herein on/in a plant by chemical analysis known in the art, at the time point or shortly before the time point of applying the recombinant exosporium-producing *Bacillus* cells. Vice versa, when the recombinant exosporium-producing *Bacillus* cells is applied to a plant first, the concentration of the recombinant exosporium-producing *Bacillus* cells can be determined using tests which are also known in the art, at the time point or shortly before the time point of applying the further particular biological control agent disclosed herein.

In particular, in one embodiment the synergistic weight ratio of the recombinant exosporium-producing *Bacillus* cells (i.e., the unformulated spore preparation) and the at least one further particular biological control agent disclosed herein lies in the range of 1:1000 to 1000:1; in the range of 1:500 to 500:1; in the range of 1:300 to 500:1. Additional ratios are between 20:1 and 1:20, such as 10:1, 5:1 or 2:1. In embodiments in which the biological control agent is *Bacillus*-based the weight to weight ratio should be applied to the unformulated *Bacillus* spore preparation. In one aspect of this embodiment, the spore preparations of both the recombinant exosporium-producing *Bacillus* cells and the *Bacillus*-based biological control agent is dried spore preparation containing at least about $1\times10^4$ cfu/g, at least about $1\times10^5$ cfu/g, at least about $1\times10^6$ cfu/g at least about $1\times10^7$ cfu/g, at least about $1\times10^8$ cfu/g, at least about $1\times10^9$ cfu/g, at least about $1\times10^{10}$ cfu/g, and at least about $1\times10^{11}$ cfu/g. In another embodiment the colony forming unit to colony forming unit ratio of recombinant exosporium-producing *Bacillus* cells and the *Bacillus*-based particular biological control agent described herein lies in the range of 1:100,000 to 100,000 to 1, in the range of 1:10,000 to 10,000:1, in the range of 1:1000 to 1000:1, in the range of 1:500 to 500:1, in the range of 1:100 to 100:1, in the range of 1:10 to 10:1, in the range of 1:5 to 5:1, and in the range of 1:1.

In one embodiment of the present invention, the concentration of the recombinant exosporium-producing *Bacillus cereus* family member-based biological control agent after dispersal is at least 50 g/ha, such as 50-7500 g/ha, 50-2500 g/ha, 50-1500 g/ha; at least 250 g/ha (hectare), at least 500 g/ha or at least 800 g/ha.

The application rate of composition to be employed or used according to the present invention may vary. The skilled person is able to find the appropriate application rate by way of routine experiments.

In another aspect of the present invention a seed treated with the composition as described above is provided.

The control of insects, mites, nematodes and/or phytopathogens by treating the seed of plants has been known for a long time and is a subject of continual improvements. Nevertheless, the treatment of seed entails a series of problems which cannot always be solved in a satisfactory manner. Thus, it is desirable to develop methods for protecting the seed and the germinating plant that remove the need for, or at least significantly reduce, the additional delivery of crop protection compositions in the course of storage, after sowing or after the emergence of the plants. It is desirable, furthermore, to optimize the amount of active ingredient employed in such a way as to provide the best-possible protection to the seed and the germinating plant from attack by insects, mites, nematodes and/or phytopathogens, but without causing damage to the plant itself by the active ingredient employed. In particular, methods for treating seed ought also to take into consideration the intrinsic insecticidal and/or nematicidal properties of pest-resistant or pest-tolerant transgenic plants, in order to achieve optimum protection of the seed and of the germinating plant with a minimal use of crop protection compositions.

The present invention therefore also relates in particular to a method for protecting seed and germinating plants from attack by pests, by treating the seed with the recombinant exosporium-producing *Bacillus* cells as defined above and at least one further biological control agent selected from particular microorganisms disclosed herein and/or a mutant of a specific strain of microorganism disclosed herein having all identifying characteristics of the respective strain, and/or at least one metabolite produced by the respective strain that exhibits activity against insects, mites, nematodes and/or phytopathogens and optionally at least one fungicide and/or optionally at least one insecticide of the invention. The method of the invention for protecting seed and germinating plants from attack by pests encompasses a method in which the seed is treated simultaneously in one operation with the recombinant exosporium-producing *Bacillus* cells and the at least one further particular biological control agent described herein, and optionally the at least one fungicide and/or the at least one insecticide. It also encompasses a method in which the seed is treated at different times with the recombinant exosporium-producing *Bacillus* cells and the at least one further particular biological control agent disclosed herein, and optionally the at least one fungicide and/or the at least one insecticide.

The invention likewise relates to the use of the composition of the invention for treating seed for the purpose of protecting the seed and the resultant plant against insects, mites, nematodes and/or phytopathogens.

The invention also relates to seed which at the same time has been treated with a the recombinant exosporium-producing *Bacillus* cells and at least one further particular biological control agent described herein, and optionally at least one fungicide and/or the at least one insecticide. The invention further relates to seed which has been treated at different times with the recombinant exosporium-producing *Bacillus* cells and the at least one further particular biological control agent disclosed herein and optionally the at least one fungicide and/or the at least one insecticide. In the case of seed which has been treated at different times with the recombinant exosporium-producing *Bacillus* cells and the at least one further particular biological control agent disclosed herein, and optionally the at least one fungicide and/or the at least one insecticide, the individual active ingredients in the composition of the invention may be present in different layers on the seed.

Furthermore, the invention relates to seed which, following treatment with the composition of the invention, is subjected to a film-coating process in order to prevent dust abrasion of the seed.

One of the advantages of the present invention is that, owing to the particular systemic properties of the compositions of the invention, the treatment of the seed with these compositions provides protection from insects, mites, nematodes and/or phytopathogens not only to the seed itself but also to the plants originating from the seed, after they have emerged. In this way, it may not be necessary to treat the crop directly at the time of sowing or shortly thereafter.

A further advantage is to be seen in the fact that, through the treatment of the seed with composition of the invention, germination and emergence of the treated seed may be promoted.

It is likewise considered to be advantageous composition of the invention may also be used, in particular, on transgenic seed.

It is also stated that the composition of the invention may be used in combination with agents of the signalling technology, as a result of which, for example, colonization with symbionts is improved, such as rhizobia, mycorrhiza and/or endophytic bacteria, for example, is enhanced, and/or nitrogen fixation is optimized.

The compositions of the invention are suitable for protecting seed of any variety of plant which is used in agriculture, in greenhouses, in forestry or in horticulture. More particularly, the seed in question is that of cereals (e.g., wheat, barley, rye, oats and millet), maize, cotton, soybeans, rice, potatoes, sunflower, coffee, tobacco, canola, oilseed rape, beets (e.g., sugar beet and fodder beet), peanuts, vegetables (e.g., tomato, cucumber, bean, brassicas, onions and lettuce), fruit plants, lawns and ornamentals. Particularly important is the treatment of the seed of cereals (such as wheat, barley, rye and oats) maize, soybeans, cotton, canola, oilseed rape and rice.

As already mentioned above, the treatment of transgenic seed with the composition of the invention is particularly important. The seed in question here is that of plants which generally contain at least one heterologous gene that controls the expression of a polypeptide having, in particular, insecticidal and/or nematicidal properties. These heterologous genes in transgenic seed may come from microorganisms such as *Bacillus, Rhizobium, Pseudomonas, Serratia, Trichoderma, Clavibacter, Glomus* or *Gliocladium*. The present invention is particularly suitable for the treatment of transgenic seed which contains at least one heterologous gene from *Bacillus* sp. With particular preference, the heterologous gene in question comes from *Bacillus thuringiensis*.

For the purposes of the present invention, the composition of the invention is applied alone or in a suitable formulation to the seed. The seed is preferably treated in a condition in which its stability is such that no damage occurs in the course of the treatment. Generally speaking, the seed may be treated at any point in time between harvesting and sowing. Typically, seed is used which has been separated from the plant and has had cobs, hulls, stems, husks, hair or pulp removed. Thus, for example, seed may be used that has been harvested, cleaned and dried to a moisture content of less than 15% by weight. Alternatively, seed can also be used that after drying has been treated with water, for example, and then dried again.

When treating seed it is necessary, generally speaking, to ensure that the amount of the composition of the invention, and/or of other additives, that is applied to the seed is selected such that the germination of the seed is not adversely affected, and/or that the plant which emerges from the seed is not damaged. This is the case in particular with active ingredients which may exhibit phytotoxic effects at certain application rates.

The compositions of the invention can be applied directly, in other words without comprising further components and without having been diluted. As a general rule, it is preferable to apply the compositions in the form of a suitable formulation to the seed. Suitable formulations and methods for seed treatment are known to the skilled person and are described in, for example, the following documents: U.S. Pat. Nos. 4,272,417 A; 4,245,432 A; 4,808,430 A; 5,876,739 A; U.S. Patent Publication No. 2003/0176428 A1; WO 2002/080675 A1; WO 2002/028186 A2.

The combinations which can be used in accordance with the invention may be converted into the customary seed-dressing formulations, such as solutions, emulsions, suspensions, powders, foams, slurries or other coating compositions for seed, and also ULV formulations.

These formulations are prepared in a known manner, by mixing composition with customary adjuvants, such as, for example, customary extenders and also solvents or diluents, colorants, wetters, dispersants, emulsifiers, antifoams, preservatives, secondary thickeners, stickers, gibberellins, and also water.

Colorants which may be present in the seed-dressing formulations which can be used in accordance with the invention include all colorants which are customary for such purposes. In this context it is possible to use not only pigments, which are of low solubility in water, but also water-soluble dyes. Examples include the colorants known under the designations Rhodamin B, C.I. Pigment Red 112 and C.I. Solvent Red 1.

Wetters which may be present in the seed-dressing formulations which can be used in accordance with the invention include all of the substances which promote wetting and which are customary in the formulation of active agrochemical ingredients. Use may be made preferably of alkylnaphthalenesulphonates, such as diisopropyl- or diisobutyl-naphthalenesulphonates.

Dispersants and/or emulsifiers which may be present in the seed-dressing formulations which can be used in accordance with the invention include all of the nonionic, anionic and cationic dispersants that are customary in the formulation of active agrochemical ingredients. Use may be made preferably of nonionic or anionic dispersants or of mixtures of nonionic or anionic dispersants. Suitable nonionic dispersants are, in particular, ethylene oxide-propylene oxide block polymers, alkylphenol polyglycol ethers and also tristryrylphenol polyglycol ethers, and the phosphated or sulphated derivatives of these. Suitable anionic dispersants are, in particular, lignosulphonates, salts of polyacrylic acid, and arylsulphonate-formaldehyde condensates.

Antifoams which may be present in the seed-dressing formulations which can be used in accordance with the invention include all of the foam inhibitors that are customary in the formulation of active agrochemical ingredients. Use may be made preferably of silicone antifoams and magnesium stearate.

Preservatives which may be present in the seed-dressing formulations which can be used in accordance with the invention include all of the substances which can be employed for such purposes in agrochemical compositions. Examples include dichlorophen and benzyl alcohol hemiformal.

Secondary thickeners which may be present in the seed-dressing formulations which can be used in accordance with the invention include all substances which can be used for such purposes in agrochemical compositions. Those contemplated with preference include cellulose derivatives, acrylic acid derivatives, xanthan, modified clays and highly disperse silica.

Stickers which may be present in the seed-dressing formulations which can be used in accordance with the invention include all customary binders which can be used in seed-dressing products. Preferred mention may be made of polyvinylpyrrolidone, polyvinyl acetate, polyvinyl alcohol and tylose.

Gibberellins which may be present in the seed-dressing formulations which can be used in accordance with the invention include preferably the gibberellins A1, A3 (=gibberellic acid), A4 and A7, with gibberellic acid being used with particular preference. The gibberellins are known (cf. R. Wegler, "Chemie der Pflanzenschutz-und Schädlingsbekämpfungsmittel", Volume 2, Springer Verlag, 1970, pp. 401-412).

The seed-dressing formulations which can be used in accordance with the invention may be used, either directly or after prior dilution with water, to treat seed of any of a wide variety of types. Accordingly, the concentrates or the preparations obtainable from them by dilution with water may be employed to dress the seed of cereals, such as wheat, barley, rye, oats and triticale, and also the seed of maize, rice, oilseed rape, peas, beans, cotton, sunflowers and beets, or else the seed of any of a very wide variety of vegetables. The seed-dressing formulations which can be used in accordance with the invention, or their diluted preparations, may also be used to dress seed of transgenic plants. In that case, additional synergistic effects may occur in interaction with the substances formed through expression.

For the treatment of seed with the seed-dressing formulations which can be used in accordance with the invention, or with the preparations produced from them by addition of water, suitable mixing equipment includes all such equipment which can typically be employed for seed dressing. More particularly, the procedure when carrying out seed dressing is to place the seed in a mixer, to add the particular desired amount of seed-dressing formulations, either as such or following dilution with water beforehand, and to carry out mixing until the distribution of the formulation on the seed is uniform. This may be followed by a drying operation.

The application rate of the seed-dressing formulations which can be used in accordance with the invention may be varied within a relatively wide range. It is guided by the particular amount of the recombinant exosporium-producing *Bacillus* cells and the at least one further particular biological control agent described herein in the formulations, and by the seed. The application rates in the case of the composition are situated generally at between 0.001 and 50 g per kilogram of seed, preferably between 0.01 and 15 g per kilogram of seed.

Furthermore, the composition according to the present invention preferably has potent microbicidal activity and can be used for control of unwanted microorganisms, such as fungi and bacteria, in crop protection and in the protection of materials.

The invention also relates to a method for controlling unwanted microorganisms, characterized in that the inventive composition is applied to the phytopathogenic fungi, phytopathogenic bacteria and/or their habitat.

Fungicides can be used in crop protection for control of phytopathogenic fungi. They are characterized by an outstanding efficacy against a broad spectrum of phytopathogenic fungi, including soilborne pathogens, which are in particular members of the classes Plasmodiophoromycetes, Peronosporomycetes (Syn. Oomycetes), Chytridiomycetes, Zygomycetes, Ascomycetes, Basidiomycetes and Deuteromycetes (Syn. Fungi imperfecti). Some fungicides are systemically active and can be used in plant protection as foliar, seed dressing or soil fungicide. Furthermore, they are suitable for combating fungi, which inter alia infest wood or roots of plant.

Bactericides can be used in crop protection for control of Pseudomonadaceae, Rhizobiaceae, Enterobacteriaceae, Corynebacteriaceae and Streptomycetaceae.

Non-limiting examples of pathogens of fungal diseases which can be treated in accordance with the invention include:

- diseases caused by powdery mildew pathogens, for example Blumeria species, for example Blumeria *graminis; Podosphaera* species, for example *Podosphaera leucotricha*; Sphaerotheca species, for example *Sphaerotheca fuliginea; Uncinula* species, for example *Uncinula necator,*
- diseases caused by rust disease pathogens, for example *Gymnosporangium* species, for example *Gymnosporangium sabinae; Hemileia* species, for example *Hemileia vastatrix; Phakopsora* species, for example *Phakopsora pachyrhizi* and *Phakopsora meibomiae; Puccinia* species, for example *Puccinia* recondite, P. triticina, *P. graminis* or *P. striiformis* or *P. hordei, Uromyces* species, for example *Uromyces appendiculatus;*
- diseases caused by pathogens from the group of the Oomycetes, for example Albugo species, for example *Algubo candida; Bremia* species, for example *Bremia lactucae; Peronospora* species, for example *Peronospora pisi, P. parasitica* or *P. brassicae; Phytophthora* species, for example *Phytophthora infestans*; Plasmopara species, for example Plasmopara viticola; *Pseudoperonospora* species, for example *Pseudoperonospora humuli* or *Pseudoperonospora cubensis; Pythium* species, for example *Pythium ultimum;*
- leaf blotch diseases and leaf wilt diseases caused, for example, by *Alternaria* species, for example *Alternaria solani; Cercospora* species, for example *Cercospora beticola*; Cladiosporium species, for example Cladiosporium cucumerinum; *Cochliobolus* species, for example *Cochliobolus sativus* (conidia form: *Drechslera*, Syn: *Helminthosporium*), *Cochliobolus miyabeanus; Colletotrichum* species, for example *Colletotrichum lindemuthanium; Cycloconium* species, for example Cycloconium oleaginum; *Diaporthe* species, for example *Diaporthe citri, Elsinoe* species, for example *Elsinoe fawcettii*, Gloeosporium species, for example Gloeosporium laeticolor, *Glomerella* species, for example *Glomerella cingulata; Guignardia* species, for example *Guignardia* bidwelli, *Leptosphaeria* species, for example *Leptosphaeria maculans, Leptosphaeria nodorum; Magnaporthe* species, for example *Magnaporthe grisea; Microdochium* species, for example *Microdochium nivale; Mycosphaerella* species, for example *Mycosphaerella graminicola, M. arachidicola* and *M. fijiensis; Phaeosphaeria* species, for example *Phaeosphaeria nodorum; Pyrenophora* species, for example *Pyrenophora teres, Pyrenophora tritici repentis; Ramularia* species, for example *Ramularia collo-cygni, Ramularia areola; Rhynchosporium* species, for example *Rhynchosporium secalis; Septoria* species, for example *Septoria* apii, *Septoria lycopersii; Typhula* species, for example *Typhula incarnata; Venturia* species, for example *Venturia inaequalis;*
- root and stem diseases caused, for example, by *Corticium* species, for example *Corticium graminearum; Fusarium* species, for example *Fusarium oxysporum; Gaeumannomyces* species, for example *Gaeumannomyces graminis; Rhizoctonia* species, such as, for example *Rhizoctonia solani; Sarocladium* diseases caused for example by *Sarocladium oryzae; Sclerotium* diseases caused for example by *Sclerotium oryzae; Tapesia* species, for example *Tapesia acuformis; Thielaviopsis* species, for example *Thielaviopsis basicola;*
- ear and panicle diseases (including corn cobs) caused, for example, by *Altemaria* species, for example *Alternaria* spp.; *Aspergillus* species, for example *Aspergillus flavus; Cladosporium* species, for example *Cladosporium* cladosporioides; *Claviceps* species, for example *Claviceps purpurea; Fusarium* species, for example *Fusarium culmorum; Gibberella* species, for example *Gibberella zeae; Monographella* species, for example *Monographella nivalis; Septoria* species, for example *Septoria nodorum;*
- diseases caused by smut fungi, for example *Sphacelotheca* species, for example *Sphacelotheca reiliana; Tilletia* species, for example *Tilletia caries, T. controversa; Urocystis* species, for example *Urocystis occulta; Ustilago* species, for example *Ustilago nuda, U. nuda tritici;*
- fruit rot caused, for example, by *Aspergillus* species, for example *Aspergillus flavus; Botrytis* species, for example *Botrytis cinerea; Penicillium* species, for example *Penicillium expansum* and *P. purpurogenum;*

*Sclerotinia* species, for example *Sclerotinia sclerotiorum*; *Verticilium* species, for example *Verticilium alboatrum*;

seed and soilborne decay, mould, wilt, rot and damping-off diseases caused, for example, by *Alternaria* species, caused for example by *Alternaria brassicicola*; *Aphanomyces* species, caused for example by *Aphanomyces euteiches*; *Ascochyta* species, caused for example by *Ascochyta lentis*; *Aspergillus* species, caused for example by *Aspergillus flavus*; *Cladosporium* species, caused for example by *Cladosporium herbarum*; *Cochliobolus* species, caused for example by *Cochliobolus sativus*; (*Conidiaform: Drechslera, Bipolaris* Syn: *Helminthosporium*); *Colletotrichum* species, caused for example by *Colletotrichum coccodes*; *Fusarium* species, caused for example by *Fusarium culmorum*; *Gibberella* species, caused for example by *Gibberella zeae*; *Macrophomina* species, caused for example by *Macrophomina phaseolina*; *Monographella* species, caused for example by *Monographella nivalis*; *Penicillium* species, caused for example by *Penicillium expansum*; *Phoma* species, caused for example by *Phoma* lingam; *Phomopsis* species, caused for example by *Phomopsis sojae*; *Phytophthora* species, caused for example by *Phytophthora cactorum*; *Pyrenophora* species, caused for example by *Pyrenophora graminea*; *Pyricularia* species, caused for example by *Pyricularia oryzae*; *Pythium* species, caused for example by *Pythium ultimum*; *Rhizoctonia* species, caused for example by *Rhizoctonia solani, Rhizopus* species, caused for example by *Rhizopus oryzae*; *Sclerotium* species, caused for example by *Sclerotium rolfsii*; *Septoria* species, caused for example by *Septoria nodorum*; *Typhula* species, caused for example by *Typhula incarnata*; *Verticillium* species, caused for example by *Verticillium dahliae*;

cancers, galls and witches' broom caused, for example, by *Nectria* species, for example *Nectria galligena*;

wilt diseases caused, for example, by *Monilinia* species, for example *Monilinia laxa*;

leaf blister or leaf curl diseases caused, for example, by *Exobasidium* species, for example *Exobasidium vexans*;

*Taphrina* species, for example *Taphrina deformans*;

decline diseases of wooden plants caused, for example, by Esca disease, caused for example by *Phaemoniella clamydospora, Phaeoacremonium aleophilum* and *Fomitiporia mediterranea*; *Eutypa* dyeback, caused for example by *Eutypa lata*; *Ganoderma* diseases caused for example by *Ganoderma boninense*; *Rigidoporus* diseases caused for example by *Rigidoporus lignosus*;

diseases of flowers and seeds caused, for example, by *Botrytis* species, for example *Botrytis cinerea*;

diseases of plant tubers caused, for example, by *Rhizoctonia* species, for example *Rhizoctonia solani, Helminthosporium* species, for example *Helminthosporium solani*;

Club root caused, for example, by *Plasmodiophora* species, for example *Plamodiophora brassicae*;

diseases caused by bacterial pathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soya beans can be controlled with preference:

Fungal diseases on leaves, stems, pods and seeds caused, for example, by *Alternaria* leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

The inventive compositions can be used for curative or protective/preventive control of phytopathogenic fungi. The invention therefore also relates to curative and protective methods for controlling phytopathogenic fungi by the use of the inventive composition, which is applied to the seed, the plant or plant parts, the fruit or the soil in which the plants grow.

The fact that the composition is well tolerated by plants at the concentrations required for controlling plant diseases allows the treatment of above-ground parts of plants, of propagation stock and seeds, and of the soil.

According to the invention all plants and plant parts can be treated. By plants is meant all plants and plant populations such as desirable and undesirable wild plants, cultivars and plant varieties (whether or not protectable by plant variety or plant breeder's rights). Cultivars and plant varieties can be plants obtained by conventional propagation and breeding methods which can be assisted or supplemented by one or more biotechnological methods such as by use of double haploids, protoplast fusion, random and directed mutagenesis, molecular or genetic markers or by bioengineering and genetic engineering methods. By plant parts is meant all above ground and below ground parts and organs of plants such as shoot, leaf, blossom and root, whereby for example leaves, needles, stems, branches, blossoms, fruiting bodies, fruits and seed as well as roots, corms and rhizomes are listed. Crops and vegetative and generative propagating material, for example cuttings, corms, rhizomes, runners and seeds also belong to plant parts.

The inventive composition, when it is well tolerated by plants, has favourable homeotherm toxicity and is well tolerated by the environment, is suitable for protecting plants and plant organs, for enhancing harvest yields, for improving the quality of the harvested material. It can preferably be used as crop protection composition. It is active against normally sensitive and resistant species and against all or some stages of development.

Plants which can be treated in accordance with the invention include the following main crop plants: maize, soya bean, alfalfa, cotton, sunflower, *Brassica* oil seeds such as *Brassica napus* (e.g., canola, rapeseed), *Brassica rapa, B. juncea* (e.g., (field) mustard) and *Brassica carinata, Arecaceae* sp. (e.g., oilpalm, coconut), rice, wheat, sugar beet, sugar cane, oats, rye, barley, millet and sorghum, triticale, flax, nuts, grapes and vine and various fruit and vegetables from various botanic taxa, e.g., *Rosaceae* sp. (e.g., pome fruits such as apples and pears, but also stone fruits such as apricots, cherries, almonds, plums and peaches, and berry fruits such as strawberries, raspberries, red and black currant and gooseberry), *Ribesioidae* sp., *Juglandaceae* sp., *Betulaceae* sp., *Anacardiaceae* sp., *Fagaceae* sp., *Moraceae* sp., *Oleaceae* sp. (e.g., olive tree), *Actinidaceae* sp., *Lauraceae* sp. (e.g., avocado, cinnamon, camphor), *Musaceae* sp. (e.g., banana trees and plantations), *Rubiaceae* sp. (e.g., coffee), *Theaceae* sp. (e.g., tea), *Sterculiceae* sp., *Rutaceae* sp. (e.g., lemons, oranges, mandarins and grapefruit); *Solanaceae* sp. (e.g., tomatoes, potatoes, peppers, capsicum, aubergines, tobacco), *Liliaceae* sp., *Compositae* sp. (e.g., lettuce, artichokes and chicory—including root chicory, endive or common chicory), *Umbelliferae* sp. (e.g., carrots, parsley, celery and celeriac), *Cucurbitaceae* sp. (e.g., cucumbers—including gherkins, pumpkins, watermelons, calabashes and melons), *Alliaceae* sp. (e.g., leeks and onions), *Cruciferae* sp. (e.g., white cabbage, red cabbage, broccoli, cauliflower, Brussels sprouts, pak choi, kohlrabi, radishes, horseradish, cress and chinese cabbage), *Leguminosae* sp. (e.g., peanuts, peas, lentils and beans—e.g., common beans and broad beans), *Chenopodiaceae* sp. (e.g., Swiss chard, fodder beet, spinach, beetroot), *Linaceae* sp. (e.g., hemp), *Cannabeacea* sp. (e.g., cannabis), *Malvaceae* sp. (e.g., okra, cocoa), *Papaveraceae* (e.g., poppy), *Asparagaceae* (e.g., asparagus); useful plants and ornamental plants in the garden and woods including turf, lawn, grass and *Stevia rebaudiana*; and in each case genetically modified types of these plants.

Depending on the plant species or plant cultivars, their location and growth conditions (soils, climate, vegetation period, diet), using or employing the composition according to the present invention the treatment according to the invention may also result in super-additive ("synergistic") effects. Thus, for example, by using or employing inventive composition in the treatment according to the invention, reduced application rates and/or a widening of the activity spectrum and/or an increase in the activity better plant growth, increased tolerance to high or low temperatures, increased tolerance to drought or to water or soil salt content, increased flowering performance, easier harvesting, accelerated maturation, higher harvest yields, bigger fruits, larger plant height, greener leaf color, earlier flowering, higher quality and/or a higher nutritional value of the harvested products, higher sugar concentration within the fruits, better storage stability and/or processability of the harvested products are possible, which exceed the effects which were actually to be expected.

At certain application rates of the inventive composition in the treatment according to the invention may also have a strengthening effect in plants. The defense system of the plant against attack by unwanted phytopathogenic fungi and/or microorganisms and/or viruses is mobilized. Plant-strengthening (resistance-inducing) substances are to be understood as meaning, in the present context, those substances or combinations of substances which are capable of stimulating the defense system of plants in such a way that, when subsequently inoculated with unwanted phytopathogenic fungi and/or microorganisms and/or viruses, the treated plants display a substantial degree of resistance to these phytopathogenic fungi and/or microorganisms and/or viruses. Thus, by using or employing composition according to the present invention in the treatment according to the invention, plants can be protected against attack by the abovementioned pathogens within a certain period of time after the treatment. The period of time within which protection is effected generally extends from 1 to 10 days, preferably 1 to 7 days, after the treatment of the plants with the active compounds.

Plants and plant cultivars which are also preferably to be treated according to the invention are resistant against one or more biotic stresses, i.e., said plants show a better defense against animal and microbial pests, such as against nematodes, insects, mites, phytopathogenic fungi, bacteria, viruses and/or viroids.

Plants and plant cultivars which may also be treated according to the invention are those plants which are resistant to one or more abiotic stresses, i.e., that already exhibit an increased plant health with respect to stress tolerance. Abiotic stress conditions may include, for example, drought, cold temperature exposure, heat exposure, osmotic stress, flooding, increased soil salinity, increased mineral exposure, ozon exposure, high light exposure, limited availability of nitrogen nutrients, limited availability of phosphorus nutrients, shade avoidance. Preferably, the treatment of these plants and cultivars with the composition of the present invention additionally increases the overall plant health (cf. above).

Plants and plant cultivars which may also be treated according to the invention, are those plants characterized by enhanced yield characteristics, i.e., that already exhibit an increased plant health with respect to this feature. Increased yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation.

Yield can furthermore be affected by improved plant architecture (under stress and non-stress conditions), including but not limited to, early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability. Preferably, the treatment of these plants and cultivars with the composition of the present invention additionally increases the overall plant health (cf. above).

Plants that may be treated according to the invention are hybrid plants that already express the characteristic of heterosis or hybrid vigor which results in generally higher yield, vigor, health and resistance towards biotic and abiotic stress factors. Such plants are typically made by crossing an inbred male-sterile parent line (the female parent) with another inbred male-fertile parent line (the male parent). Hybrid seed is typically harvested from the male sterile plants and sold to growers. Male sterile plants can sometimes (e.g., in corn) be produced by detasseling, i.e., the mechanical removal of the male reproductive organs (or males flowers) but, more typically, male sterility is the result of genetic determinants in the plant genome. In that case, and especially when seed is the desired product to be harvested from the hybrid plants it is typically useful to ensure that male fertility in the hybrid plants is fully restored. This can be accomplished by ensuring that the male parents have appropriate fertility restorer genes which are capable of restoring the male fertility in hybrid plants that contain the genetic determinants responsible for male-sterility. Genetic determinants for male sterility may be located in the cytoplasm. Examples of cytoplasmic male sterility (CMS) were for instance described in *Brassica* species. However, genetic determinants for male sterility can also be located in the nuclear genome. Male sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e., plants made tolerant to one or more given herbicides. Such plants can be obtained either by genetic transformation, or by selection of plants containing a mutation imparting such herbicide tolerance.

The following non-limiting examples are provided to further illustrate the present invention.

EXAMPLES

Example 1: Formula for the Efficacy of the Combination of Multiple Active Ingredients A synergistic effect of active ingredients is present when the activity of the active ingredient combinations exceeds the total of the activities of the active ingredients when applied individually. The expected activity for a given combination of two active ingredients can be calculated as follows (cf. Colby, S. R., "Calculating Synergistic and Antagonistic Responses of Herbicide Combinations," Weeds 1967, 15, 20-22):

If
X is the efficacy when active ingredient A is applied at an application rate of m ppm (or g/ha),
Y is the efficacy when active ingredient B is applied at an application rate of n ppm (or g/ha),
E is the efficacy when the active ingredients A and B are applied at application rates of m and n ppm (or g/ha), respectively, and
then $$E = X + Y - \frac{X \cdot Y}{100}$$

If the actual activity exceeds the calculated value, then the activity of the combination is superadditive, i.e., a synergistic effect exists. In this case, the efficacy which was actually observed must be greater than the value for the expected efficacy (E) calculated from the above-mentioned formula.

For instance, the formula and analysis can be applied to an evaluation of plant growth promotion. Such an assay is evaluated several days after the applications to plants. 100% means plant weight which corresponds to that of the untreated control plant. Efficacy means in this case the additional % of plant weight in comparison to that of the untreated control. For example, a treatment that resulted in plant weights that were 120% compared to the untreated control plant would have an efficacy of 20%. If the plant growth promotion effect for the combination (i.e., the observed efficacy for % shoot weights of plants treated with the combination) exceeds the calculated value, then the activity of the combination is superadditive, i.e., a synergistic effect exists.

The formula and analysis can also be used to evaluate synergy in disease control assays. The degree of efficacy expressed in % is denoted. 0% means an efficacy which corresponds to that of the control while an efficacy of 100% means that no disease is observed.

If the actual insecticidal or fungicidal activity exceeds the calculated value, then the activity of the combination is superadditive, i.e., a synergistic effect exists. In this case, the efficacy which is actually observed must be greater than the value for the expected efficacy (E) calculated from the above-mentioned formula.

A further way of demonstrating a synergistic effect is the method of Tammes (cf. "Isoboles, A Graphic Representation of Synergism in Pesticides," in Neth. J. Plant Path., 1964, 70, 73-80).

Example 2: Plant Growth Promotion with *Bacillus subtilis* QST713 and Recombinant *Bacillus thuringiensis* Cells Expressing Phospholipase C Experiments were conducted to analyze efficacy of a combination of *Bacillus subtilis* QST713-based product and a fermentation product of recombinant *Bacillus thuringiensis* cells expressing phospholipase C ("BEPC"). Maize seeds were grown in sterile mixture of synthetic media and sand in small three-inch square pots on light racks in a plant growth room at 25-28° C. and 50% humidity for about 14 days. Two seeds were planted in each pot. At planting, the growing media in each pot was drenched with the treatments described below. After 14 days, plants were measured for whole plant biomass. In some experiments, roots were analyzed using the WinRhizo Root scanner. In all tables throughout these Examples, UTC refers to untreated control. "Calculated" refers to the expected effect calculated using the above-described Colby equation and "Efficacy" refers to the actual effect observed.

The SERENADE® ASO product was diluted in water (1% and 5% volume to volume) and the diluted solution was used to drench the growing media. The application rate of SERENADE® ASO refers to the amount of *Bacillus subtilis* QST713 (i.e., spore preparation) contained in the product SERENADE® ASO, which is 1.34%. The formulated product has a minimum spore concentration of $1\times10^9$ cfu/g.

A recombinant *Bacillus cereus* family member (*Bacillus thuringiensis* BT013A) expressing phospholipase C on its exosporium (BEPC) was generated as follows. To generate plasmids for expression of fusion proteins in *Bacillus cereus* family members, PCR fragments were generated that encoded the BclA promoter (SEQ ID NO: 85), a methionine start codon, and amino acids 20-35 of BclA (SEQ ID NO: 1) followed by a six alanine linker sequence fused in frame to *Bacillus thuringiensis* BT013A phospholipase C (SEQ ID NO: 108). These PCR fragments were digested with XhoI and ligated into the SalI site of the pSUPER plasmid to generate the plasmids pSUPER-BclA 20-35-Phospholipase. The pSUPER plasmid was generated through fusion of the pUC57 plasmid (containing an ampicillin resistance cassette) with the pBC16-1 plasmid from *Bacillus* (containing a tetracycline resistance). This 5.5 kbp plasmid can replicate in both *E. coli* and *Bacillus* spp. The pSUPER-BclA 20-35-Phospholipase plasmids were transformed into and propagated in dam methylase negative *E. coli* strains and finally were transformed into *Bacillus thuringiensis* BT013A.

To obtain whole broth cultures of BEPC, 15 ml conicals containing brain heart infusion media (BHI) were inoculated with BEPC and grown for 7-8 hours at around 30° C. at a shaker setting of 300 rpm. The next day, 250 μl aliquots from each flask were inoculated into 250 mL flasks containing 50 mL of a yeast extract-based media and grown at about 30° C. After approximately 2 days of incubation, when sporulation was at least 95% completed, the culture broth was harvested and colony forming units calculated. The fermentation broth was diluted to 5% in 50 mL water and the following colony forming units applied to each pot.

TABLE 3

| Treatment | Application Rate PPM and/or CFU/pot | Whole Plant Biomass (g) | Found % | Efficacy % | Calculated % |
|---|---|---|---|---|---|
| UTC | | 3.23 | 100 | | |
| SERENADE ® ASO 5% | 703 $2.62 \times 10^9$ | 4.71 | 146 | 46 | |
| *Bacillus* expressing phospholipase C (BEPC) 5% | $7 \times 10^8$ CFU/pot | 3.83 | 118 | 18 | |
| SERENADE ® ASO 5% + BEPC | $2.62 \times 10^9$ + $7 \times 10^8$ | 5.33 | 165 | 65 | 55.72 |

The experiment was repeated as above but with a 1% dilution of the SERENADE® ASO product. Results are shown in Table 4, below.

TABLE 4

| Treatment | Application Rate | Whole Plant Biomass (g) | Found % | Efficacy % | Calculated % |
|---|---|---|---|---|---|
| UTC | | 3.22 | 100 | | |
| SERENADE ® ASO 1% | 140.7 PPM $5.24 \times 10^8$ CFU/pot | 3.62 | 112 | 12 | |
| BEPC | $7 \times 10^8$ CFU/pot | 3.76 | 117 | 17 | |
| SERENADE ® ASO 1% + BEPC | $5.24 \times 10^8$ CFU/pot + $7 \times 10^8$ CFU/pot | 4.26 | 132 | 32 | 26.96 |

Results of root volume measurements using the WinRhizo root scanner are shown in Table 5.

TABLE 5

| | Root Volume Average | % Found | % Efficacy | % Calculated |
|---|---|---|---|---|
| UTC | 5.259 | 100.0 | 0.0 | |
| SERENADE ® ASO 1% | 6.282 | 119.5 | 19.5 | |
| BEPC 5% | 6.249 | 118.8 | 18.8 | |
| Ser 1% and BEPC 5% | 9.318 | 177.2 | 77.2 | 34.6 |

Results indicate a superadditive plant yield effect when combining SERENADE® ASO and BEPC.

Example 3: Plant Growth Promotion with *Bacillus subtilis* QST713 and Recombinant *Bacillus thuringiensis* Cells Expressing Endoglucanase Experiments similar to those in Example 2 were conducted using a recombinant *Bacillus thuringiensis* cells expressing endoglucanase (SEQ ID NO: 107), referred to in these examples as BEE. Whole broth cultures of BEE were created as described above, except that endoglucanase (SEQ ID NO: 107), rather than phosphpolipase, was used. Effects on plant yield of combinations of BEE with SERENADE® ASO are shown in the tables below.

TABLE 6

| Treatment | Application Rate | Whole Plant Biomass (g) | Found % | Efficacy % | Calculated % |
|---|---|---|---|---|---|
| UTC | | 3.23 | 100 | | |
| SERENADE ® ASO 5% | 703 PPM $2.62 \times 10^9$ CFU/pot | 4.71 | 146 | 46 | |
| BEE 5% | $7.85 \times 10^8$ CFU/pot | 3.7 | 114 | 14 | |
| SERENADE ® ASO 5% + BEE 5% | $2.62 \times 10^9$ CFU/pot + $7.85 \times 10^8$ CFU/pot | 5.89 | 182 | 82 | 53.56 |

TABLE 7

| Treatment | Application Rate | Whole Plant Biomass (g) | Found % | Efficacy % | Calculated % |
|---|---|---|---|---|---|
| UTC | | 3.22 | 100 | | |
| SERENADE ® ASO 1% | 140.7 PPM $5.24 \times 10^8$ CFU/pot | 3.62 | 112 | 12 | |
| BEE 5% | $7.85 \times 10^8$ CFU/pot | 3.92 | 121 | 21 | |
| SERENADE ® ASO 1% + BEE 5% | $5.24 \times 10^8$ CFU/pot + $7.85 \times 10^8$ CFU/pot | 4.40 | 136 | 36 | 30.48 |

TABLE 8

| | Root Volume Average | % Found | % Efficacy | % Calculated |
|---|---|---|---|---|
| UTC | 5.259 | 100.0 | 0.0 | |
| SERENADE ® ASO 1% | 6.282 | 119.5 | 19.5 | |
| BEE 5% | 6.704 | 127.5 | 27.5 | |
| Ser 1% and BEE 5% | 8.209 | 156.1 | 56.1 | 41.6 |

The above results show a superadditive effect on plant yield when *Bacillus subtilis* QST713 and BEE are applied in combination.

Example 4: Plant Growth Promotion with *Bacillus firmus* Strain I-1582 and Recombinant *Bacillus thuringiensis* Cells Maize seeds will be grown in loamy sand in the greenhouse at 20° C. and 70% humidity for about 11 days. After about 11 days from the time of treatment the seedlings will be cut off above the soil and the fresh weight will be determined.

Recombinant *Bacillus thuringiensis* cells expressing an endoglucanase encoded by SEQ ID NO: 107 or a phospholipase C encoded by SEQ ID NO: 108 and prepared as described above will be applied at about 50 μg/kernel. *Bacillus firmus* strain I-1582 will also be applied at about 50 μg/kernel.

It is expected that the maize plants treated with the recombinant *Bacillus thuringiensis* in combination with the *Bacillus firmus* strain I-1582 will have % shoot weights that exceed the calculated value based on the % shoot weights from the maize plants treated with the two active ingredients alone, i.e., a synergistic effect will be observed.

```
                             SEQUENCE LISTING

Sequence total quantity: 109
SEQ ID NO: 1            moltype = AA  length = 41
FEATURE                 Location/Qualifiers
source                  1..41
                        mol_type = protein
                        organism = Bacillus anthracis
SEQUENCE: 1
MSNNNYSNGL NPDESLSASA FDPNLVGPTL PPIPPFTLPT G                  41

SEQ ID NO: 2            moltype = AA  length = 332
FEATURE                 Location/Qualifiers
source                  1..332
                        mol_type = protein
                        organism = Bacillus anthracis
SEQUENCE: 2
MSNNNYSNGL NPDESLSASA FDPNLVGPTL PPIPPFTLPT GPTGPFTTGP TGPTGPTGPT   60
GPTGPTGPTG PTGDTGTTGP TGPTGPTGPT GPTGPTGPTG PTGPTGFTPT GPTGPTGPTG  120
DTGTTGPTGP TGPTGPTGPT GDTGTTGPTG PTGPTGPTGP TGPTGPTFTG PTGPTGPTGA  180
TGLTGPTGPT GPSGLGLPAG LYAFNSGGIS LDLGINDPVP FNTVGSQFFT GTAISQLDAD  240
TFVISETGFY KITVIANTAT ASVLGGLTIQ VNGVPVPGTG SSLISLGAPF TIVIQAITQI  300
TTTPSLVEVI VTGLGLSLAL GTSASIIIEK VA                              332

SEQ ID NO: 3            moltype = AA  length = 33
FEATURE                 Location/Qualifiers
source                  1..33
                        mol_type = protein
                        organism = Bacillus anthracis
SEQUENCE: 3
MSEKYIILHG TALEPNLIGP TLPPIPPFTF PNG                            33

SEQ ID NO: 4            moltype = AA  length = 209
FEATURE                 Location/Qualifiers
source                  1..209
                        mol_type = protein
                        organism = Bacillus anthracis
SEQUENCE: 4
MSEKYIILHG TALEPNLIGP TLPPIPPFTF PNGPTGITGP TGATGFTGIG ITGPTGVTGP   60
TGIGITGPTG ATGLGILPVF GTITTDVGIG FSVIVNTNIN FTLPGPVSGT TLNPVDNSII  120
INTTGVYSVS FSIVFVIQAI SSSILNLTIN DSIQFAIESR IGGGPGVRAT SARTDLLSLN  180
QGDVLRVRIR EATGDIIYSN ASLVVSKVD                                 209

SEQ ID NO: 5            moltype = AA  length = 44
FEATURE                 Location/Qualifiers
source                  1..44
                        mol_type = protein
                        organism = Bacillus anthracis
SEQUENCE: 5
MVKVVEGNGG KSKIKSPLNS NFKILSDLVG PTFPPVPTGM TGIT                44

SEQ ID NO: 6            moltype = AA  length = 647
FEATURE                 Location/Qualifiers
source                  1..647
                        mol_type = protein
                        organism = Bacillus anthracis
SEQUENCE: 6
VVKVVEGNGG KSKIKSPLNS NFKILSDLVG PTFPPVPTGM TGITGSTGAT GNTGPTGETG   60
ATGSAGITGS TGPTGNTGGT GSTGPTGNTG ATGSTGVTGS TGVTGSTGVT GSTGVTGSTG  120
PTGETGGTGS TGVTGSTGAT GSTGVTGNTG PTGSTGATGN TGSIGETGGT GSMGPTGETG  180
VTGSTGGTGS TGVTGNTGPT GSTGVTGSTG VTGSTGPTGS TGVTGSTGPT GSTGVTGSTG  240
VTGNMGPTGS TGVTGNTGST GTTGATGETG PMGSTGATGT TGPTGETGET GETGGTGSTG  300
PTGNTGATGS TGVTGSTGVT GSTGVTGETG PTGSTGATGN TGPTGETGGT GSTGATGSTG  360
```

```
VTGNTGPTGS TGVTGNTGAT GETGPTGNTG ATGNTGPTGE TGVTGSTGPT GETGVTGSTG    420
PTGNTGATGE TGATGSTGVT GNTGSTGETG PTGSTGPTGS TGATGVTGNT GPTGSTGATG    480
ATGSTGPTGS TGTTGNTGVT GDTGPTGATG VSTTATYAFA NNTSGSVISV LLGGTNIPLP    540
NNQNIGPGIT VSGGNTVFTV ANAGNYYIAY TINLTAGLLV SSRITVNGSP LAGTINSPTV    600
ATGSFSATII ASLPAGAAVS LQLFGVVALA TLSTATPGAT LTIIRLS                  647

SEQ ID NO: 7           moltype = AA   length = 34
FEATURE                Location/Qualifiers
source                 1..34
                       mol_type = protein
                       organism = Bacillus anthracis
SEQUENCE: 7
MKQNDKLWLD KGIIGPENIG PTFPVLPPIH IPTG                                34

SEQ ID NO: 8           moltype = AA   length = 366
FEATURE                Location/Qualifiers
source                 1..366
                       mol_type = protein
                       organism = Bacillus anthracis
SEQUENCE: 8
MKQNDKLWLD KGIIGPENIG PTFPVLPPIH IPTGITGATG ATGITGATGP TGTTGATGAT     60
GITGVTGATG ITGVTGATGI TGVTGATGIT GVTGPTGITG ATGPTGITGA TGPAGITGVT    120
GPTGITGATG PTGTTGVTGP TGDTGLAGAT GPTGATGLAG ATGPTGDTGA TGPTGATGLA    180
GATGPTGATG LTGATGATGA TGGGAIIPFA SGTTPALLVN AVLANTGTLL GFGFSQPGIA    240
PGVGGTLTIL PGVVGDYAFV APRDGIITSL AGFFSATAAL APLTPVQIQM QIFIAPAASN    300
TFTPVAPPLL LTPALPAIAI GTTATGIQAY NVPVVAGDKI LVYVSLTGAS PIAAVAGFVS    360
AGLNIV                                                              366

SEQ ID NO: 9           moltype = AA   length = 30
FEATURE                Location/Qualifiers
source                 1..30
                       mol_type = protein
                       organism = Bacillus anthracis
SEQUENCE: 9
MDEFLSSAAL NPGSVGPTLP PMQPFQFRTG                                     30

SEQ ID NO: 10          moltype = AA   length = 77
FEATURE                Location/Qualifiers
source                 1..77
                       mol_type = protein
                       organism = Bacillus anthracis
SEQUENCE: 10
MDEFLSSAAL NPGSVGPTLP PMQPFQFRTG PTGSTGAKGA IGNTEPYWHT GPPGIVLLTY     60
DFKSLIISFA FRILPIS                                                   77

SEQ ID NO: 11          moltype = AA   length = 39
FEATURE                Location/Qualifiers
source                 1..39
                       mol_type = protein
                       organism = Bacillus weihenstephanensis
SEQUENCE: 11
MFDKNEIQKI NGILQANALN PNLIGPTLPP IPPFTLPTG                           39

SEQ ID NO: 12          moltype = AA   length = 299
FEATURE                Location/Qualifiers
source                 1..299
                       mol_type = protein
                       organism = Bacillus weihenstephanensis
SEQUENCE: 12
MFDKNEIQKI NGILQANALN PNLIGPTLPP IPPFTLPTGP TGVTGPTGVT GPTGVTGPTG     60
VTGPTGVTGP TGVTGPTGVT GPTGVTGPTG VTGPTGVTGP TGVTGPTGVT GPTGVTGPTG    120
VTGPTGETGP TGGTEGCLCD CCVLPMQSVL QQLIGETVIL GTIADTPNTP PLFFLFTITS    180
VNDFLVTVTD GTTTFVVNIS DVTGVGFLPP GPPITLLPPT DVGCECECRE RPIRQLLDAF    240
IGSTVSLLAS NGSIAADFSV EQTGLGIVLG TLPINPTTTV RFAISTCKIT AVNITPITM     299

SEQ ID NO: 13          moltype = AA   length = 39
FEATURE                Location/Qualifiers
source                 1..39
                       mol_type = protein
                       organism = Bacillus weihenstephanensis
SEQUENCE: 13
MFDKNEMKKT NEVLQANALD PNIIGPTLPP IPPFTLPTG                           39

SEQ ID NO: 14          moltype = AA   length = 289
FEATURE                Location/Qualifiers
source                 1..289
                       mol_type = protein
                       organism = Bacillus weihenstephanensis
SEQUENCE: 14
```

-continued

```
MFDKNEMKKT NEVLQANALD PNIIGPTLPP IPPFTLPTGP TGPTGPTGPT GPTGPTGPTG  60
PTGPTGPTGP TGPTGPTGLT GPTGPTGLTG PTGLTGPTGP TGLTGQTGST GPTGATEGCL  120
CDCCVFPMQE VLRQLVGQTV ILATIADAPN VAPRFFLFNI TSVNDFLVTV TDPVSNTTFV  180
VNISDVIGVG FSLTVPPLTL LPPADLGCEC DCRERPIREL LDTLIGSTVN LLVSNGSIAT  240
GFNVEQTALG IVIGTLPIPI NPPPPTLFRF AISTCKITAV DITPTPTAT              289

SEQ ID NO: 15          moltype = AA  length = 49
FEATURE                Location/Qualifiers
source                 1..49
                       mol_type = protein
                       organism = Bacillus cereus
SEQUENCE: 15
MSRKDKFNRS RMSRKDRFNS PKIKSEISIS PDLVGPTFPP IPSFTLPTG              49

SEQ ID NO: 16          moltype = AA  length = 189
FEATURE                Location/Qualifiers
source                 1..189
                       mol_type = protein
                       organism = Bacillus cereus
SEQUENCE: 16
MSRKDKFNRS RMSRKDRFNS PKIKSEISIS PDLVGPTFPP IPSFTLPTGI TGPTFNINFR  60
AEKNVAQSFT PPADIQVSYG NIIFNNGGGY SSVTNTFTAP INGIYLFSAS IGFNPTLGTT  120
STLRITIRKN LVSVASQTGT ITTGGTPQLE ITTIIDLLAS QTIDIQFSAA ESGTLTVGSS  180
NFFSGALLP                                                          189

SEQ ID NO: 17          moltype = AA  length = 33
FEATURE                Location/Qualifiers
source                 1..33
                       mol_type = protein
                       organism = Bacillus cereus
SEQUENCE: 17
MNEEYSILHG PALEPNLIGP TLPSIPPFTF PTG                               33

SEQ ID NO: 18          moltype = AA  length = 84
FEATURE                Location/Qualifiers
source                 1..84
                       mol_type = protein
                       organism = Bacillus cereus
SEQUENCE: 18
MNEEYSILHG PALEPNLIGP TLPSIPPFTF PTGPTGITGP TGATGFTGIG ITGPTGVTGP  60
TGIGITGPTG ATGPTGIGIT GPTG                                         84

SEQ ID NO: 19          moltype = AA  length = 39
FEATURE                Location/Qualifiers
source                 1..39
                       mol_type = protein
                       organism = Bacillus cereus
SEQUENCE: 19
MKNRDNNRKQ NSLSSNFRIP PELIGPTFPP VPTGFTGIG                         39

SEQ ID NO: 20          moltype = AA  length = 1056
FEATURE                Location/Qualifiers
source                 1..1056
                       mol_type = protein
                       organism = Bacillus cereus
SEQUENCE: 20
MKNRDNNRKQ NSLSSNFRIP PELIGPTFPP VPTGFTGIGI TGPTGPQGPT GPQGPRGLQG  60
PMGEMGPTGP QGVQGIQGSV GPIGATGPEG QQGPQGLRGP QGETGATGPG GVQGLQGPIG  120
PTGATGAQGI QGIQGLQGPI GATGPEGSQG IQGVQGLPGA TGPQGIQGAQ GIQGTPGPSG  180
NTGATGATGA TGQGITGPTG ITGPTGITGP SGGPPGPTGP TGATGPGGGP SGSTGATGAT  240
GNTGATGSTG VTGATGSTGP TGSTGAQGLQ GIQGIQGPIG PTGPEGSQGI QGIPGPTGVT  300
GEQGIQGVQG IQGATGATGD QGPQGIQGVI GPQGVTGATG DQGPQGIQGV PGPSGETGPQ  360
GVQGIQGPMG DIGPTGPEGP EGLQGPQGIQ GVPGPVGATG PEGPQGIQGI QGPVGATGPQ  420
GPQGIQGIQG VQGITGATGV QGATGIQGIQ GEIGATGPEG PQGVQGAQGA IGPTGPMGPQ  480
GVQGVQGIQG ATGAQGVQGP QGIQGIQGPT GATGDMGATG ATGEGTTGPT GVTGPTGVTG  540
PSGGPAGPTG PTGPSGPAGV TGPSGGPPGP TGATGATGVT GDTGATGSTG VTGATGETGA  600
TGVTGLQGPQ GIQGVQGEIG PTGPQGVQGP QGIQGVTGAT GDQGPQGIQG PQGDIGPTGP  660
QGIQGPQGSQ GIQGATGGTG AQGPQGIQGP QGDIGLTGSQ GPTGIQGIQG EIGPTGPEGP  720
EGLQGPQGIQ GIQGPVGATG PEGPQGIQGI QGVQGATGPQ GPQGIQGIQG VQGITGATGA  780
QGATGIQGIQ GEIGATGPEG PQGVQGIQGA IGPTGPMGAQ GVQGIQGIQG ATGAQGVQGP  840
QGIQGVQGPT GATGETGATG ATGEGTTGPT GVTGPTGVTG PSGGPAGPTG PTGPSGPAGV  900
TGPSGGPPGP TGATGATGVT GDTGATGSTG VTGATGATGA TGVTGLQGPQ GIQGVQGEIG  960
PTGPQGIQGP QGIQGVTGAT GAQGPQGIQG PQGDIGPTGS QGIQGPQGPQ GIQGATGATG  1020
AQGPQGIQGP QGEIGPTGPQ GPQGIQGPQG IQGPTG                            1056

SEQ ID NO: 21          moltype = AA  length = 39
FEATURE                Location/Qualifiers
source                 1..39
                       mol_type = protein
```

```
                         organism = Bacillus weihenstephanensis
SEQUENCE: 21
MSDKHQMKKI SEVLQAHALD PNLIGPPLPP ITPFTFPTG                        39

SEQ ID NO: 22            moltype = AA  length = 365
FEATURE                  Location/Qualifiers
source                   1..365
                         mol_type = protein
                         organism = Bacillus weihenstephanensis
SEQUENCE: 22
MSDKHQMKKI SEVLQAHALD PNLIGPPLPP ITPFTFPTGS TGPTGSTGST GPTGSTGNTG  60
PTGPTGPPVG TNLDTIYVTN DISNNVSAID GNTNTVLTTI PVGTNPVGVG VNSSTNLIYV  120
VNNGSDNISV INGSTNTVVA TIPVGTQPFG VGVNPSTNLI YVANRTSNNV SVIKGGTNTV  180
LTTIPVGTNP VGVGVNSSTN LIYVTNEIPN SVSVIKGGTN TVVATIPVGL FPFGVGVNSL  240
TNLIYVVNNS PHNVSVIDGN TNTVLTTISV GTSPVGVGVN LSTNLIYVAN EVPNNISVIN  300
GNTNTVLTTI PVGTTPFEVG VNSSTNLIYV SNLNSNNVSV INGSANTVIA TVPVGSVPRG  360
IGVKP                                                             365

SEQ ID NO: 23            moltype = AA  length = 30
FEATURE                  Location/Qualifiers
source                   1..30
                         mol_type = protein
                         organism = Bacillus weihenstephanensis
SEQUENCE: 23
MDEFLSFAAL NPGSIGPTLP PVPPFQFPTG                                  30

SEQ ID NO: 24            moltype = AA  length = 160
FEATURE                  Location/Qualifiers
source                   1..160
                         mol_type = protein
                         organism = Bacillus weihenstephanensis
SEQUENCE: 24
MDEFLSFAAL NPGSIGPTLP PVPPFQFPTG PTGSTGSTGP TGSTGSTGPT GFNLPAGPAS  60
ITLTSNETTA CVSTQGNNTL FFSGQVLVNG SPTPGVVVSF SFSNPSLAFM VPLAVITNAS  120
GNFTAVFLAA NGPGTVTVTA SLLDSPGTMA SVTITIVNCP                        160

SEQ ID NO: 25            moltype = AA  length = 30
FEATURE                  Location/Qualifiers
source                   1..30
                         mol_type = protein
                         organism = Bacillus weihenstephanensis
SEQUENCE: 25
MDEFLSSTAL NPCSIGPTLP PMQPFQFPTG                                  30

SEQ ID NO: 26            moltype = AA  length = 69
FEATURE                  Location/Qualifiers
source                   1..69
                         mol_type = protein
                         organism = Bacillus weihenstephanensis
SEQUENCE: 26
MDEFLSSTAL NPCSIGPTLP PMQPFQFPTG PTGSTGTTGP TGSIGPTGNT GLTGNTGPTG  60
ITGPTGDTG                                                         69

SEQ ID NO: 27            moltype = AA  length = 36
FEATURE                  Location/Qualifiers
source                   1..36
                         mol_type = protein
                         organism = Bacillus weihenstephanensis
SEQUENCE: 27
MKERDRQNSL NSNFRISPNL IGPTFPPVPT GFTGIG                            36

SEQ ID NO: 28            moltype = AA  length = 934
FEATURE                  Location/Qualifiers
source                   1..934
                         mol_type = protein
                         organism = Bacillus weihenstephanensis
SEQUENCE: 28
MKERDRQNSL NSNFRISPNL IGPTFPPVPT GFTGIGITGP TGPQGPTGPQ GPRGFQGPMG  60
EMGPTGPQGV QGIQGPAGQM GATGPEGQQG PQGLRGPQGE TGATGPQGVQ GLQGPIGPTG  120
ATGAQGIQGI QGLQGPIGAT GPEGPQGIQG VQGVPGATGS QGIQGAQGIQ GPQGPSGNTG  180
ATGVTGQGIS GPTGITGPTG ITGPSGGPPG PTGATGATGP GGGPSGSTGA TGATGNTGVT  240
GSAGVTGNTG STGSTGETGA QGLQGIQGVQ GPIGPTGPEG PQGIQGIPGP TGVTGEQGIQ  300
GVQGIQGITG ATGDQGPQGI QGAIGPQGIT GATGDQGPQG IQGVPGPTGD TGSQGVQGIQ  360
GPMGDIGPTG PEGPEGLQGP QGIQGVPGPA GATGPEGPQG IQGIQGPIGV TGPEGPQGIQ  420
GIQGIQGITG ATGAQGATGV QGVQGNIGAT GPEGPQGVQG TQGDIGPTGP MGPQGVQGIQ  480
GIQGPTGAQG VQGPQGIQGI QGPTGVTGDT GTTGATGEGT TGATGVTGPS GVTGPSGGPA  540
GPTGPTGPSG PTGLTGPSGG PPGPTGATGV TGGVGDTGAT GSTGVTGATG VTGATGATGL  600
QGPQGIQGVQ GDIGPTGPQG VQGPQGIQGI TGATGDQGPQ GIQGPQGIQG PTGPQGIQGG  660
QGPQGIQGAT GATGAQGPQG IQGIQGVQGP TGPQGPTGIQ GVQGEIGPTG PQGVQGLQGP  720
```

-continued

```
QGPTGDTGPT GPQGPQGIQG PTGATGATGS QGIQQGPTGAT GATGSQGIQG PTGATGATGA  780
TGATGATGAT GATGVTGVST TATYSFANNT SGSAISVLLG GTNIPLPNNQ NIGPGITVSG  840
GNTVFTVTNA GNYYIAYTIN ITAALLVSSR ITVNGSPLAG TINSPAVATG SFNATIISNL  900
AAGSAISLQL FGLLAVATLS TTTPGATLTI IRLS                              934

SEQ ID NO: 29           moltype = AA  length = 39
FEATURE                 Location/Qualifiers
source                  1..39
                        mol_type = protein
                        organism = Bacillus mycoides
SEQUENCE: 29
VFDKNEIQKI NGILQANALN PNLIGPTLPP IPPFTLPTG                         39

SEQ ID NO: 30           moltype = AA  length = 287
FEATURE                 Location/Qualifiers
source                  1..287
                        mol_type = protein
                        organism = Bacillus mycoides
SEQUENCE: 30
VFDKNEIQKI NGILQANALN PNLIGPTLPP IPPFTLPTGP TGGTGPTGVT GPTGVTGPTG  60
VTGPTGVTGP TGVTGPTGVT GPTGVTGPTG VTGPTGVTGP TGVTGPTGVT GPTGVTGPTG  120
GTEGCLCDCC VLPMQSVLQQ LIGETVILGT IADTPNTPPL FFLFTITSVN DFLVTVTDGT  180
TTFVVNISDV TGVGFLPPGP PITLLPPTDV GCECECRERP IRQLLDAFIG STVSLLASNG  240
SIAADFSVEQ TGLGIVLGTL PINPTTTVRF AISTCKITAV NITPITM                287

SEQ ID NO: 31           moltype = AA  length = 30
FEATURE                 Location/Qualifiers
source                  1..30
                        mol_type = protein
                        organism = Bacillus mycoides
SEQUENCE: 31
MDEFLYFAAL NPGSIGPTLP PVQPFQFPTG                                   30

SEQ ID NO: 32           moltype = AA  length = 190
FEATURE                 Location/Qualifiers
source                  1..190
                        mol_type = protein
                        organism = Bacillus mycoides
SEQUENCE: 32
MDEFLYFAAL NPGSIGPTLP PVQPFQFPTG PTGSTGATGS TGSTGSTGPT GSTGSTGSTG  60
STGPTGPTGP TGSTGPTGPT GFNLPAGPAS ITLTSNETTA CVSTQGNNTL FFSGQVLVNG  120
SPTPGVVVSF SFSNPSLAFM VPLAVITNAS GNFTAVFLAA NGPGTVTVTA SLLDSPGTMA  180
SVTITIVNCP                                                         190

SEQ ID NO: 33           moltype = AA  length = 21
FEATURE                 Location/Qualifiers
source                  1..21
                        mol_type = protein
                        organism = Bacillus mycoides
SEQUENCE: 33
MDSKNIGPTF PPLPSINFPT G                                            21

SEQ ID NO: 34           moltype = AA  length = 335
FEATURE                 Location/Qualifiers
source                  1..335
                        mol_type = protein
                        organism = Bacillus mycoides
SEQUENCE: 34
MDSKNIGPTF PPLPSINFPT GVTGETGATG ETGATGATGE TGATGETGET GATGATGATG  60
ATGETGATGA TGATGAAGAT GETGATGETG ATGETGATGE TGATGVTGET GATGETGAAG  120
ETGITGVTGP TGETGATGET GATGATGITG ATGITGVAGA TGETGAAGET GPTGATGAIG  180
AIGATGATGI TGVTGATGET GAAGATGITG VTGATGETGA AGATGITGAT GITGVAGATG  240
ITGPTGIPGT IPTTNLLYFT FSDGEKLIYT NADGIAQYGT TQILSPSEVS YINLFINGIL  300
QPQPFYEVTA GQLTLLDDEP PSQGSSIILQ FIIIN                             335

SEQ ID NO: 35           moltype = AA  length = 22
FEATURE                 Location/Qualifiers
source                  1..22
                        mol_type = protein
                        organism = Bacillus thuringiensis
SEQUENCE: 35
MIGPENIGPT FPILPPIYIP TG                                           22

SEQ ID NO: 36           moltype = AA  length = 234
FEATURE                 Location/Qualifiers
source                  1..234
                        mol_type = protein
                        organism = Bacillus thuringiensis
SEQUENCE: 36
```

```
MIGPENIGPT FPILPPIYIP TGETGPTGIT GATGETGPTG ITGPTGITGA TGETGSTGIT    60
GATGETGSTG ITGPIGITGA TGETGPIGIT GATGETGPTG ITGSTGITGL TGVTGLTGET   120
GPIGITGPTG ITGPTGVTGA TGPTGGIGPI TTTNLLYYTF ADGEKLIYTD TDGIPQYGTT   180
NILSPSEVSY INLFVNGILQ PQPLYEVSTG KLTLLDTQPP SQGSSIILQF IIIN         234

SEQ ID NO: 37              moltype = DNA  length = 23
FEATURE                    Location/Qualifiers
misc_feature               1..23
                           note = Primer
source                     1..23
                           mol_type = other DNA
                           organism = synthetic construct
SEQUENCE: 37
ggatccatgg ctgaacacaa tcc                                            23

SEQ ID NO: 38              moltype = DNA  length = 24
FEATURE                    Location/Qualifiers
misc_feature               1..24
                           note = Primer
source                     1..24
                           mol_type = other DNA
                           organism = synthetic construct
SEQUENCE: 38
ggatccttaa ttcgtattct ggcc                                           24

SEQ ID NO: 39              moltype = DNA  length = 21
FEATURE                    Location/Qualifiers
misc_feature               1..21
                           note = Primer
source                     1..21
                           mol_type = other DNA
                           organism = synthetic construct
SEQUENCE: 39
ggatccatga acggtcaat c                                               21

SEQ ID NO: 40              moltype = DNA  length = 24
FEATURE                    Location/Qualifiers
misc_feature               1..24
                           note = Primer
source                     1..24
                           mol_type = other DNA
                           organism = synthetic construct
SEQUENCE: 40
ggatccttac taatttggtt ctgt                                           24

SEQ ID NO: 41              moltype = DNA  length = 21
FEATURE                    Location/Qualifiers
misc_feature               1..21
                           note = Primer
source                     1..21
                           mol_type = other DNA
                           organism = synthetic construct
SEQUENCE: 41
ggatccatgc taccaaaagc c                                              21

SEQ ID NO: 42              moltype = DNA  length = 24
FEATURE                    Location/Qualifiers
misc_feature               1..24
                           note = Primer
source                     1..24
                           mol_type = other DNA
                           organism = synthetic construct
SEQUENCE: 42
ggatccttag tccgcaggcg tagc                                           24

SEQ ID NO: 43              moltype = AA  length = 35
FEATURE                    Location/Qualifiers
source                     1..35
                           mol_type = protein
                           organism = Bacillus cereus
SEQUENCE: 43
MSNNNIPSPF FFNNFNPELI GPTFPPIPPL TLPTG                               35

SEQ ID NO: 44              moltype = AA  length = 222
FEATURE                    Location/Qualifiers
source                     1..222
                           mol_type = protein
                           organism = Bacillus cereus
SEQUENCE: 44
```

-continued

```
MSNNNIPSPF FFNNFNPELI GPTFPPIPPL TLPTGPTGST GATGATGPTG ATGPTGATGP  60
TGATGATGST GATGPTGATG TFSSANASIV TPAPQTVNNL APIQFTAPVL ISKNVTFNGI  120
DTFTIQIPGN YFFIGAVMTS NNQAGPVAVG VGFNGIPVPS LDGANYGTPT GQEVVCFGFS  180
GQIPAGTTIN LYNISDKTIS IGGATAAGSS IVAARLSFFR IS                    222

SEQ ID NO: 45           moltype = AA  length = 41
FEATURE                 Location/Qualifiers
source                  1..41
                        mol_type = protein
                        organism = Bacillus cereus
SEQUENCE: 45
MFSEKKRKDL IPDNFLSAPA LDPNLIGPTF PPIPSFTLPT G                     41

SEQ ID NO: 46           moltype = AA  length = 293
FEATURE                 Location/Qualifiers
source                  1..293
                        mol_type = protein
                        organism = Bacillus cereus
SEQUENCE: 46
MFSEKKRKDL IPDNFLSAPA LDPNLIGPTF PPIPSFTLPT GSTGPTGPTG DTGPTGPTAT  60
ICIRTDPDNG CSVAEGSGTV ASGFASHAEA CNTQAIGDCS HAEGQFATAS GTASHAEGFQ  120
TTASGFASHT EGSGTTADAN FSHTEGINTI VDVLHPGSHI MGKNGTTRSS FSWHLANGLA  180
VGPSLNSAVI EGVTGNLYLD GVVISPNAAD YAEMFETIDG NLIDVGYFVT LYGEKIRKAN  240
ANDDYILGVV SATPAMIADA SDLRWHNLFV RDEWGRTQYH EVVVPEKKMA MEE         293

SEQ ID NO: 47           moltype = AA  length = 49
FEATURE                 Location/Qualifiers
source                  1..49
                        mol_type = protein
                        organism = Bacillus cereus
SEQUENCE: 47
MTRKDKFNRS RISRRDRFNS PKIKSEILIS PDLVGPTFPP IPSFTLPTG             49

SEQ ID NO: 48           moltype = AA  length = 83
FEATURE                 Location/Qualifiers
source                  1..83
                        mol_type = protein
                        organism = Bacillus cereus
SEQUENCE: 48
MTRKDKFNRS RISRRDRFNS PKIKSEILIS PDLVGPTFPP IPSFTLPTGV TGPTGNTGPT  60
GITGPTGDTG PTGDTGPTGI TGP                                         83

SEQ ID NO: 49           moltype = AA  length = 38
FEATURE                 Location/Qualifiers
source                  1..38
                        mol_type = protein
                        organism = Bacillus cereus
SEQUENCE: 49
MSRKDRFNSP KIKSEISISP DLVGPTFPPI PSFTLPTG                         38

SEQ ID NO: 50           moltype = AA  length = 163
FEATURE                 Location/Qualifiers
source                  1..163
                        mol_type = protein
                        organism = Bacillus cereus
SEQUENCE: 50
MSRKDRFNSP KIKSEISISP DLVGPTFPPI PSFTLPTGIT GPTGNTGPTG DTGPTGPTFN  60
INFRAEKNGA QSFTPPADIQ VSYGNIIFNN GGGYSSVTNT FTAPINGIYL FSANIGFNPT  120
LGTTSTLRIT IRKNLVSVAS QTIDIQFSAA ESGTLTVGSS NFF                   163

SEQ ID NO: 51           moltype = AA  length = 39
FEATURE                 Location/Qualifiers
source                  1..39
                        mol_type = protein
                        organism = Bacillus cereus
SEQUENCE: 51
MKERDNKGKQ HSLNSNFRIP PELIGPTFPP VPTGFTGIG                        39

SEQ ID NO: 52           moltype = AA  length = 323
FEATURE                 Location/Qualifiers
source                  1..323
                        mol_type = protein
                        organism = Bacillus cereus
SEQUENCE: 52
MKERDNKGKQ HSLNSNFRIP PELIGPTFPP VPTGFTGIGI TGPTGPQGPT GPQGPRGFQG  60
PMGEMGPTGP QGVQGIQGPA GQMGATGPEG QQGPEGLRGP VGATGATGLQ GVQGIQGPIG  120
STGATGAQGI QGIQGLQGPI GATGPEGPQG IQGVQGLPGA TGPQGVQGVQ GVIGPQGPSG  180
STGGTGATGQ GVTGPTGITG STGVTGPSGG PPGPTGPTGA TGPGGGPSGS TGVTGSTGNT  240
GATGSPGVTG ATGPTGSTGA TGIQGSQGIQ GIQGIQGPLG PTGPEGPQGI QGIPGPTGIT  300
```

-continued

```
GEQGIQGVQG IQGITGATGD QGT                                          323

SEQ ID NO: 53          moltype = AA  length = 39
FEATURE                Location/Qualifiers
source                 1..39
                       mol_type = protein
                       organism = Bacillus cereus
SEQUENCE: 53
MRERDNKRQQ HSLNPNFRIS PELIGPTFPP VPTGFTGIG                         39

SEQ ID NO: 54          moltype = AA  length = 436
FEATURE                Location/Qualifiers
source                 1..436
                       mol_type = protein
                       organism = Bacillus cereus
SEQUENCE: 54
MRERDNKRQQ HSLNPNFRIS PELIGPTFPP VPTGFTGIGI TGPTGPQGPT GPQGPRGFQG  60
PMGEMGPTGP QGVQGIQGPV GPIGATGPEG QQGPQGLRGP QGETGATGPG GVQGLQGPIG  120
PTGATGAQGV QGIQGLQGPI GATGPEGPQG IQGVQGLPGA TGSQGIQGVQ GIQGPQGPSG  180
NTGATGATGQ GITGPTGITG PTGITGPSGG PPGPTGPTGA TGPGGGPSGS TGATGATGNT  240
GATGNTGITG ATGSTGPTGS TGAQGLQGIQ GIQGPIGPTG PEGPQGIQGI PGPTGVTGEQ  300
GIQGVQGIQG ITGATGDQGP QGIQGVIGAQ GVTGATGDQG PQGIQGVPGP SGATGPQGVQ  360
GIQGPMGDIG PTGPEGPEGL QGPQGIQGVP GPVGATGPEG PQGIQGIQGV QGATGPQGPQ  420
GIQGIQGVQG ITGATG                                                  436

SEQ ID NO: 55          moltype = AA  length = 36
FEATURE                Location/Qualifiers
source                 1..36
                       mol_type = protein
                       organism = Bacillus thuringiensis
SEQUENCE: 55
MKNRDNKGKQ QSNFRIPPEL IGPTFPPVPT GFTGIG                            36

SEQ ID NO: 56          moltype = AA  length = 470
FEATURE                Location/Qualifiers
source                 1..470
                       mol_type = protein
                       organism = Bacillus thuringiensis
SEQUENCE: 56
MKNRDNKGKQ QSNFRIPPEL IGPTFPPVPT GFTGIGITGP TGPQGPTGPQ GPRGFQGPMG  60
EMGPTGPQGV QGIQGPVGPI GATGPEGQQG AQGLRGPQGE TGATGPQGVQ GLQGPIGPTG  120
ATGAQGIQGI QGLQGPIGAT GPEGPQGIQG VQGLPGATGP QGIQGAQGIQ GTQGPSGNTG  180
ATGATGQGLT GPTGITGPTG ITGPSGGPPG PTGPTGATGP GGGPSGSTGA TGATGDTGAT  240
GSTGVTGATG AQGPQGVQGI QGPTGATGAT GATGPQGIQG PQGIQGPTGA TGATGSQGPT  300
GNTGPTGSQG IQGPTGPTGA GATGATGATG ATGVSTTATY AFANNTSGSI ISVLLGGTNI  360
PLPNNQNIGP GITVSGGNTV FTVANAGNYY IAYTINLTAG LLVSSRITVN GSPLAGTINS  420
PAVAAGSFSA TIIANLPAGA AVSLQLFGVI ALATLSTATP GATLTIIRLS             470

SEQ ID NO: 57          moltype = AA  length = 136
FEATURE                Location/Qualifiers
source                 1..136
                       mol_type = protein
                       organism = Bacillus mycoides
SEQUENCE: 57
MKFSKKSTVD SSIVGKRVVS KVNILRFYDA RSCQDKDVDG FVDVGELFTI FRKLNMEGSV  60
QFKAHNSIGK TYYITINEVY VFVTVLLQYS TLIGGSYVFD KNEIQKINGI LQANALNPNL  120
IGPTLPPIPP FTLPTG                                                  136

SEQ ID NO: 58          moltype = AA  length = 384
FEATURE                Location/Qualifiers
source                 1..384
                       mol_type = protein
                       organism = Bacillus mycoides
SEQUENCE: 58
MKFSKKSTVD SSIVGKRVVS KVNILRFYDA RSCQDKDVDG FVDVGELFTI FRKLNMEGSV  60
QFKAHNSIGK TYYITINEVY VFVTVLLQYS TLIGGSYVFD KNEIQKINGI LQANALNPNL  120
IGPTLPPIPP FTLPTGPTGG TGPTGVTGPT GVTGPTGVTG PTGVTGPTGV TGPTGVTGPT  180
GVTGPTGVTG PTGVTGPTGV TGPTGVTGPT GVTGPTGGTE GCLCDCCVLP MQSVLQQLIG  240
ETVILGTIAD TPNTPPLFFL FTITSVNDFL VTVTDGTTTF VVNISDVTGV GFLPPGPPIT  300
LLPPTDVGCE CECRERPIRQ LLDAFIGSTV SLLASNGSIA ADFSVEQTGL GIVLGTLPIN  360
PTTTVRFAIS TCKITAVNIT PITM                                         384

SEQ ID NO: 59          moltype = AA  length = 196
FEATURE                Location/Qualifiers
source                 1..196
                       mol_type = protein
                       organism = Bacillus anthracis
SEQUENCE: 59
MSNNNYSNGL NPDESLSASA FDPNLVGPTL PPIPPFTLPT GPTGPFTTGP TGPTGPTGPT  60
```

```
GPTGPTGPTG PTGDTGTTGP TGPTGPTGPT GPTGPTGPTG PTGPTGFTPT GPTGPTGPTG    120
DTGTTGPTGP TGPTGPTGPT GDTGTTGPTG PTGPTGPTGP TGPTGPTFTG PTGPTGPTGA    180
TGLTGPTGPT GPSGLG                                                    196

SEQ ID NO: 60           moltype = AA   length = 17
FEATURE                 Location/Qualifiers
source                  1..17
                        mol_type = protein
                        organism = Bacillus anthracis
SEQUENCE: 60
MAFDPNLVGP TLPPIPP                                                   17

SEQ ID NO: 61           moltype = AA   length = 17
FEATURE                 Location/Qualifiers
source                  1..17
                        mol_type = protein
                        organism = Bacillus anthracis
SEQUENCE: 61
MALEPNLIGP TLPPIPP                                                   17

SEQ ID NO: 62           moltype = AA   length = 17
FEATURE                 Location/Qualifiers
source                  1..17
                        mol_type = protein
                        organism = Bacillus weihenstephanensis
SEQUENCE: 62
MALNPNLIGP TLPPIPP                                                   17

SEQ ID NO: 63           moltype = AA   length = 17
FEATURE                 Location/Qualifiers
source                  1..17
                        mol_type = protein
                        organism = Bacillus weihenstephanensis
SEQUENCE: 63
MALDPNIIGP TLPPIPP                                                   17

SEQ ID NO: 64           moltype = AA   length = 17
FEATURE                 Location/Qualifiers
source                  1..17
                        mol_type = protein
                        organism = Bacillus cereus
SEQUENCE: 64
MALEPNLIGP TLPSIPP                                                   17

SEQ ID NO: 65           moltype = AA   length = 17
FEATURE                 Location/Qualifiers
source                  1..17
                        mol_type = protein
                        organism = Bacillus weihenstephanensis
SEQUENCE: 65
MALDPNLIGP PLPPITP                                                   17

SEQ ID NO: 66           moltype = AA   length = 17
FEATURE                 Location/Qualifiers
source                  1..17
                        mol_type = protein
                        organism = Bacillus weihenstephanensis
SEQUENCE: 66
MALNPGSIGP TLPPVPP                                                   17

SEQ ID NO: 67           moltype = AA   length = 17
FEATURE                 Location/Qualifiers
source                  1..17
                        mol_type = protein
                        organism = Bacillus weihenstephanensis
SEQUENCE: 67
MALNPCSIGP TLPPMQP                                                   17

SEQ ID NO: 68           moltype = AA   length = 17
FEATURE                 Location/Qualifiers
source                  1..17
                        mol_type = protein
                        organism = Bacillus mycoides
SEQUENCE: 68
MALNPGSIGP TLPPVQP                                                   17

SEQ ID NO: 69           moltype = AA   length = 17
FEATURE                 Location/Qualifiers
source                  1..17
```

```
                                mol_type = protein
                                organism = Bacillus anthracis
SEQUENCE: 69
MALNPGSVGP TLPPMQP                                                            17

SEQ ID NO: 70          moltype = AA    length = 17
FEATURE                Location/Qualifiers
source                 1..17
                       mol_type = protein
                       organism = Bacillus cereus
SEQUENCE: 70
MALDPNLIGP TFPPIPS                                                            17

SEQ ID NO: 71          moltype = AA    length = 799
FEATURE                Location/Qualifiers
source                 1..799
                       mol_type = protein
                       organism = Bacillus mycoides
SEQUENCE: 71
MKRKTPFKVF SSLAITTMLG CTFALGTSVA YAETTSQSKG SISTTPIDNN LIQEERLAEA             60
LKERGTIDQS ASKEETQKAV EQYIEKKKGD QPNKEILPDD PAKEASDFVK KVKEKKMEEK            120
EKVKKSVENA SSEQTPSQNK KQLNGKVPTS PAKQAPYNGA VRTDKVLVLL VEFSDYKHNN            180
IEQSPGYMYA NDFSREHYQK MLFGNEPFTL FDGSKVKTFK QYYEEQSGGS YTTDGYVTEW            240
LTVPGKAADY GADGKTGHDN KGPKGARDLV KEALKAAAEK GLDLSQFDQF DRYDTNGDGN            300
QNEPDGVIDH LMVIHAGVGQ EAGGGKLGDD AIWSHRSKLA QDPVAIEGTK SKVSYWDGKV            360
AAHDYTIEPE DGAVGVFAHE FGHDLGLPDE YDTNYTGAGS PVEAWSLMSG GSWTGRIAGT            420
EPTSFSPQNK DFLQKNMDGN WAKIVEVDYD KIKRGVGFPT YIDQSVTKSN RPGLVRVNLP            480
EKSVETIKTG FGKHAYYSTR GDDMHTTLET PLFDLTKAAN AKFDYKANYE LEAECDFIEV            540
HAVTEDGTKT LIDKLGDKVV KGDQDTTEGK WIDKSYDLSQ FKGKKVKLQF DYITDPALTY            600
KGFAMDNVNV TVDGKVVFSD DAEGQAKMKL NGFVVSDGTE KKPHYYYLEW RNYAGSDEGL            660
KVGRGPVYNT GLVVWYADDS FKDNWVGRHP GEGFLGVVDS HPEAVVGNLN GKPVYGNTGL            720
QIADAAFSLD QTPAWNVNSF TRGQFNYPGL PGVATFDDSK VYSNTQIPDA GRKVPQLGLK            780
FQVVGQADDK SAGAIWIRR                                                         799

SEQ ID NO: 72          moltype = AA    length = 152
FEATURE                Location/Qualifiers
source                 1..152
                       mol_type = protein
                       organism = Bacillus anthracis
SEQUENCE: 72
MSCNENKHHG SSHCVVDVVK FINELQDCST TTCGSGCEIP FLGAHNTASV ANTRPFILYT             60
KAGAPFEAFA PSANLTSCRS PIFRVESVDD DSCAVLRVLS VVLGDSSPVP PTDDPICTFL            120
AVPNARLVST STCITVDLSC FCAIQCLRDV TI                                          152

SEQ ID NO: 73          moltype = AA    length = 167
FEATURE                Location/Qualifiers
source                 1..167
                       mol_type = protein
                       organism = Bacillus anthracis
SEQUENCE: 73
MFSSDCEFTK IDCEAKPAST LPAFGFAFNA SAPQFASLFT PLLLPSVSPN PNITVPVIND             60
TVSVGDGIRI LRAGIYQISY TLTISLDNSP VAPEAGRFFL SLGTPANIIP GSGTAVRSNV            120
IGTGEVDVSS GVILINLNPG DLIRIVPVEL IGTVDIRAAA LTVAQIS                          167

SEQ ID NO: 74          moltype = AA    length = 156
FEATURE                Location/Qualifiers
source                 1..156
                       mol_type = protein
                       organism = Bacillus anthracis
SEQUENCE: 74
MSCNCNEDHH HHDCDFNCVS NVVRFIHELQ ECATTTCGSG CEVPFLGAHN SASVANTRPF             60
ILYTKAGAPF EAFAPSANLT SCRSPIFRVE SIDDDDCAVL RVLSVVLGDT SPVPPTDDPI            120
CTFLAVPNAR LISTNTCLTV DLSCFCAIQC LRDVTI                                      156

SEQ ID NO: 75          moltype = AA    length = 182
FEATURE                Location/Qualifiers
source                 1..182
                       mol_type = protein
                       organism = Bacillus anthracis
SEQUENCE: 75
MEVGGTSVKN KNKSSTVGKP LLYIAQVSLE LAAPKTKRII LTNFENEDRK EESNRNENVV             60
SSAVEEVIEQ EEQQQEQEQE QEEQVEEKTE EEEQVQEQQE PVRTVPYNKS FKDMNNEEKI            120
HFLLNRPHYI PKVRCRIKTA TISYVGSIIS YRNGIVAIMP PNSMRDIRLS IEEIKSIDMA            180
GF                                                                          182

SEQ ID NO: 76          moltype = AA    length = 174
FEATURE                Location/Qualifiers
source                 1..174
                       mol_type = protein
```

```
                              organism = Bacillus anthracis
SEQUENCE: 76
MKERSENMRS SSRKLTNFNC RAQAPSTLPA LGFAFNATSP QFATLFTPLL LPSTGPNPNI    60
TVPVINDTIS TGTGIRIQVA GIYQISYTLT ISLDNVPVTP EAARFFLTLN SSTNIIAGSG   120
TAVRSNIIGT GEVDVSSGVI LINLNPGDLI QIVPVEVIGT VDIRSAALTV AQIR         174

SEQ ID NO: 77           moltype = AA  length = 796
FEATURE                 Location/Qualifiers
source                  1..796
                        mol_type = protein
                        organism = Bacillus thuringiensis
SEQUENCE: 77
MSKKPFKVLS SIALTAVLGL SFGAGTQSAY AETPVNKTAT SPVDDHLIPE ERLADALKKR    60
GVIDSKASET ETKKAVEKYV ENKKGENPGK EAANGDQLTK DASDFLKKVK DAKADTKEKL   120
NQPATGTPAA TGPVKGGLNG KVPTSPAKQK DYNGEVRKDK VLVLLVEYAD FKHNNIDKEP   180
GYMYSNDFNK EHYEKMLFGN EPFTLDDGSK IETFKQYYEE QSGGSYTVDG TVTKWLTVPG   240
KAADYGADAP GGGHDNKGPK GPRDLVKDAL KAAVDSGIDL SEFDQFDQYD VNGDGNKNQP   300
DGLIDHLMII HAGVGQEAGG GKLGDDAIWS HRWTVGPKPF PIEGTQAKVP YWGGKMAAFD   360
YTIEPEDGAV GVFAHEYGHD LGLPDEYDTQ YSGQGEPIEA WSIMSGGSWA GKIAGTTPTS   420
FSPQNKEFFQ KTIGGNWANI VEVDYEKLNK GIGLATYLDQ SVTKSARPGM IRVNLPDKDV   480
KTIEPAFGKQ YYYSTKGDDL HTKMETPLFD LTNATSAKFD FKSLYEIEAG YDFLEVHAVT   540
EDGKQTLIER LGEKANSGNA DSTNGKWIDK SYDLSQFKGK KVKLTFDYIT DGGLALNGFA   600
LDNASLTVDG KVVFSDDAEG TPQLKLDGFV VSNGTEKKKH NYYVEWRNYA GADNALKFAR   660
GPVFNTGMVV WYADSAYTDN WVGVHPGHGF LGVVDSHPEA IVGTLNGKPT VKSSTRFQIA   720
DAAFSFDKTP AWKVVSPTRG TFTYDGLAGV PKFDDSKTYI NQQIPDAGRI LPKLGLKFEV   780
VGQADDNSAG AVRLYR                                                  796

SEQ ID NO: 78           moltype = AA  length = 430
FEATURE                 Location/Qualifiers
source                  1..430
                        mol_type = protein
                        organism = Bacillus cereus
SEQUENCE: 78
MKHNDCFDHN NCNPIVFSAD CCKNPQSVPI TREQLSQLIT LLNSLVSAIS AFFANPSNAN    60
RLVLLDLFNQ FLIFLNSLLP SPEVNFLKQL TQSIIVLLQS PAPNLGQLST LLQQFYSALA   120
QFFFALDLIP ISCNSNVDSA TLQLLFNLLI QLINATPGAT GPTGPTGPTG PTGPAGTGAG   180
PTGATGATGA TGPTGATGPA GTGGATGATG ATGVTGATGA TGATGPTGPT GATGPTGATG   240
ATGATGPTGA TGPTGATGLT GATGAAGGGA IIPFASGTTP SALVNALVAN TGTLLGFGFS   300
QPGVALTGGT SITLALGVGD YAFVAPRAGT ITSLAGFFSA TAALAPISPV QVQIQILTAP   360
AASNTFTVQG APLLLTPAFA AIAIGSTASG IIAEAIPVAA GDKILLYVSL TAASPIAAVA   420
GFVSAGINIV                                                         430

SEQ ID NO: 79           moltype = AA  length = 437
FEATURE                 Location/Qualifiers
source                  1..437
                        mol_type = protein
                        organism = Bacillus cereus
SEQUENCE: 79
MKHNDCFGHN NCNNPIVFTP DCCNNPQTVP ITSEQLGRLI TLLNSLIAAI AAFFANPSDA    60
NRLALLNLFT QLLNLLNELA PSPEGNFLKQ LIQSIINLLQ SPNPNLGQLL SLLQQFYSAL   120
APFFFSLILD PASLQLLLNL LAQLIGVTPG GGATGPTGPT PGGGATGPT GPTGPGGGAT   180
GPTGATGPTG DTGLAGATGA TGPTGDTGVA GPAGPTGPTG DTGLAGATGP TGPTGDTGLA   240
GATGPTGATG LAGATGPTGA TGLTGATGAT GAAGGGAIIP FASGTTPAAL VNALIANTGT   300
LLGFGFSQPG IGLAGGTSIT LALGVGDYAF VAPRDGVITS LAGFFSATAA LSPLSPVQVQ   360
IQILTAPAAS NTFTVQGAPL LLTPAFAAIA IGSTASGIIP EAIPVVAGDK ILLYVSLTAA   420
SPIAAVAGFV SAGINIV                                                 437

SEQ ID NO: 80           moltype = AA  length = 119
FEATURE                 Location/Qualifiers
source                  1..119
                        mol_type = protein
                        organism = Bacillus anthracis
SEQUENCE: 80
MLFTSWLLFF IFALAAFRLT RLIVYDKITG FLRRPFIDEL EITEPDGSVS TFTKVKGKGL    60
RKWIGELLSC YWCTGVWVSA FLLVLYNWIP IVAEPLLALL AIAGAAAIIE TITGYFMGE    119

SEQ ID NO: 81           moltype = AA  length = 61
FEATURE                 Location/Qualifiers
source                  1..61
                        mol_type = protein
                        organism = Bacillus anthracis
SEQUENCE: 81
MFAVSNNPRQ NSYDLQQWYH MQQQHQAQQQ AYQEQLQQQG FVKKKGCNCG KKKSTIKHYE    60
E                                                                   61

SEQ ID NO: 82           moltype = AA  length = 481
FEATURE                 Location/Qualifiers
source                  1..481
                        mol_type = protein
```

```
                        organism = Bacillus anthracis
SEQUENCE: 82
MSRYDDSQNK FSKPCFPSSA GRIPNTPSIP VTKAQLRTFR AIIIDLTKII PKLFANPSPQ    60
NIEDLIDTLN LLSKFICSLD AASSLKAQGL AIIKNLITIL KNPTFVASAV FIELQNLINY   120
LLSITKLFRI DPCTLQELLK LIAALQTALV NSASFIQGPT GPTGPTGPTG PAGATGATGP   180
QGVQGPAGAT GATGPQGVQG PAGATGATGP QGAQGPAGAT GATGPQGAQG PAGATGATGP   240
QGIQGPAGAT GATGPQGVQG PTGATGIGVT GPTGPSGGPA GATGPQGPQG NTGATGPQGI   300
QGPAGATGAT GPQGAQGPAG ATGATGPQGV QGPTGATGIG VTGPTGPSGP SFPVATIVVT   360
NNIQQTVLQF NNFIFNTAIN VNNIIFNGTD TVTVINAGIY VISVSISTTA PGCAPLGVGI   420
SINGAVATDN FSSNLIGDSL SFTTIETLTA GANISVQSTL NEITIPATGN TNIRLTVFRI   480
A                                                                  481

SEQ ID NO: 83           moltype = AA  length = 275
FEATURE                 Location/Qualifiers
source                  1..275
                        mol_type = protein
                        organism = Bacillus thuringiensis
SEQUENCE: 83
MKMKRGITTL LSVAVLSTSL VACSGITEKT VAKEEKVKLT DQQLMADLWY QTAGEMKALY    60
YQGYNIGQLK LDAVLAKGTE KKPAIVLDLD ETVLDNSPHQ AMSVKTGKGY PYKWDDWINK   120
AEAEAEALPGAI DFLKYTESKG VDIYYISNRK TNQLDATIKN LERVGAPQAT KEHILLQDPK  180
EKGKEKRREL VSQTHDIVLF FGDNLSDFTG FDGKSVKDRN QAVADSKAQF GEKFIIFPNP   240
MYGDWEGALY DYDFKKSDAE KDKIRRDNLK SFDTK                              275

SEQ ID NO: 84           moltype = AA  length = 795
FEATURE                 Location/Qualifiers
source                  1..795
                        mol_type = protein
                        organism = Bacillus thuringiensis
SEQUENCE: 84
MKKKKKLKPL AVLTTAAVLS STFAFGGHAA YAETPTSSLP IDEHLIPEER LAEALKQRGV    60
IDQSASQAET SKAVEKYVEK KKGENPGKEI LTGDSLTQEA SDFMKKVKDA KMRENEQAQQ   120
PEVGPVAGQG AALNPGKLNG KVPTTSAKQE EYNGAVRKDK VLVLLVEFSD FKHNNIDQEP   180
GYMYSKDFNR EHYQKMLFGD EPFTLFDGSK INTFKQYVEE QSGGSYTVDG TVTEWLTVPG   240
KASDYGADAG TGHDNKGPLG PKDLVKEALK AAVAKGINLA DFDQYDQYDQ NGNGNKNEPD   300
GIIDHLMVVH AGVGQEAGGG KLKDDAIWSH RSKLGSKPYA IDGTKSSVSN WGGKMAAYDY   360
TIEPEDGAVG VFAHEYGHDL GLPDEYDTKY SGQGEPVESW SIMSGGSWAG KIAGTEPTSF   420
SPQNKEFFQK NMKGNWANIL EVDYDKLSKG IGVATYVDQS TTKSKRPGIV RVNLPDKDIK   480
NIESAFGKKF YYSTKGNDIH TTLETPVFDL TNAKDAKFDY KAFYELEAKY DFLDVYAIAE   540
DGTKTRIDRM GEKDIKGGAD TTDGKWVDKS YDLSQFKGKK VKLQFEYLTD IAVAYKGFAL   600
DNAALTVDGK VVFSDDAEGQ PAMTLKGFTV SNGFEQKKHN YYVEWRNYAG SDTALQYARG   660
PVFNTGMVVW YADQSTDNW VGVHPGEGFL GVVDSHPEAI VGTLNGQPTV KSSTRYQIAD   720
AAFSFDQTPA WKVNSPTRGI FDYKGLPGVA KFDDSKQYIN SVIPDAGRKL PKLGLKFEVV   780
GQAEDKSAGA VWLHR                                                   795

SEQ ID NO: 85           moltype = DNA  length = 169
FEATURE                 Location/Qualifiers
source                  1..169
                        mol_type = other DNA
                        organism = Bacillus anthracis
SEQUENCE: 85
taatcaccct cttccaaatc aatcatatgt tatacatata ctaaactttc cattttttta    60
aattgttcaa gtagtttaag atttcttttc ataattcaa atgtccgtgt catttttcttt   120
cggttttgca tctactatat aatgaacgct ttatggaggt gaattatg                169

SEQ ID NO: 86           moltype = DNA  length = 303
FEATURE                 Location/Qualifiers
source                  1..303
                        mol_type = other DNA
                        organism = Bacillus anthracis
SEQUENCE: 86
atttatttca ttcaattttt cctatttagt acctaccgca ctcacaaaaa gcacctctca    60
ttaatttata ttatagtcat tgaaatctaa tttaatgaaa tcatcatact atatgtttta   120
taagaagtaa aggtaccata cttaattaat acatatcat acacttcaat atcacagcat   180
gcagttgaat tatatccaac tttcatttca aattaaaataa gtgcctccgc tattgtgaat   240
gtcattact ctccctacta catttaataa ttatgacaag caatcatagg aggttactac    300
atg                                                                 303

SEQ ID NO: 87           moltype = DNA  length = 173
FEATURE                 Location/Qualifiers
source                  1..173
                        mol_type = other DNA
                        organism = Bacillus anthracis
SEQUENCE: 87
aattacataa caagaactac attagggagc aagcagtcta gcgaaagcta actgcttttt    60
tattaaataa ctatttttatt aaatttcata tatacaatcg cttgtccatt tcatttggct   120
ctacccacgc atttactatt agtaaatatga attttttcaga ggtggatttt att         173

SEQ ID NO: 88           moltype = DNA  length = 124
```

```
FEATURE              Location/Qualifiers
source               1..124
                     mol_type = other DNA
                     organism = Bacillus weihenstephanensis
SEQUENCE: 88
ctatgattta agatacacaa tagcaaaaga gaaacatatt atataacgat aaatgaaact    60
tatgtatatg tatggtaact gtatatatta ctacaataca gtatactcat aggaggtagg   120
tatg                                                                124

SEQ ID NO: 89        moltype = DNA   length = 376
FEATURE              Location/Qualifiers
source               1..376
                     mol_type = other DNA
                     organism = Bacillus weihenstephanensis
SEQUENCE: 89
ggtaggtaga tttgaaatat gatgaagaaa aggaataact aaaaggagtc gatatccgac    60
tcctttagt tataaataat gtggaattag agtataattt tataggta tattgtatta     120
gatgaacgct ttatccttta attgtgatta atgatggatt gtaagagaag gggcttacag   180
tcctttttt atggtgttct ataagccttt ttaaaagggg taccaccca cacccaaaaa    240
caggggggt tataactaca tattggatgt tttgtaacgt acaagaatcg gtattaatta    300
ccctgtaaat aagttatgtg tatataaggt aactttatat attctcctac aataaaataa   360
aggaggtaat aaagtg                                                   376

SEQ ID NO: 90        moltype = DNA   length = 225
FEATURE              Location/Qualifiers
source               1..225
                     mol_type = other DNA
                     organism = Bacillus thuringiensis
SEQUENCE: 90
aacccttaat gcattggtta aacattgtaa agtctaaagc atggataatg ggcgagaagt    60
aagtagattg ttaacaccct gggtcaaaaa ttgatattta gtaaaattag ttgcactttg   120
tgcatttttt cataagatga gtcatatgtt taaattgta gtaatgaaaa acagtattat    180
atcataatga attggtatct taataaaaga gatggaggta actta                   225

SEQ ID NO: 91        moltype = DNA   length = 125
FEATURE              Location/Qualifiers
source               1..125
                     mol_type = other DNA
                     organism = Bacillus thuringiensis
SEQUENCE: 91
taattccacc ttcccttatc ctctttcgcc tatttaaaaa aaggtcttga gattgtgacc    60
aaatctcctc aactccaata tcttattaat gtaaatacaa acaagaagat aaggagtgac   120
attaa                                                               125

SEQ ID NO: 92        moltype = DNA   length = 144
FEATURE              Location/Qualifiers
source               1..144
                     mol_type = other DNA
                     organism = Bacillus thuringiensis
SEQUENCE: 92
aggatgtctt tttttatatt gtattatgta catccctact atataaattc cctgcttta     60
tcgtaagaat taacgtaata tcaaccatat cccgttcata ttgtagtagt gtatgtcaga   120
actcacgaga aggagtgaac ataa                                          144

SEQ ID NO: 93        moltype = DNA   length = 126
FEATURE              Location/Qualifiers
source               1..126
                     mol_type = other DNA
                     organism = Bacillus thuringiensis
SEQUENCE: 93
ttaatgtcac tccttatctt cttgtttgta tttacattaa taagatattg gagttgagga    60
gatttggtca caatctcaag accttttttt taaataggcg aaagaggata agggaaggtg   120
gaatta                                                              126

SEQ ID NO: 94        moltype = DNA   length = 103
FEATURE              Location/Qualifiers
source               1..103
                     mol_type = other DNA
                     organism = Bacillus thuringiensis
SEQUENCE: 94
atatattttc ataatacgag aaaaagcgga gtttaaaaga atgagggaac ggaaataaag    60
agttgttcat atagtaaaata gacagaattg acagtagagg aga                    103

SEQ ID NO: 95        moltype = DNA   length = 169
FEATURE              Location/Qualifiers
source               1..169
                     mol_type = other DNA
                     organism = Bacillus thuringiensis
SEQUENCE: 95
```

```
aaactaaata atgagctaag catggattgg gtggcagaat tatctgccac ccaatccatg    60
cttaacgagt attattatgt aaatttctta aaattgggaa cttgtctaga acatagaacc   120
tgtccttttc attaactgaa agtagaaaca gataaaggag tgaaaaaca               169

SEQ ID NO: 96           moltype = DNA   length = 111
FEATURE                 Location/Qualifiers
source                  1..111
                        mol_type = other DNA
                        organism = Bacillus thuringiensis
SEQUENCE: 96
attcactaca acgggatga gtttgatgcg gatacatatg agaagtaccg gaaagtgttt     60
gtagaacatt acaaagatat attatctcca tcataaagga gagatgcaaa g            111

SEQ ID NO: 97           moltype = DNA   length = 273
FEATURE                 Location/Qualifiers
source                  1..273
                        mol_type = other DNA
                        organism = Bacillus anthracis
SEQUENCE: 97
cgcgcaccac ttcgtcgtac aacaacgcaa gaagaagttg gggatacagc agtattctta    60
ttcagtgatt tagcacgcgg cgtaacagga gaaaacattc acgttgattc agggtatcat   120
atcttaggat aaatataata ttaatttaaa aggacaagtc ctacatgttg agattgtcct   180
ttttatttgt tcttagaaag aacgattttt aacgaaagtc cttaccacgt tatgaatata   240
agtataatag tacacgattt attcagctac gta                                273

SEQ ID NO: 98           moltype = DNA   length = 303
FEATURE                 Location/Qualifiers
source                  1..303
                        mol_type = other DNA
                        organism = Bacillus anthracis
SEQUENCE: 98
tgaagtatct agagctaatt tacgcaaagg aatctcagga caacactttc gcaacaccta    60
tattttaaat ttaataaaaa aagagactcc ggagtcagaa attataaagc tagctgggtt   120
caaatcaaaa atttcactaa aacgatatta tcaatacgca gaaaatggaa aaaacgcctt   180
atcataaggc gttttttcca tttttcttc aaacaaacga tttactatg accatttaac    240
taattttttgc atctactatg atgagtttca ttcacattct cattagaaag agagattta    300
atg                                                                 303

SEQ ID NO: 99           moltype = DNA   length = 240
FEATURE                 Location/Qualifiers
source                  1..240
                        mol_type = other DNA
                        organism = Bacillus anthracis
SEQUENCE: 99
tatatcatat gtaaaattag ttcttattcc cacatatcat atagaatcgc catattatac    60
atgcagaaaa ctaagtatgg tattattctt aaattgttta gcaccttcta atattacaga   120
tagaatccgt cattttcaac agtgaacatg gatttcttct gaacacaact cttttttctt   180
ccttatttcc aaaaagaaaa gcagcccatt ttaaaatacg gctgcttgta atgtacatta   240

SEQ ID NO: 100          moltype = DNA   length = 267
FEATURE                 Location/Qualifiers
source                  1..267
                        mol_type = other DNA
                        organism = Bacillus thuringiensis
SEQUENCE: 100
tatcacataa ctctttattt ttaatatttc gacataaagt gaaactttaa tcagtggggg    60
ctttgttcat cccccccactg attattaatt gaaccaaggg ataaaagat agagggtctg   120
accagaaaac tggagggcat gattctataa caaaaagctt aatgtttata gaattatgtc   180
ttttttatata gggagggtag taaacagaga tttggacaaa aatgcaccga tttatctgaa   240
ttttaagttt tataaagggg agaaatg                                       267

SEQ ID NO: 101          moltype = DNA   length = 124
FEATURE                 Location/Qualifiers
source                  1..124
                        mol_type = other DNA
                        organism = Bacillus thuringiensis
SEQUENCE: 101
attttttact tagcagtaaa actgatatca gttttactgc ttttttcattt ttaaattcaa    60
tcattaaatc ttcctttttct acatagtcat aatgttgtat gacattccgt aggaggcact   120
tata                                                                 124

SEQ ID NO: 102          moltype = DNA   length = 170
FEATURE                 Location/Qualifiers
source                  1..170
                        mol_type = other DNA
                        organism = Bacillus thuringiensis
SEQUENCE: 102
acataaattc acctccataa agcgttcatt atatagtaga tgcaaaaccg aaagaaaatg    60
acacggacat tgaattattg gaaagaaat cttaaactac ttgaacaatt taaaaaaatg    120
```

```
gaaagtttag tatatgtata acatatgatt gatttggaag agggtgatta              170

SEQ ID NO: 103          moltype = DNA  length = 212
FEATURE                 Location/Qualifiers
source                  1..212
                        mol_type = other DNA
                        organism = Bacillus thuringiensis
SEQUENCE: 103
ttctattttc caacataaca tgctacgatt aaatggtttt ttgcaaatgc cttcttggga   60
agaaggatta gagcgttttt ttatagaaac caaaagtcat taacaatttt aagttaatga  120
cttttttgtt tgcctttaag aggttttatg ttactataat tatagtatca ggtactaata  180
acaagtataa gtatttctgg gaggatatat ca                                212

SEQ ID NO: 104          moltype = DNA  length = 1500
FEATURE                 Location/Qualifiers
source                  1..1500
                        mol_type = other DNA
                        organism = Bacillus subtilis
SEQUENCE: 104
atgaaacggt caatctcgat ttttattacg tgtttattga ttacgttatt gacaatgggc   60
ggcatgatag cttcgccggc atcagcagca gggacaaaaa cgccagtagc caagaatggc  120
cagcttagca taaaaggtac acagctcgtt aaccgagacg gtaaagcggt acagctgaag  180
gggatcagtt cacacggatt gcaatggtat ggagaatatg tcaataaaga cagcttaaaa  240
tggctgagag atgattgggg tatcaccgtt tccgtgcagc gatgtatac ggcagatggc  300
ggttatattg acaacccgtc cgtgaaaaat aaagtaaaag aagcggttga agcggcaaaa  360
gagcttggga tatatgtcat cattgactgg catatcttaa atgacggtaa tccaaaccaa  420
aataaagaga aggcaaaaga attcttcaag gaaatgtcaa gcctttacgg aaacacgcca  480
aacgtcattt tgaaattgc aaacgaacca aacggtgatg tgaactggaa gcgtgatatt  540
aaaccatatg cggaagaagt gatttcagtt atccgcaaaa atgatccaga caacatcatc  600
attgtcggaa ccggtacatg gagccaggat gtgaatgatg ctgccgatga ccagctaaaa  660
gatgcaaacg ttatgtacgc acttcattt tatgccggca cacacggcca attttttacgg  720
gataaagcaa actatgcact cagcaaagga gcacctattt ttgtgacaga gtggggaaca  780
agcgacgcgt ctggcaatgg cggtgtattc cttgatcaat cgagggaatg gctgaaatat  840
ctcgacagca agaccattag ctgggtgaac tggaatcttt ctgataagca ggaatcatcc  900
tcagctttaa agccggggc atctaaaaca ggcggctggc ggttgtcaga tttatctgct  960
tcaggaacat tcgttagaga aaacattctc ggcaccaaag attcgacgaa ggacattcct 1020
gaaacgccat caaagataa acccacacag gaaaatggta tttctgtaca gtacagagca 1080
gggggatggga gtatgaacag caaccaaatc cgtccgcagc ttcaaataaa aataacggc  1140
aataccacgg ttgatttaaa agatgtcact gcccgttact ggtataaagc gaaaacaaa  1200
ggccaaaact ttgactgtga ctacgcgcag attggatgcg gcaatgtgac acacaagttt 1260
gtgacgttgc ataaaccaaa gcaaggtgca gatacctatc tggaacttgg atttaaaaac 1320
ggaacgttgg caccgggagc aagcacaggg aatattcagc tccgtcttca caatgatgac 1380
tggagcaatt atgcacaaag cggcgattat tccttttca aatcaaatac gtttaaaaca 1440
acgaaaaaaa tcacattata tgatcaagga aaactgattt ggggaacaga accaaattag 1500

SEQ ID NO: 105          moltype = DNA  length = 852
FEATURE                 Location/Qualifiers
source                  1..852
                        mol_type = other DNA
                        organism = Bacillus thuringiensis
SEQUENCE: 105
atgaaaaaga aagtacttgc tttagcggca gctattacat tggttgctcc attacaaagt   60
gttgcatttg ctcatgaaaa tgatggggga cagagatttg gagttattcc gcgctggtct  120
gctgaagata aacataaaga aggcgtgaat tctcatttat ggattgtaaa tcgtgcaatt  180
gatattatgt ctcgtaatac aacacttgta aaacaagatc gagttgcact attaaatgaa  240
tggcgtactg agttagaaa cggtatttat gctgctgact atgaaaatcc ttattatgat  300
aatagccat ttgcttcaca tttctatgac cctgacaatg gaaaacttta tattccgtat  360
gcaaagcagg caaaggaaac tggagctaaa tattttaaat tagctggtga gtcttacaaa  420
aataaaagata tgcaacaagc attcttctat ttaggattat ctcttcatta tctagggga  480
gtaaaccaac cgatgcatgc agcaaacttt acaaaccttt cgtatccaca agggttccat  540
tctaaatatg aaaactttgt agatacgata aagataact ataaagtaac ggatggaaat  600
ggatattgga actggaaagg tacgaatcca aagattgga ttcatggagc ggcagtagtt  660
gcgaaacaag ttacgctgg cattgtaaat gataatacga agattggtt cgtgagagct  720
gctgtatcac aagaatatgc agataaatgg cgcgctgaag ttacaccaat gacaggtaag  780
cgtttaatgg atgcacaacg tgttactgct ggatatattc agctttggtt tgatacgtac  840
ggagatcgtt aa                                                      852

SEQ ID NO: 106          moltype = DNA  length = 729
FEATURE                 Location/Qualifiers
source                  1..729
                        mol_type = other DNA
                        organism = Bacillus subtilis
SEQUENCE: 106
gcgggactga ataaagatca aaagcgccgg gcggaacagc tgacaagtat ctttgaaaac   60
ggcacaacgg agatccaata tggatatgta gagcgattgg atgacgggcg aggctataca  120
tgcggacggg caggctttac aacgtgtacc ggggatgcat tggaagtagt ggaagtatac  180
acaaaggcag ttccgaataa caaactgaaa agtatctgc ctgaattgcg ccgtctggcc  240
aaggaagaaa gcgatgatac aagcaatctc aagggattgc cttctgcctg gaagtcgctt  300
gcaaatgata aggaatttcg cgccgctcaa gacaaagtaa atgaccattt gtattatcag  360
```

```
cctgccatga aacgatcgga taatgccgga ctaaaaacag cattggcaag agctgtgatg  420
tacgatacgg ttattcagca tggcgatggt gatgaccctg actcttttta tgccttgatt  480
aaacgtacga acaaaaaagc gggcggatca cctaaagacg gaatagacga gaagaagtgg  540
ttgaataaat tcttggacgt acgctatgac gatctgatga atccggccaa tcatgacacc  600
cgtgacgaat ggagagaatc agttgcccgt gtggacgtgc ttcgctctat cgccaaggag  660
aacaactata atctaaacgg accgattcat gttcgttcaa acgagtacgg taattttgta  720
atcaaataa                                                          729

SEQ ID NO: 107          moltype = AA   length = 499
FEATURE                 Location/Qualifiers
source                  1..499
                        mol_type = protein
                        organism = Bacillus subtilis
SEQUENCE: 107
MKRSISIFIT CLLITLLLTMG GMIASPASAA GTKTPVAKNG QLSIKGTQLV NRDGKAVQLK   60
GISSHGLQWY GEYVNKDSLK WLRDDWGITV FRAAMYTADG GYIDNPSVKN KVKEAVEAAK  120
ELGIYVIIDW HILNDGNPNQ NKEKAKEFFK EMSSLYGNTP NVIYEIANEP NGDVNWKRDI  180
KPYAEEVISV IRKNDPDNII IVGTGTWSQD VNDAADDQLK DANVMYALHF YAGTHGQFLR  240
DKANYALSKG APIFVTEWGT SDASGNGGVF LDQSREWLKY LDSKTISWVN WNLSDKQESS  300
SALKPGASKT GGWRLSDLSA SGTFVRENIL GTKDSTKDIP ETPSKDKPTQ ENGISVQYRA  360
GDGSMNSNQI RPQLQIKNNG NTTVDLKDVT ARYWYKAKNK GQNFDCDYAQ IGCGNVTHKF  420
VTLHKPKQGA DTYLELGFKN GTLAPGASTG NIQLRLHNDD WSNYAQSGDY SFFKSNTFKT  480
TKKITLYDQG KLIWGTEPN                                               499

SEQ ID NO: 108          moltype = AA   length = 283
FEATURE                 Location/Qualifiers
source                  1..283
                        mol_type = protein
                        organism = Bacillus thuringiensis
SEQUENCE: 108
MKKKVLALAA AITLVAPLQS VAFAHENDGG QRFGVIPRWS AEDKHKEGVN SHLWIVNRAI   60
DIMSRNTTLV KQDRVALLNE WRTELENGIY AADYENPYYD NSTFASHFYD PDNGKTYIPY  120
AKQAKETGAK YFKLAGESYK NKDMQQAFFY LGLSLHYLGD VNQPMHAANF TNLSYPQGFH  180
SKYENFVDTI KDNYKVTDGN GYWNWKGTNP EDWIHGAAVV AKQDYAGIVN DNTKDWFVRA  240
AVSQEYADKW RAEVTPMTGK RLMDAQRVTA GYIQLWFDTY GDR                    283

SEQ ID NO: 109          moltype = AA   length = 244
FEATURE                 Location/Qualifiers
source                  1..244
                        mol_type = protein
                        organism = Bacillus subtilis
SEQUENCE: 109
LEAGLNKDQK RRAEQLTSIF ENGTTEIQYG YVERLDDGRG YTCGRAGFTT ATGDALEVVE   60
VYTKAVPNNK LKKYLPELRR LAKEESDDTS NLKGFASAWK SLANDKEFRA AQDKVNDHLY  120
YQPAMKRSDN AGLKTALARA VMYDTVIQHG DGDDPDSFYA LIKRTNKKAG GSPKDGIDEK  180
KWLNKFLDVR YDDLMNPANH DTRDEWRESV ARVDVLRSIA KENNYNLNGP IHVRSNEYGN  240
FVIK                                                               244
```

What is claimed is:

1. A method of treating a plant, a plant part, or the locus surrounding the plant to enhance plant growth and/or promote plant health comprising the step of simultaneously or sequentially applying:
   a) recombinant cells of a *Bacillus cereus* family member, wherein the cells express a fusion protein comprising:
      (i) at least one plant growth stimulating protein or peptide selected from the group consisting of a polypeptide having endoglucanase activity and at least 90% sequence identity to SEQ ID NO: 107 and a phospholipase polypeptide having phospholipase activity and at least 90% sequence identity to SEQ ID NO: 108; and
      (ii) a targeting sequence, exosporium protein, or exosporium protein fragment that is capable of targeting the fusion protein to the exosporium of the recombinant *Bacillus cereus* family member, comprising:
         an amino acid sequence having at least 43% identity with amino acids 20-35 of SEQ ID NO: 1, wherein the identity with amino acids 25-35 is at least 54%;
         amino acids 1-35 of SEQ ID NO: 1;
         amino acids 20-35 of SEQ ID NO: 1;
         amino acids 22-31 of SEQ ID NO: 1;
         amino acids 22-33 of SEQ ID NO: 1;
         amino acids 20-31 of SEQ ID NO: 1;
         the amino acid sequence of SEQ ID NO: 1; or
         an amino acid sequence having at least 85% sequence identity to SEQ ID NO: 2; and
   b) a *Bacillus firmus* strain
   in a synergistic weight ratio in the range of 1:1000 to 1000:1, wherein the synergism refers to the effect of enhancing plant growth and/or promoting plant health.

2. The method of claim 1, wherein the *Bacillus cereus* family member is selected from the group consisting of *Bacillus anthracis*, *Bacillus cereus*, *Bacillus thuringiensis*, *Bacillus mycoides*, *Bacillus pseudomycoides*, *Bacillus samanii*, *Bacillus gaemokensis*, *Bacillus weihenstephensis*, *Bacillus toyoiensis*, and combinations thereof.

3. The method of claim 1, wherein the fusion protein comprises SEQ ID NO:107.

4. The method of claim 3, wherein the recombinant *Bacillus* cells are from *Bacillus thuringiensis* BT013A.

5. The method of claim 1, wherein the fusion protein comprises SEQ ID NO:108.

6. The method of claim 1, wherein the fusion protein is expressed under the control of a sporulation promoter native to the targeting sequence, exosporium protein, or exosporium protein fragment of the fusion protein.

7. The method of claim 1, wherein the fusion protein is expressed under the control of a high-expression sporulation promoter.

8. The method of claim 7, wherein the high-expression sporulation promoter comprises a sigma-K sporulation-specific polymerase promoter sequence.

9. The method of claim 6, wherein the sporulation promoter comprises a nucleic acid sequence having at least 80% identity with a nucleic acid sequence of any one of SEQ ID NOs: 85-103.

10. The method of claim 1, wherein the at least one plant growth stimulating protein or peptide is an endoglucanase with at least 95% sequence identity to SEQ ID NO: 107.

11. The method of claim 1, wherein the at least one plant growth stimulating protein or peptide is an endoglucanase with at least 98% sequence identity to SEQ ID NO: 107.

12. The method of claim 1, wherein the at least one plant growth stimulating protein or peptide is a phospholipase with at least 95% sequence identity to SEQ ID NO: 108.

13. The method of claim 1, wherein the at least one plant growth stimulating protein or peptide is a phospholipase with at least 98% sequence identity to SEQ ID NO: 108.

14. The method of claim 11, wherein the targeting sequence comprises amino acids 20-35 of SEQ ID NO:1.

15. The method of claim 13, wherein the targeting sequence comprises amino acids 20-35 of SEQ ID NO:1.

16. The method of claim 14, wherein the *Bacillus firmus* strain is *Bacillus firmus* strain 1-1582.

17. The method of claim 15, wherein the *Bacillus firmus* strain is *Bacillus firmus* strain 1-1582.

18. The method of claim 16, wherein the fusion protein is expressed under the control of a sporulation promoter comprising a nucleic acid sequence having at least 80% identity with a nucleic acid sequence of any one of SEQ ID NOs: 85-103.

19. The method of claim 18, wherein the sporulation promoter comprises a nucleic acid sequence having 100% identity with the nucleic acid sequence of SEQ ID NO: 85.

20. The method of claim 19, wherein the endoglucanase has 100% sequence identity to SEQ ID NO: 107.

* * * * *